US012595243B2

(12) United States Patent
Galan et al.

(10) Patent No.: US 12,595,243 B2
(45) Date of Patent: *Apr. 7, 2026

(54) MODULATORS OF EXTRACELLULAR SIGNAL-REGULATED KINASE

(71) Applicant: GEN1E LIFESCIENCES INC., Palo Alto, CA (US)

(72) Inventors: Adam Galan, Alameda, CA (US); Ritu Lal, Palo Alto, CA (US); Chakk Ramesha, Palo Alto, CA (US)

(73) Assignee: GEn1E Lifesciences Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/920,162

(22) Filed: Oct. 18, 2024

(65) Prior Publication Data

US 2025/0136571 A1 May 1, 2025

Related U.S. Application Data

(60) Provisional application No. 63/544,756, filed on Oct. 18, 2023.

(51) Int. Cl.

| | |
|---|---|
| ***C07D 333/48*** | (2006.01) |
| ***A61K 31/381*** | (2006.01) |
| ***A61P 35/00*** | (2006.01) |

(52) U.S. Cl.

CPC .......... *C07D 333/48* (2013.01); *A61K 31/381* (2013.01); *A61P 35/00* (2018.01)

(58) Field of Classification Search

CPC ...... C07D 333/48; A61P 35/00; A61K 31/381

See application file for complete search history.

(56) References Cited

U.S. PATENT DOCUMENTS

| | | | |
|---|---|---|---|
| 8,642,660 | B2 | 2/2014 | Goldfarb |
| 9,115,112 | B2 | 8/2015 | Shapiro et al. |
| 2004/0137472 | A1 | 7/2004 | Kole |
| 2009/0163545 | A1 | 6/2009 | Goldfarb |

FOREIGN PATENT DOCUMENTS

| | | | |
|---|---|---|---|
| WO | 2004/089276 | A2 | 10/2004 |
| WO | 2006/018662 | A2 | 2/2006 |

OTHER PUBLICATIONS

Shapiro (Biochem. J. (2015) 467, 425-438) (Year: 2015).*

Ansel (Ansel's Pharmaceutical Dosage Forms and Drug Delivery Systems. 10th. Wolters Kluwer Health. 2013. p. 102) (Year: 2013).*

Biava et al., Synthesis and antimycobacterial activity of new amido derivatives of ortho-, meta- and para-toluidine, Med. Chem. Res. 8:9 (1998), pp. 523-541, 19 pages.

Guo et al., ERK/MAPK signaling pathway and tumorigenesis (Review), Experimental and Therapeutic Medicine, 19, pp. 1997-2007, 2020, DOI: 10.3892/etm.2020.8454, 11 pages.

Xia et al., Synthesis and evaluation of novel inhibitors of Pim-1 and Pim-2 protein kinases, J. Med. Chem. 51(1), 2009, pp. 74-86, doi:10.1021/jm800937p., 38 pages.

Martinez III et al., Mechanistic analysis of an extracellular signal-regulated kinase 2-interacting compound that inhibits mutant BRAF-expressing melanoma cells by inducing oxidative stress, Journal of Pharmacology and Experimental Therapeutics, 376, 84-97, Jan. 2021, 31 pages.

Song et al., Targeting RAS-RAF-MEK-ERK signaling pathway in human cancer: Current status in clinical trials, Genes & Diseases, 10, 2023, pp. 76-88, 13 pages.

Samadani, et al., Small-molecule inhibitors of ERK-mediated immediate early gene expression and proliferation of melanoma cells expressing mutated BRaf, Biochem. J. May 1, 2015, 467(3), pp. 425-438, doi:10.1042/BJ20131571, 29 pages.

Sun, et al., Discovery and antitumor evaluation of novel inhibitors of spermine oxidase, Journal of Enzyme Inhibition and Medicinal Chemistry, 34:1, pp. 1140-1151, doi:10.1080/14756366.2019.1621863, 13 pages.

* cited by examiner

*Primary Examiner* — Kortney L. Klinkel

*Assistant Examiner* — Richard Grant Peckham

(74) *Attorney, Agent, or Firm* — Sheppard Mullin Richter & Hampton LLP

(57) ABSTRACT

Modulators of extracellular signal-regulated kinase, pharmaceutical compositions thereof, and uses of the compound and pharmaceutical compositions thereof for treating cancer and pulmonary diseases are disclosed.

17 Claims, No Drawings

MODULATORS OF EXTRACELLULAR SIGNAL-REGULATED KINASE

This application claims the benefit under 35 U.S.C. § 119(e) of U.S. Provisional Application No. 63/544,756 filed on Oct. 18, 2023, which is incorporated by reference in its entirety.

FIELD

The present disclosure relates to modulators of extracellular signal-regulated kinase, pharmaceutical compositions thereof, and the use of the extracellular signal-regulated kinase modulators and pharmaceutical compositions for treating diseases such as cancer and pulmonary diseases.

BACKGROUND

Allergen-induced inflammatory mediators act on immune cells and structural airways cells and activate intracellular signaling. The Activator Protein-1 (AP-1) transcription factor complex is a central regulator that responds to signaling pathways activated by cytokines, growth factors, and other inflammatory signals in airway cells to mediate airway remodeling in pulmonary diseases such as asthma. Therefore, upregulated AP-1, which contributes to multiple features of asthma pathogenesis, is an attractive anti-asthma therapeutic target. The Extracellular Signal-Regulated Protein Kinases (ERK1/2) are key regulators of AP-1 activity in airway smooth muscle (ASM), lung fibroblasts (LF), and other lung cells that contribute to the pathology of asthma. Taking advantage of ERK1/2 structural interactions with specific substrates, a unique ERK1/2 substrate docking site that mediates interactions with AP-1 complex proteins and inhibits ERK1/2-mediated AP-1 activity was identified and is described in U.S. Pat. No. 9,115,122. Targeting select kinase functions can reduce acquired drug resistance and toxicity observed with certain kinase inhibitors that target ATP binding sites and block all enzymatic activity. Considering that upregulated ERK1/2 activity contributes to the pathogenesis of pulmonary diseases such as asthma, function-selective inhibition of ERK1/2 signaling through the AP-1 can potentially mitigate ASM and LF cell hyperplasia, hypertrophy, extracellular matrix (ECM) hypersecretion, and other features of asthma.

SUMMARY

According to the present invention compounds have the structure of Formula (1) or the structure of Formula (2):

(1)

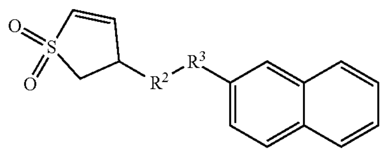

(2)

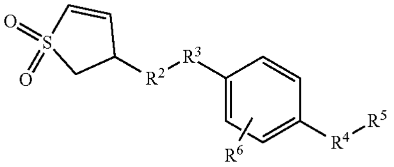

or is a pharmaceutically acceptable salt thereof, wherein, $R^2$ is selected from —O—, —NH—, and —N(—$CH_3$)—;

$R^3$ is selected from $C_{1-3}$ alkane-diyl and $C_{1-3}$ heteroalkane-diyl;

$R^4$ is absent or is selected from $C_{1-2}$ alkane-diyl, $C_{1-2}$ heteroalkane-diyl, substituted $C_{1-2}$ alkane-diyl, and substituted $C_{1-2}$ heteroalkane-diyl;

$R^5$ is selected from $C_{5-10}$ cycloalkyl, $C_{5-20}$ aryl, $C_{5-10}$ heterocycloalkyl, $C_{5-20}$ heteroaryl, substituted $C_{5-10}$ cycloalkyl, substituted $C_{5-20}$ aryl, substituted $C_{5-10}$ heterocycloalkyl, and substituted $C_{5-20}$ heteroaryl; and $R^6$ is absent or is selected from $C_{1-3}$ alkyl and $C_{1-3}$ alkoxy.

According to the present invention pharmaceutical compositions comprise a compound according to the present invention or a pharmaceutically acceptable salt thereof, and a pharmaceutically acceptable vehicle.

According to the present invention methods of treating a disease in a patient comprise administering to a patient in need of such treatment a therapeutically effective amount of a compound according to the present invention or a pharmaceutically acceptable salt thereof, or a pharmaceutical composition according to the present invention, wherein the disease is treated by inhibiting extracellular signal-regulated kinase 1 and/or extracellular signal-regulated kinase 2.

According to the present invention methods of treating a disease in a patient comprise administering to a patient in need of such treatment a therapeutically effective amount of a compound according to the present invention or a pharmaceutically acceptable salt thereof, or a pharmaceutical composition according to the present invention, wherein the disease is selected from cancer, an inflammatory disease, an autoimmune disease, or a pulmonary disease.

According to the present invention methods of treating a disease in a patient comprise administering to a patient in need of such treatment a therapeutically effective amount of a compound according to the present invention, or a pharmaceutical composition according to the present invention, wherein the disease is treated by inhibiting extracellular signal-regulated kinase 1 and/or extracellular signal-regulated kinase 2.

According to the present invention methods of treating a disease in a patient comprise administering to a patient in need of such treatment a therapeutically effective amount of a compound according to the present invention, or a pharmaceutical composition according to the present invention, wherein the disease is selected from cancer, an inflammatory disease, an autoimmune disease, or a pulmonary disease.

According to the present invention methods of treating a disease in a patient comprise administering to a patient in need of such treatment a therapeutically effective amount of a compound according to the present invention or a pharmaceutically acceptable salt thereof, or a pharmaceutical composition according to the present invention, wherein the disease is selected from acute coronary syndrome, acute lung injury, acute respiratory distress syndrome (ARDS), Alzheimer's disease, asthma, a cardiovascular disease, chronic obstructive pulmonary disease (COPD), inflammatory bowel disease, major depressive disorder, multiple sclerosis, neuropathic pain, and rheumatoid arthritis.

According to the present invention methods of treating a disease in a patient comprise administering to a patient in need of such treatment a therapeutically effective amount of a pharmaceutical composition according to the present invention, or a pharmaceutical composition according to the present invention, wherein the disease is selected from acute coronary syndrome, acute lung injury, acute respiratory distress syndrome (ARDS), Alzheimer's disease, asthma, a cardiovascular disease, chronic obstructive pulmonary disease (COPD), inflammatory bowel disease, major depressive disorder, multiple sclerosis, neuropathic pain, and rheumatoid arthritis.

DETAILED DESCRIPTION

A dash ("-") that is not between two letters or symbols is used to indicate a point of attachment for a moiety or substituent. For example, $—CONH_2$ is attached through the carbon atom.

"Alkyl" refers to a saturated, branched, or straight-chain, monovalent hydrocarbon radical derived by the removal of one hydrogen atom from a single carbon atom of a parent alkane, alkene, or alkyne. Examples of alkyl groups include methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like. The term "alkyl" includes groups having any degree or level of saturation, i.e., groups having exclusively carbon-carbon single bonds, groups having one or more carbon-carbon double bonds, groups having one or more carbon-carbon triple bonds, and groups having combinations of carbon-carbon single, double, and triple bonds. Where a specific level of saturation is intended, the terms alkanyl, alkenyl, and alkynyl are used. An alkyl group can be $C_{1-6}$ alkyl, $C_{1-5}$ alkyl, $C_{1-4}$ alkyl, $C_{1-3}$ alkyl, ethyl or methyl.

"Alkoxy" refers to a radical —OR where R is alkyl as defined herein. Examples of alkoxy groups include methoxy, ethoxy, propoxy, and butoxy. An alkoxy group can be $C_{1-6}$ alkoxy, $C_{1-5}$ alkoxy, $C_{1-4}$ alkoxy, $C_{1-3}$ alkoxy, ethoxy or methoxy.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms selected from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like. An aryl group can be $C_{6-10}$ aryl, $C_{6-9}$ aryl, $C_{6-8}$ aryl, or phenyl. Aryl, however, does not encompass or overlap in any way with heteroaryl, separately defined herein.

"Cycloalkyl" refers to a saturated or partially unsaturated cyclic alkyl radical. A cycloalkyl group can be $C_{3-8}$ cycloalkyl, $C_{3-5}$ cycloalkyl, $C_{5-6}$ cycloalkyl, cyclopropyl, cyclopentyl, or cyclohexyl. A cycloalkyl can be selected from cyclopropyl, cyclobutyl, cyclopentyl, cyclohexyl, cycloseptyl, and cyclooctyl.

"Heteroalkyl" by itself or as part of another substituent refer to an alkyl group in which one or more of the carbon atoms (and certain associated hydrogen atoms) are independently replaced with the same or different heteroatomic group or groups. Examples of heteroatomic groups include —O—, —S—, —Si—, —B—, —NH—, —NR—, —O—O—, —S—S—, =N—N=, —N=N—, —N=N—NR—, —PR—, —P(O)OR—, —P(O)R—, —POR—, —SO—, $—SO_2—$, and $—Sn(R)_2—$, where each R is independently selected from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$heteroalkyl, $C_{6-12}$heteroaryl, substituted $C_{6-12}$ heteroaryl, $C_{7-18}$ heteroarylalkyl, and substituted $C_{7-18}$ heteroarylalkyl. Each R can be independently selected from hydrogen and $C_{1-3}$ alkyl. Reference to, for example, a $C_{1-6}$ heteroalkyl, means a $C_{1-6}$ alkyl group in which at least one of the carbon atoms (and certain associated hydrogen atoms) is replaced with a heteroatom. For example, $C_{1-6}$ heteroalkyl includes groups having five carbon atoms and one heteroatom, groups having four carbon atoms and two heteroatoms. In a heteroalkyl, the heteroatomic group can be selected from —O—, —S—, —NH—, $—N(—CH_3)—$, —SO—, $—SO_2—$, —Si—, and —B—, or the heteroatomic group can be selected from —O— and —NH—, or the heteroatomic group can be —O— or —NH—. A heteroalkyl group can be $C_{1-6}$ heteroalkyl, $C_{1-5}$ heteroalkyl, or $C_{1-4}$ heteroalkyl, or $C_{1-3}$ heteroalkyl.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which may be aromatic or non-aromatic. For example, heteroaryl encompasses bicyclic rings in which one ring is heteroaromatic and the second ring is a heterocycloalkyl ring. For such fused, bicyclic heteroaryl ring systems wherein only one of the rings contains one or more heteroatoms, the radical carbon may be at the aromatic ring or at the heterocycloalkyl ring. When the total number of N, S, and O atoms in the heteroaryl group exceeds one, the heteroatoms may or may not be adjacent to one another. The total number of heteroatoms in the heteroaryl group is not more than two. In a heteroaryl, the heteroatomic group can be selected from —O—, —S—, —NH—, $—N(—CH_3)—$, —SO—, $—SO_2—$, —Si—, and —B—, or the heteroatomic group can be selected from —O— and —NH—, or the heteroatomic group can be —O— or —NH—. A heteroaryl group can be selected from, for example, $C_{5-10}$ heteroaryl, $C_{5-9}$ heteroaryl, $C_{5-8}$ heteroaryl, $C_{5-7}$heteroaryl, $C_{5-6}$ heteroaryl, $C_5$ heteroaryl or $C_6$ heteroaryl.

Examples of heteroaryl groups include groups derived from acridine, arsindole, carbazole, α-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, and oxazolidine. A heteroaryl groups can be derived, for example, from thiophene, pyrrole, benzothiophene, benzofuran, indole, pyridine, quinoline, imidazole, oxazole, or pyrazine. For example, a heteroaryl can be $C_5$ heteroaryl and can be selected from furyl, thienyl, pyrrolyl, imidazolyl, pyrazolyl, isothiazolyl, or isoxazolyl. A heteroaryl can be $C_6$ heteroaryl, and can be selected from pyridinyl, pyrazinyl, pyrimidinyl, and pyridazinyl.

"Parent aromatic ring system" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene.

"Parent heteroaromatic ring system" refers to an aromatic ring system in which one or more carbon atoms (and any associated hydrogen atoms) are independently replaced with the same or different heteroatom in such a way as to maintain the continuous π-electron system characteristic of aromatic systems and a number of π-electrons corresponding to the Hückel rule (4n+2). Examples of heteroatoms to replace the carbon atoms include N, P, O, S, Si, and B. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and thiazolidine, oxazolidine.

"Substituted" refers to a group in which one or more hydrogen atoms are independently replaced with the same or different substituent(s). Each substituent can be independently selected from deuterio, halogen, —OH, —CN, $—CF_3$, $—OCF_3$, =O, $—NO_2$, $C_{1-6}$ alkoxy, $C_{1-6}$ alkyl, —COOR, $—NR_2$, and $—CONR_2$; wherein each R is independently selected from hydrogen and $C_{1-6}$ alkyl. Each substituent can be independently selected from deuterio, halogen, $—NH_2$, —OH, $C_{1-3}$ alkoxy, and $C_{1-3}$ alkyl, trifluoromethoxy, and trifluoromethyl. Each substituent can be independently selected from deuterio, —OH, methyl, ethyl, trifluoromethyl, methoxy, ethoxy, and trifluoromethoxy. Each substituent can independently be selected from deuterio, $C_{1-3}$ alkyl, =O, $C_{1-3}$ alkyl, $C_{1-3}$ alkoxy, and phenyl. Each substituent can independently be selected from deuterio, —OH, $—NH_2$, $C_{1-3}$ alkyl, and $C_{1-3}$ alkoxy.

"Compounds" and moieties disclosed herein include any specific compounds within the disclosed formula. Compounds may be identified either by chemical structure and/or by chemical name. Compounds are named using the ChemBioDraw Professional 17.1.0.105 (9) (CambridgeSoft, Cambridge, MA) nomenclature program. The compounds described herein may comprise one or more stereogenic centers and/or double bonds and therefore may exist as stereoisomers such as double-bond isomers (i.e., geometric isomers), enantiomers, diastereomers, or atropisomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled in the art.

Compounds and moieties disclosed herein include optical isomers of compounds and moieties, racemates thereof, and other mixtures thereof. In such embodiments, the single enantiomers or diastereomers may be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column with chiral stationary phases. In addition, compounds include (Z)- and (E)-forms (or cis- and trans-forms) of compounds with double bonds either as single geometric isomers or mixtures thereof.

Compounds and moieties may also exist in several tautomeric forms including the enol form, the keto form, and mixtures thereof. Accordingly, the chemical structures depicted herein encompass all possible tautomeric forms of the illustrated compounds. Compounds may exist in unsolvated forms as well as solvated forms, including hydrated forms. Certain compounds may exist in multiple crystalline, co-crystalline, or amorphous forms. Compounds include pharmaceutically acceptable salts thereof, or pharmaceutically acceptable solvates of the free acid form of any of the foregoing, as well as crystalline forms of any of the foregoing.

"Disease" refers to a disease, disorder, condition, or symptom of any of the foregoing.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids and one or more protonable functional groups such as primary, secondary, or tertiary amines within the parent compound. Examples of suitable inorganic acids include hydrochloric acid, hydrobromic acid, sulfuric acid, nitric acid, phosphoric acid, and the like. A salt can be formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. A salt can be formed when one or more acidic protons present in the parent compound are replaced by a metal ion, e.g., an alkali metal ion, an alkaline earth ion, or an aluminum ion, or combinations thereof; or coordinates with an organic base such as ethanolamine, diethanolamine, triethanolamine, N-methylglucamine, and the like. A pharmaceutically acceptable salt can be the hydrochloride salt. A pharmaceutically acceptable salt can be the sodium salt. In compounds having two or more ionizable groups, a pharmaceutically acceptable salt can comprise one or more counterions, such as a bi-salt, for example, a dihydrochloride salt.

The term "pharmaceutically acceptable salt" includes hydrates and other solvates, as well as salts in crystalline or non-crystalline form. Where a particular pharmaceutically acceptable salt is disclosed, it is understood that the particular salt (e.g., a hydrochloride salt) is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound provided by the present disclosure or a pharmaceutically acceptable salt thereof and at least one pharmaceutically acceptable vehicle, with which the compound provided by the present disclosure, or a pharmaceutically acceptable salt thereof is administered to a patient. Pharmaceutically acceptable vehicles are known in the art.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by administering a compound provided by the present disclosure in a preventative fashion. The application of a therapeutic agent for preventing or prevention of a disease of disorder is known as 'prophylaxis.' Compounds provided by the present disclosure can provide superior prophylaxis because of lower long-term side effects over long time periods.

"A compound provided by the present disclosure" refers to a compound encompassed by Formula (1)-(2) and pharmaceutically salts thereof. In certain embodiments, a compound provided by the present disclosure can further include a compound encompassed by Formula (1)-(2), pharmaceutically salts, solvates, hydrates, and/or prodrugs of any of the foregoing.

Compounds provided by the present disclosure also include crystalline and amorphous forms of the compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

"Treating" or "treatment" of a disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter or manifestation that may or may not be discernible to the patient. "Treating" or "treatment" also refers to delaying the onset of the disease or delaying the onset of at least one or more symptoms thereof in a patient who may be exposed to or predisposed to a disease or disorder even though that patient does not yet experience or display symptoms of the disease.

"Therapeutically effective amount" refers to the amount of a compound that, when administered to a patient for treating a disease, or at least one of the clinical symptoms of a disease, is sufficient to affect such treatment of the disease or symptom thereof. A "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Vehicle" refers to a diluent, excipient, or carrier with which a compound is administered to a patient. A vehicle can be a pharmaceutically acceptable vehicle. Pharmaceutically acceptable vehicles are known in the art.

"Modulate" and "modulation" refer to a change in biological activity for a biological molecule such as, for example, a protein, gene, peptide, or antibody, where such change may relate to an increase in biological activity such as, for example, increased activity, agonism, activation, expression, upregulation, and/or increased expression, or decrease in biological activity such as, for example, decreased activity, antagonism, suppression, deactivation, downregulation, and/or decreased expression, for the biological molecule. For example, the compounds described herein can modulate such as inhibit ERK1/2. Compounds provided by the preset disclosure can selectively modulate, such as selectively inhibit ERK1/2 as compared to other proteins. Compounds provided by the present disclosure can selectively modulate such as selectively inhibit ERK1/2 as compared to other proteins.

Reference is now made in detail to certain compounds, compositions, and methods. The disclosed compounds, compositions, and methods are not intended to be limiting of the claims. To the contrary, the claims are intended to cover all alternatives, modifications, and equivalents.

ERK, a type of serine/threonine protein kinase, is a signal transduction protein that transmits mitogen signals. ERK is generally located in the cytoplasm, and upon activation, ERK enters the nucleus and regulates transcription factor activity and gene expression. Through artificial cloning and sequencing analysis, the ERK family has been shown to consist of ERK 1, 2, 3, 5 and 6. ERK1 and ERK2 are two important members of the MAPK/ERK pathway, with molecular weights of 44 and 42 kDa, respectively.

Multiple stimulants such as growth factors, cytokines, viruses, G-protein-coupled receptor ligands and oncogenes activate the ERK pathway. Key molecules in the ERKV/MAPK signaling pathway mainly include the small G proteins Ras and downstream Raf kinase, MEK1/2 and ERK1/2. Ras is the most conserved product encoded by the Ha-ras, Hi-ras and N-ras oncogenes of the ras gene family. Raf kinase is a product of the raf oncogene. MEK1 and MEK2 are rare dual-specificity kinases that can activate ERK through phosphorylation at two regulatory sites, Tyr 204/187 and Thr 202/185.

Compounds provided by the present disclosure are selective modulators of Extracellular Signal-Regulated Kinase ERK1/2. Pharmaceutical compositions provided by the present disclosure include compounds provided by the present disclosure. Compounds and pharmaceutical compositions provided by the present disclosure can be used to treat diseases in which the disease is capable of being treated by modulating ERK1/2.

Compounds provided by the present disclosure are function-selective ERK1/2 modulators and can be capable of inhibiting ASM cell proliferation, AP-1 activity, and mitigating multiple features of allergic asthma in a murine model.

A compound provided by the present disclosure can have the structure of Formula (1) or Formula (2):

(1)

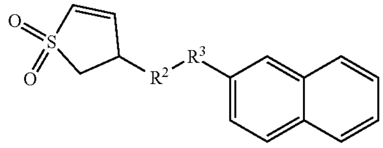

(2)

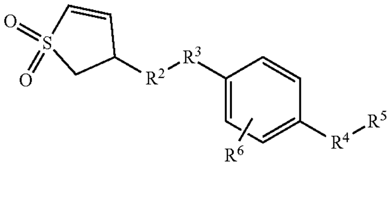

or can be a pharmaceutically acceptable salt of any of the foregoing, wherein, $R^2$ can be selected from —O—, —NH—, and —N(—$CH_3$)—;

$R^3$ can be selected from $C_{1-3}$ alkane-diyl and $C_{1-3}$ heteroalkane-diyl;

$R^4$ can be absent or is selected from $C_{1-2}$ alkane-diyl, $C_{1-2}$ heteroalkane-diyl, substituted $C_{1-2}$ alkane-diyl, and substituted $C_{1-2}$ heteroalkane-diyl;

$R^5$ can be selected from $C_{5-10}$ cycloalkyl, $C_{5-20}$ aryl, $C_{5-10}$ heterocycloalkyl, $C_{5-20}$ heteroaryl, substituted $C_{5-10}$ cycloalkyl, substituted $C_{5-20}$ aryl, substituted $C_{5-10}$ heterocycloalkyl, and substituted $C_{5-20}$ heteroaryl; and $R^6$ can be absent or is selected from $C_{1-3}$ alkyl and $C_{1-3}$ alkoxy.

In a compound of Formula (1) or Formula (2), the carbon atom bonded to $R^2$ can be in the (S)-configuration.

In a compound of Formula (1) or Formula (2), the carbon atom bonded to $R^2$ can be in the (R)-configuration.

In a compound of Formula (1) or Formula (2), $R^2$ can be —O—.

In a compound of Formula (1) or Formula (2), $R^2$ can be —NH—.

In a compound of Formula (1) or Formula (2), $R^2$ can be —N(—$CH_3$)—.

In a compound of Formula (1) or Formula (2), $R^3$ can be $C_{1-3}$ alkyl.

In a compound of Formula (1) or Formula (2), $R^3$ can be selected from methane-diyl and ethane-diyl.

In a compound of Formula (1) or Formula (2), $R^3$ can be $C_{1-3}$ heteroalkyl.

In a compound of Formula (1) or Formula (2), $R^3$ can be $C_{1-2}$ heteroalkyl.

In a compound of Formula (1) or Formula (2), $R^3$ can be $C_1$ heteroalkyl.

In a compound of Formula (1) or Formula (2), the $R^3$ heteroatomic group can be selected from —$SO_2$—, —CO—, and —NH—.

In a compound of Formula (1) or Formula (2), $R^3$ can be selected from —$CH_2$—, —$CH_2CH_2$—, —$SO_2$—, —$SO_2$—$CH_2$—, —$CH_2$—$SO_2$—, —CO—, —CO—$CH_2$—, —$CH_2$—CO—, —$CH_2$—NH—, and —CO—NH—.

In a compound of Formula (1) or Formula (2), $R^3$ can be —$SO_2$—.

In a compound of Formula (1) or Formula (2), $R^2$ can be selected from —O—, —NH—, and —N(—$CH_3$)—; and $R^3$ can be selected from —$CH_2$—, —$CH_2CH_2$—, —$SO_2$—, —$SO_2$—$CH_2$—, —$CH_2$—$SO_2$—, —CO—, —CO—$CH_2$—$CH_2$—CO—, —$CH_2$—NH—, and —CO—NH—.

In a compound of Formula (1) or Formula (2), $R^2$ can be —O—; and $R^3$ can be selected from —$CH_2$—, —$CH_2CH_2$—, —$SO_2$—, —$SO_2$—$CH_2$—, —$CH_2$—$SO_2$—, —CO—, —CO—$CH_2$—$CH_2$—CO—, —$CH_2$—NH—, and —CO—NH—.

In a compound of Formula (1) or Formula (2), $R^2$ can be selected from —O—, —NH—, and —N(—$CH_3$)—; and $R^3$ can be selected from —$CH_2$—, —$CH_2CH_2$—, —$SO_2$—, —$SO_2$—$CH_2$—, —$CH_2$—$SO_2$—, —CO—, —CO—$CH_2$— and —$CH_2$—CO—.

In a compound of Formula (1) or Formula (2), $R^2$ can be —O—; and $R^3$ can be selected from —$CH_2$—, —$CH_2CH_2$—, —$SO_2$—, —$SO_2$—$CH_2$—, —$CH_2$—$SO_2$—, —CO—, —CO—$CH_2$— and —$CH_2$—CO—.

In a compound of Formula (1) or Formula (2), $R^2$ can be —O— and $R^3$ can be —$SO_2$—.

A compound provided by the present disclosure can have the structure of Formula (2).

In a compound of Formula (2), $R^4$ can be absent.

In a compound of Formula (2), $R^4$ can be $C_{1-2}$ alkane-diyl.

In a compound of Formula (2), $R^4$ can be $C_{1-2}$ heteroalkane-diyl.

In a compound of Formula (2), $R^4$ can be substituted $C_{1-2}$ alkane-diyl.

In a compound of Formula (2), $R^4$ can be selected from —O—, —$CH_2$—, —O—$CH_2$—, —$CH_2$—O—, —C(O)—, —C(—OH)—, —S—, and —$S(O)_2$—.

In a compound of Formula (2), $R^5$ can be $C_{5-10}$ cycloalkyl.

In a compound of Formula (2), $R^5$ can be $C_{5-10}$ aryl.

In a compound of Formula (2), $R^5$ can be selected from phenyl and cyclohexyl.

In a compound of Formula (2), $R^5$ can be phenyl.

In a compound of Formula (2), $R^5$ can be cyclohexyl.

In a compound of Formula (2), $R^4$ can be selected from —O—, —$CH_2$—, —O—$CH_2$—, —$CH_2$—O—, —C(O)—, —C(—OH)—, —S—, and —$S(O)_2$—; and $R^5$ can be selected from phenyl and cyclohexyl.

In a compound of Formula (2), $R^6$ can be absent or can be selected from methyl and methoxy.

In a compound of Formula (2), $R^6$ can be absent.

In a compound of Formula (2), $R^6$ can be methyl.

In a compound of Formula (2), $R^6$ can be methoxy.

In a compound of Formula (2), $R^6$ can be bonded to the 2-position of the phenyl ring.

In a compound of Formula (2), $R^6$ can be bonded to the 3-position of the phenyl ring.

In a compound of Formula (2), $R^4$ can be selected from —O—, —$CH_2$—, —O—$CH_2$—, —$CH_2$—O—, —C(O)—, —C(—OH)—, —S—, and —$S(O)_2$—;

$R^5$ can be selected from phenyl and cyclohexyl; and $R^6$ can be absent.

In a compound of Formula (2), $R^4$ can be selected from —O—, —$CH_2$—, —O—$CH_2$—, —$CH_2$—O—, —C(O)—, —C(—OH)—, —S—, and —$S(O)_2$—;

$R^5$ is selected from phenyl and cyclohexyl; and $R^6$ can be selected from methyl and methoxy.

In a compound of Formula (2), $R^2$ can be —O—;

$R^3$ can be —$S(O)_2$—;

$R^4$ can be absent or can be selected from —O—, —$CH_2$—, —O—$CH_2$—, —$CH_2$—O—, —C(O)—, —C(—OH)—, —S—, and —$S(O)_2$—; and $R^5$ can be selected from phenyl and cyclohexyl.

In a compound of Formula (2), $R^2$ can be —O—;

$R^3$ can be —$S(O)_2$—;

$R^4$ can be absent or can be selected from —O—, —$CH_2$—, —O—$CH_2$—, —$CH_2$—O—, —C(O)—, —C(—OH)—, —S—, and —$S(O)_2$—;

$R^5$ can be selected from phenyl and cyclohexyl; and $R^6$ can be absent or can be selected from methyl and methoxy.

A compound provided by the present disclosure can have the structure of Formula (1).

A compound provided by the present disclosure can be selected from:

N-(1,1-dioxido-2,3-dihydrothiophen-3-yl)-N-methylnaphthalene-2-sulfonamide (2);

N-(1,1-dioxido-2,3-dihydrothiophen-3-yl)naphthalene-2-sulfonamide (3);

3-(naphthalen-2-ylmethoxy)-2,3-dihydrothiophene 1,1-dioxide (4);

3-([1,1'-biphenyl]-4-ylmethoxy)-2,3-dihydrothiophene 1,1-dioxide (5);

3-((4-phenoxybenzyl)oxy)-2,3-dihydrothiophene 1,1-dioxide (6);

3-(2-(naphthalen-2-yl)ethoxy)-2,3-dihydrothiophene 1,1-dioxide (7);

2-((1,1-dioxido-2,3-dihydrothiophen-3-yl)oxy)-1-(naphthalen-2-yl)ethan-1-one (8);

1-([1,1'-biphenyl]-4-yl)-2-((1,1-dioxido-2,3-dihydrothiophen-3-yl)oxy)ethan-1-one (9);

1,1-dioxido-2,3-dihydrothiophen-3-yl naphthalen-2-ylcarbamate (10);

1,1-dioxido-2,3-dihydrothiophen-3-yl [1,1'-biphenyl]-4-ylcarbamate (11);

1-(1,1-dioxido-2,3-dihydrothiophen-3-yl)-3-(naphthalen-2-yl)urea (12);

1-([1,1'-biphenyl]-4-yl)-3-(1,1-dioxido-2,3-dihydrothiophen-3-yl)urea (13);

N-(1,1-dioxido-2,3-dihydrothiophen-3-yl)-2-naphthamide (14);

N-(1,1-dioxido-2,3-dihydrothiophen-3-yl)-2-(naphthalen-2-yl)acetamide (15);

N-(1,1-dioxido-2,3-dihydrothiophen-3-yl)-N-methylnaphthalene-2-sulfonamide (16);

1,1-dioxido-2,3-dihydrothiophen-3-yl 4-phenoxybenzoate (23);

1,1-dioxido-2,3-dihydrothiophen-3-yl [1,1'-biphenyl]-4-carboxylate (24);

1,1-dioxido-2,3-dihydrothiophen-3-yl 3-phenoxybenzenesulfonate (25);

1,1-dioxido-2,3-dihydrothiophen-3-yl [1,1'-biphenyl]-3-sulfonate (26);

1,1-dioxido-2,3-dihydrothiophen-3-yl 4-(benzyloxy)benzenesulfonate (27);

1,1-dioxido-2,3-dihydrothiophen-3-yl 4-benzylbenzenesulfonate (28);

1,1-dioxido-2,3-dihydrothiophen-3-yl 4-(phenoxymethyl)benzenesulfonate (29);

1,1-dioxido-2,3-dihydrothiophen-3-yl [1,1'-biphenyl]-4-sulfonate (33);

1,1-dioxido-2,3-dihydrothiophen-3-yl 4-cyclohexylbenzenesulfonate (34);

1,1-dioxido-2,3-dihydrothiophen-3-yl 3-cyclohexylbenzenesulfonate (35);

1,1-dioxido-2,3-dihydrothiophen-3-yl 4-(cyclohexyloxy)benzenesulfonate (36);

1,1-dioxido-2,3-dihydrothiophen-3-yl 3-(cyclohexyloxy)benzenesulfonate (37);

1,1-dioxido-2,3-dihydrothiophen-3-yl 4-benzoylbenzenesulfonate (38);

1,1-dioxido-2,3-dihydrothiophen-3-yl 4-(hydroxy(phenyl)methyl)benzenesulfonate (39);

1,1-dioxido-2,3-dihydrothiophen-3-yl 2-methyl-4-phenoxybenzenesulfonate (40);

1,1-dioxido-2,3-dihydrothiophen-3-yl 2-methoxy-4-phenoxybenzenesulfonate (41);

1,1-dioxido-2,3-dihydrothiophen-3-yl 4-benzyl-3-methylbenzenesulfonate (42);

1,1-dioxido-2,3-dihydrothiophen-3-yl 3-methoxy-4-phenoxybenzenesulfonate (43);

1,1-dioxido-2,3-dihydrothiophen-3-yl 4-(phenylthio)benzenesulfonate (44);

1,1-dioxido-2,3-dihydrothiophen-3-yl 4-(phenylsulfonyl) benzenesulfonate (45); and a pharmaceutically acceptable salt of any of the foregoing.

A compound provided by the present disclosure can be selected from:

N-(1,1-dioxido-2,3-dihydrothiophen-3-yl)naphthalene-2-sulfonamide (3);

3-(naphthalen-2-ylmethoxy)-2,3-dihydrothiophene 1,1-dioxide (4);

3-([1,1'-biphenyl]-4-ylmethoxy)-2,3-dihydrothiophene 1,1-dioxide (5);

3-((4-phenoxybenzyl)oxy)-2,3-dihydrothiophene 1,1-dioxide (6);

3-(2-(naphthalen-2-yl)ethoxy)-2,3-dihydrothiophene 1,1-dioxide (7);

2-((1,1-dioxido-2,3-dihydrothiophen-3-yl)oxy)-1-(naphthalen-2-yl)ethan-1-one (8);

1-([1,1'-biphenyl]-4-yl)-2-((1,1-dioxido-2,3-dihydrothiophen-3-yl)oxy)ethan-1-one (9);

1,1-dioxido-2,3-dihydrothiophen-3-yl naphthalen-2-ylcarbamate (10);

1,1-dioxido-2,3-dihydrothiophen-3-yl [1,1'-biphenyl]-4-ylcarbamate (11);

N-(1,1-dioxido-2,3-dihydrothiophen-3-yl)-2-(naphthalen-2-yl)acetamide (15);

1,1-dioxido-2,3-dihydrothiophen-3-yl 4-phenoxybenzoate (23);

1,1-dioxido-2,3-dihydrothiophen-3-yl 3-phenoxybenzenesulfonate (25);

1,1-dioxido-2,3-dihydrothiophen-3-yl [1,1'-biphenyl]-3-sulfonate (26);

1,1-dioxido-2,3-dihydrothiophen-3-yl 4-(benzyloxy)benzenesulfonate (27);

1,1-dioxido-2,3-dihydrothiophen-3-yl 4-benzylbenzenesulfonate (28);

1,1-dioxido-2,3-dihydrothiophen-3-yl 4-(phenoxymethyl) benzenesulfonate (29);

1,1-dioxido-2,3-dihydrothiophen-3-yl [1,1'-biphenyl]-4-sulfonate (33);

1,1-dioxido-2,3-dihydrothiophen-3-yl 4-cyclohexylbenzenesulfonate (34);

1,1-dioxido-2,3-dihydrothiophen-3-yl 3-cyclohexylbenzenesulfonate (35);

1,1-dioxido-2,3-dihydrothiophen-3-yl 4-(cyclohexyloxy) benzenesulfonate (36);

1,1-dioxido-2,3-dihydrothiophen-3-yl 3-(cyclohexyloxy) benzenesulfonate (37);

1,1-dioxido-2,3-dihydrothiophen-3-yl 4-benzoylbenzenesulfonate (38);

1,1-dioxido-2,3-dihydrothiophen-3-yl 4-(hydroxy(phenyl) methyl)benzenesulfonate (39);

1,1-dioxido-2,3-dihydrothiophen-3-yl 2-methyl-4-phenoxybenzenesulfonate (40);

1,1-dioxido-2,3-dihydrothiophen-3-yl 2-methoxy-4-phenoxybenzenesulfonate (41);

1,1-dioxido-2,3-dihydrothiophen-3-yl 4-benzyl-3-methylbenzenesulfonate (42);

1,1-dioxido-2,3-dihydrothiophen-3-yl 3-methoxy-4-phenoxybenzenesulfonate (43);

1,1-dioxido-2,3-dihydrothiophen-3-yl 4-(phenylthio)benzenesulfonate (44);

1,1-dioxido-2,3-dihydrothiophen-3-yl 4-(phenylsulfonyl) benzenesulfonate (45); and a pharmaceutically acceptable salt of any of the foregoing.

A compound provided by the present disclosure can be selected from:

1,1-dioxido-2,3-dihydrothiophen-3-yl 3-phenoxybenzenesulfonate (25);

1,1-dioxido-2,3-dihydrothiophen-3-yl 4-benzoylbenzenesulfonate (38);

1,1-dioxido-2,3-dihydrothiophen-3-yl 2-methyl-4-phenoxybenzenesulfonate (40);

1,1-dioxido-2,3-dihydrothiophen-3-yl 2-methoxy-4-phenoxybenzenesulfonate (41);

1,1-dioxido-2,3-dihydrothiophen-3-yl 3-methoxy-4-phenoxybenzenesulfonate (43); and a pharmaceutically acceptable salt of any of the foregoing.

A compound provided by the present disclosure can be selected from:

N-(1,1-dioxido-2,3-dihydrothiophen-3-yl)-N-methylnaphthalene-2-sulfonamide (2);

N-(1,1-dioxido-2,3-dihydrothiophen-3-yl)naphthalene-2-sulfonamide (3);

3-(naphthalen-2-ylmethoxy)-2,3-dihydrothiophene 1,1-dioxide (4);

3-(2-(naphthalen-2-yl)ethoxy)-2,3-dihydrothiophene 1,1-dioxide (7);

2-((1,1-dioxido-2,3-dihydrothiophen-3-yl)oxy)-1-(naphthalen-2-yl)ethan-1-one (8);

1,1-dioxido-2,3-dihydrothiophen-3-yl naphthalen-2-ylcarbamate (10);

1-(1,1-dioxido-2,3-dihydrothiophen-3-yl)-3-(naphthalen-2-yl)urea (12);

N-(1,1-dioxido-2,3-dihydrothiophen-3-yl)-2-naphthamide (14);

N-(1,1-dioxido-2,3-dihydrothiophen-3-yl)-2-(naphthalen-2-yl)acetamide (15);

N-(1,1-dioxido-2,3-dihydrothiophen-3-yl)-N-methylnaphthalene-2-sulfonamide (16);

a pharmaceutically acceptable salt of any of the foregoing.

A compound provided by the present disclosure can be selected from:

3-([1,1'-biphenyl]-4-ylmethoxy)-2,3-dihydrothiophene 1,1-dioxide (5);

1-([1,1'-biphenyl]-4-yl)-2-((1,1-dioxido-2,3-dihydrothiophen-3-yl)oxy)ethan-1-one (9);

1-([1,1'-biphenyl]-4-yl)-3-(1,1-dioxido-2,3-dihydrothiophen-3-yl)urea (13);

1,1-dioxido-2,3-dihydrothiophen-3-yl [1,1'-biphenyl]-4-carboxylate (24);

1,1-dioxido-2,3-dihydrothiophen-3-yl [1,1'-biphenyl]-3-sulfonate (26);

1,1-dioxido-2,3-dihydrothiophen-3-yl [1,1'-biphenyl]-4-sulfonate (33);

1,1-dioxido-2,3-dihydrothiophen-3-yl 4-cyclohexylbenzenesulfonate (34);

1,1-dioxido-2,3-dihydrothiophen-3-yl 3-cyclohexylbenzenesulfonate (35);

a pharmaceutically acceptable salt of any of the foregoing.

A compound provided by the present disclosure can be selected from:

3-((4-phenoxybenzyl)oxy)-2,3-dihydrothiophene 1,1-dioxide (6);

1,1-dioxido-2,3-dihydrothiophen-3-yl [1,1'-biphenyl]-4-ylcarbamate (11);

1,1-dioxido-2,3-dihydrothiophen-3-yl 4-phenoxybenzoate (23);

1,1-dioxido-2,3-dihydrothiophen-3-yl 3-phenoxybenzenesulfonate (25);

1,1-dioxido-2,3-dihydrothiophen-3-yl 4-(benzyloxy)benzenesulfonate (27);

1,1-dioxido-2,3-dihydrothiophen-3-yl 4-benzylbenzenesulfonate (28);

1,1-dioxido-2,3-dihydrothiophen-3-yl 4-(phenoxymethyl) benzenesulfonate (29);

1,1-dioxido-2,3-dihydrothiophen-3-yl 4-(cyclohexyloxy) benzenesulfonate (36);

1,1-dioxido-2,3-dihydrothiophen-3-yl 3-(cyclohexyloxy) benzenesulfonate (37);

1,1-dioxido-2,3-dihydrothiophen-3-yl 4-benzoylbenzenesulfonate (38);

1,1-dioxido-2,3-dihydrothiophen-3-yl 4-(hydroxy(phenyl) methyl)benzenesulfonate (39);

1,1-dioxido-2,3-dihydrothiophen-3-yl 2-methyl-4-phenoxybenzenesulfonate (40);

1,1-dioxido-2,3-dihydrothiophen-3-yl 2-methoxy-4-phenoxybenzenesulfonate (41);

1,1-dioxido-2,3-dihydrothiophen-3-yl 4-benzyl-3-methylbenzenesulfonate (42);

1,1-dioxido-2,3-dihydrothiophen-3-yl 3-methoxy-4-phenoxybenzenesulfonate (43);

1,1-dioxido-2,3-dihydrothiophen-3-yl 4-(phenylthio)benzenesulfonate (44);

1,1-dioxido-2,3-dihydrothiophen-3-yl 4-(phenylsulfonyl) benzenesulfonate (45); and a pharmaceutically acceptable salt of any of the foregoing.

A compound provided by the present disclosure is not selected from:

1,1-dioxido-2,3-dihydrothiophen-3-yl naphthalene-2-sulfonate (1):

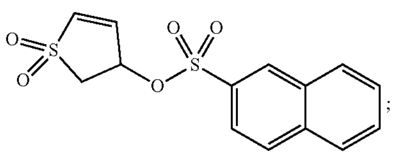 [SMILES: O=S1(=O)C=CC(OS(=O)(=O)c2ccc3ccccc3c2)C1]

;

1,1-dioxido-2,3-dihydrothiophen-3-yl [1,1'-biphenyl]-4-sulfonate (17):

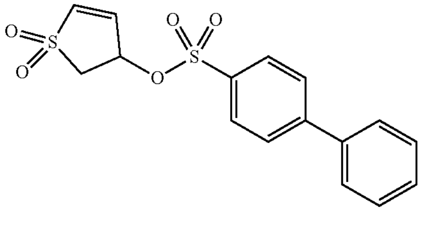

;

1,1-dioxido-2,3-dihydrothiophen-3-yl 4-phenoxybenzenesulfonate (18):

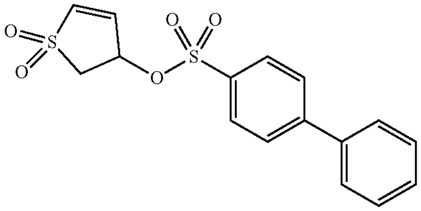

;

(S)-1,1-dioxido-2,3-dihydrothiophen-3-yl 4-phenoxybenzenesulfonate (21):

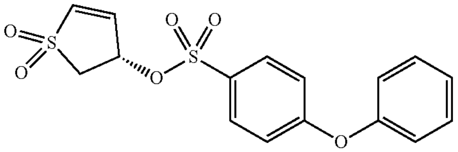

;

(R)-1,1-dioxido-2,3-dihydrothiophen-3-yl 4-phenoxybenzenesulfonate (22):

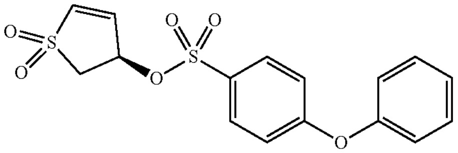

;

or a pharmaceutically acceptable salt of any of the foregoing.

A compound of Formula (1)-(2) can be the free base.

A compound of Formula (1)-(2) can be a solvate, a pharmaceutically acceptable salt, or a combination thereof.

In a compound of Formula (1)-(2), a pharmaceutically acceptable salt can be the hydrochloride salt.

A compound of Formula (1)-(2) can be a pharmaceutically acceptable salt of a compound of Formula (6), a hydrate thereof, or a solvate of any of the foregoing.

Compounds of Formula (1)-(2) can be synthesized adapting methods as described, for example, in Martinez et al., *Journal of Pharmacology and Experimental Therapeutics*, January 2021, Vol. 376, pages 84-97; and in U.S. Pat. No. 9,115,122.

Specific synthetic examples are provided in Examples 1-45.

A compound of Formula (1)-(2) can be an ERK1/2 modulator such as a selective ERK1/2 inhibitor and/or a modulator of ERK1/2 protein activity.

A compound of Formula (1)-(2) can be incorporated into pharmaceutical compositions to be administered to a patient by any appropriate route of administration including intradermal, intramuscular, intraperitoneal, intravenous, subcutaneous, intranasal, epidural, oral, peroral, sublingual, intracerebral, intravaginal, transdermal, rectal, inhalation, or topical. A pharmaceutical composition provided by the present disclosure can be an injectable formulation. A pharmaceutical composition provided by the present disclosure can be injectable intravenous formulation. A pharmaceutical composition provided by the present disclosure can be an oral formulation. An oral formulation can be an oral dosage form. A pharmaceutical composition can be formulated for intravenous administration or for subcutaneous administration.

A pharmaceutical composition provided by the present disclosure can comprise a therapeutically effective amount of a compound of Formula (1)-(2) together with a suitable amount of one or more pharmaceutically acceptable vehicles so as to provide a composition for proper administration to a patient. Suitable pharmaceutical vehicles and methods of preparing pharmaceutical compositions are described in the art.

Assessing single patient response to therapy and qualifying a patient for optimal therapy are among the greatest challenges of modern healthcare and motivate trends in personalized medicine. A compound of Formula (1)-(2) can have target selectivity, for example, for certain cancers and immune cells expressing ERK1/2. A compound of Formula (1)-(2) radiolabeled for positron emission tomography (PET) or Single Photon Emission Computed Tomography (SPECT) can be used to predict the targeting of the treatment based on a single-study, case-by-case patient analysis thus excluding patients that are expected not to benefit from treatment. PET/SPECT scans using a compound of Formula (1)-(2), once correlated to the concentration can provide a three-dimensional distribution map, which can then be used for macroscopic dose calculations.

A compound of Formula (1)-(2) and/or pharmaceutical composition thereof can generally be used in an amount effective to achieve an intended purpose. For use to treat a disease such as cancer, an autoimmune disease or an inflammatory disease, a compound of Formula (1)-(2) and/or pharmaceutical composition thereof, may be administered or applied in a therapeutically effective amount.

The amount of a compound of Formula (1)-(2) and/or pharmaceutical that will be effective in the treatment of a particular disorder or condition can depend in part on the nature of the disorder or condition, and can be determined by standard clinical techniques known in the art. In addition, in vitro or in vivo assays may optionally be employed to help identify optimal dosage ranges. The amount of a compound of Formula (1)-(2), and/or pharmaceutical composition of any of the foregoing administered can depend on, among other factors, the patient being treated, the weight of the patient, the severity of the affliction, the manner of administration and the judgment of the prescribing physician.

A compound of Formula (1)-(2) can be assayed in vitro and in vivo, for the desired therapeutic activity, prior to use in humans. For example, in vitro assays may be used to determine whether administration of a specific compound or a combination of compounds is preferred. The compounds can also be demonstrated to be effective and safe using animal model systems.

A therapeutically effective dose of a compound of Formula (1)-(2) and/or pharmaceutical composition of any of the foregoing can provide therapeutic benefit without causing substantial toxicity. Toxicity of a compound of Formula (1)-(2) and/or a pharmaceutical composition thereof may be determined using standard pharmaceutical procedures known in the art. A dose ratio between toxic and therapeutic effect is the therapeutic index. A compound of Formula (1)-(2) and/or pharmaceutical composition of any of the foregoing exhibits a particularly high therapeutic index in treating a disease or disorder. A dose of a compound of Formula (1)-(2) or a pharmaceutical composition thereof can be within a range of circulating concentration that includes an effective dose with minimal toxicity.

Compounds and pharmaceutical compositions provided by the present disclosure can be included in a kit that can be used to administer the compound to a patient for therapeutic purposes. A kit can include a pharmaceutical composition comprising a compound provided by the present disclosure suitable for administration to a patient and instructions for administering the pharmaceutical composition to the patient. The kit can be suitable, for example, for treating cancer, for treating an autoimmune disease, or for treating an inflammatory disease. A kit for use in treating cancer, for treating an autoimmune disease, or for treating an inflammatory disease can comprise a compound or a pharmaceutical composition provided by the present disclosure, and instructions for administering the compound to a patient.

Compounds and pharmaceutical compositions provided by the present disclosure can be included, for example, in a container, package, sachet, or dispenser together with instructions for administration.

Instructions supplied with a kit may be printed and/or supplied, for example, as an electronic-readable medium, a video cassette, an audiotape, a flash memory device, or may be published on an internet web site or distributed to a patient and/or health care provider as an electronic communication.

Compounds and pharmaceutical compositions provided by the present disclosure can be used to treat a disease in a patient.

Compounds and pharmaceutical compositions provided by the present disclosure can be used to treat a disease in which the etiology of the disease is associated with up-regulation and/or downregulation of ERK1/2.

Methods provided by the present disclosure include treating a disease in a patient comprising administering to a patient in need of such treatment a therapeutically effective amount of a compound or composition provided by the present disclosure, wherein the disease is capable of being treated by modulating or inhibiting ERK1/2.

Asthma is an obstructive pulmonary disease that impacts the quality of life for over 230 million people worldwide. Airway inflammation is fundamental to asthma pathology and chronic inflammation leads to airway remodeling (AR) characterized by structural and secretory changes in multiple lung cell types. There are currently no effective pharmacological anti-asthma therapies that prevent or reverse AR although AR is directly correlated with reduced pulmonary function and morbidity in asthma. Significant strides have been made in developing immunologics for asthma treatment, however, the heterogeneity of inflammation (Th2 high vs. low) among asthmatics significantly limits the use of biologicals in asthma. Thus, identification of key downstream effectors including transcriptional regulators and rational design of drugs targeting these effectors will help facilitate new treatment for asthma. The Activator Protein-1 (AP-1) transcription factor complex is one such central regulator at which mediators of asthma pathology converge. Also, AP-1 cooperates with other transcription factors, including NF—KB and STAT proteins to mediate inflammatory responses in asthma.

The mitogen-activated protein kinases (MAPK), which include the extracellular signal-regulated kinases (ERK1/2), c-Jun N-terminal kinases (JNK1/2), and the p38 MAPK family, are major regulators of AP-1 proteins. It has been well documented that ERK1/2 signaling is perturbed in asthma and is a predominant regulator of airway smooth muscle (ASM) cell proliferation, a key component of AR. As such, modulating or inhibiting ERK1/2 is an attractive therapeutic approach to mitigate AR. However, ERK1/2 regulates many substrates, some of which are essential for normal cell function and may have pro- or anti-asthmatic functions. Thus, ATP-competitive compounds developed to modulate or inhibit ERK1/2 can block all kinase activity and have limited efficacy due to off-target effects, toxicity, and the invariable induction of drug resistance.

Compounds provided by the present disclosure can target ERK1/2 interactions with substrates in the AP-1 complex and inhibits AP-1 activity in multiple cell lines, including ASM cells. Structural studies demonstrate the requirement for the formation of a covalent adduct with a cysteine residue (C252) that is part of a unique ERK1/2 docking site that mediates interactions with AP-1 complex proteins. Importantly, C252 is unique to ERK1/2 and analogous cysteines are not found on other major MAP kinases such as ERK5, p38α/β, or JNK1/2. Compounds provided by the present disclosure can potentially modulate or inhibit PDGF-induced proliferation and secretory function of ASM cells and mitigates AR and other pathological features including airway inflammation and hyperresponsiveness in a mouse model of asthma.

ERK1/2 kinases are associated with the pathogenesis of many human diseases including, for example, cancer, rheumatoid arthritis, cardiovascular disease, multiple sclerosis, inflammatory bowel disease, chronic obstructive pulmonary disease (COPD), asthma, acute respiratory distress syndrome (ARDS), and acute lung injury (ALI). Among the many important biological processes regulated by ERK1/2, regulation of endothelial and epithelial barrier function, leukocyte trafficking, and cytokine expression are central to the pathogenesis of acute and chronic inflammatory disorders.

Methods provided by the present disclosure include methods of treating a disease in a patient comprising administering to a patient in need thereof a therapeutically effective amount of a compound or pharmaceutical composition provided by the present disclosure, wherein the disease is selected from cancer, an inflammatory disease, an autoimmune disease, and a pulmonary disease.

Methods provided by the present disclosure include methods of treating a disease in a patient comprising administering to a patient in need thereof a therapeutically effective amount of a compound or pharmaceutical composition provided by the present disclosure, wherein the disease is selected from acute coronary syndrome, acute lung injury, acute respiratory distress syndrome (ARDS), Alzheimer's disease, asthma, a cardiovascular disease, chronic obstructive pulmonary disease (COPD), asthma, inflammatory bowel disease, major depressive disorder, multiple sclerosis, neuropathic pain, and rheumatoid arthritis.

Compounds and pharmaceutical compositions provided by the present disclosure may be used for treating cancer in a patient. The cancer can be, for example, a solid tumor or a metastasis.

Methods provided by the present disclosure include methods of treating cancer in a patient comprising administering to a patient in need thereof a therapeutically effective amount of a compound or pharmaceutical composition provided by the present disclosure.

Examples of suitable cancers include acoustic neuroma, adenocarcinoma, angiosarcoma, astrocytoma, basal cell carcinoma, bile duct carcinoma, bladder carcinoma, brain cancer, breast cancer, bronchogenic carcinoma, cervical cancer, chordoma, choriocarcinoma, colon cancer, colorectal cancer, craniopharyngioma, cystadenocarcinoma, embryonal carcinoma, endotheliocarcinoma, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendotheliosarcoma, lymphangiosarcoma, medullary carcinoma, medulloblastoma, melanoma, meningioma, mesothelioma, myxosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rhabdomyosarcoma, rectal cancer, renal cell carcinoma, retinoblastoma, sarcoma, sebaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilm's tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, and Hodgkin's disease.

Examples of suitable cancers include pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, or retinoblastoma. A cancer can be acoustic neuroma, adenocarcinoma, angiosarcoma, astrocytoma, basal cell carcinoma, bile duct carcinoma, bladder carcinoma, brain cancer, breast cancer, bronchogenic carcinoma, cervical cancer, chordoma, choriocarcinoma, colon cancer, colorectal cancer, craniopharyngioma, cystadenocarcinoma, embryonal carcinoma, endotheliocarcinoma, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendotheliosarcoma, lymphangiosarcoma, medullary carcinoma, medulloblastoma, melanoma, meningioma, mesothelioma, myxosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rhabdomyosarcoma, rectal cancer, renal cell carcinoma, retinoblastoma, sarcoma, sebaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilms tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, Hodgkin's disease, multiple myeloma, non-Hodgkin's lymphoma, polycythemia vera, or Waldenstrom macroglobulinemia.

Compounds and pharmaceutical compositions provided by the present disclosure can be used to treat, for example, one or more of the following cancers: acute lymphoblastic leukemia, acute myeloid leukemia, adrenocortical carcinoma, appendix cancer, astrocytoma, atypical teratoid/rhabdoid tumor, basal cell carcinoma (nonmelanoma), B-cell lymphoma, bladder cancer, bone cancer, brain and spinal cord tumors, brain stem cancer, brain tumor, breast cancer, bronchial tumors, Burkitt lymphoma, carcinoid tumor, carcinoma of head and neck, central nervous system embryonal tumors, cerebellar astrocytoma, cerebral astrocytoma/malignant glioma, cervical cancer, chordoma, chronic lymphocytic leukemia, chronic myelogenous leukemia, colorectal cancer, craniopharyngioma, cutaneous T-cell lymphoma, desmoplastic small round cell tumor, ductal carcinoma, dye cancer, endocrine pancreas tumors (islet cell tumors), endometrial cancer, ependymoblastoma, esophageal cancer, esthesioneuroblastoma, Ewing family of tumors, extracranial germ cell tumor, extrahepatic bile duct cancer, gallbladder cancer, gastric cancer, gastrointestinal carcinoid tumor, gastrointestinal stromal tumor, gestational trophoblastic tumor, glioblastoma, glioma, hairy cell leukemia, head and neck cancer, heart cancer, hematopoetic tumors of the lymphoid lineage, hepatocellular cancer, Hodgkin lymphoma, hypopharyngeal cancer, hypothalamic and visual pathway glioma, IDs-related lymphoma, intraocular melanoma, islet cell tumors, Kaposi sarcoma, kidney cancer, Langerhans cell histiocytosis, laryngeal cancer, leukemia, lip and oral cavity cancer, male breast cancer, malignant fibrous histiocytoma, malignant germ cell tumors, malignant mesothelioma, medulloblastoma, melanoma, Merkel cell carcinoma, mesothelioma, mouth cancer, multiple endocrine neoplasia syndrome, multiple myeloma, mycosis fungoides, myelodysplastic, myeloproliferative neoplasms, nasal cavity and paranasal sinus cancer, nasopharyngeal cancer, neuroblastoma, non-Hodgkin lymphoma, non-small cell lung cancer, oral cancer, oropharyngeal cancer, osteosarcoma, ovarian cancer, ovarian epithelial cancer, ovarian germ cell tumor, ovarian low malignant potential tumor, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pineal parenchymal tumors, pineoblastoma and supratentorial primitive neuroectodermal tumors, pituitary tumor, plasma cell neoplasm/multiple myeloma, pleuropulmonary blastoma, pregnancy and breast cancer, primary central nervous system lymphoma, primary liver cancer, primary metastatic squamous neck cancer with occult, prostate cancer, rectal cancer, renal cell cancer, renal pelvis and ureter, respiratory tract carcinoma, retinoblastoma, rhabdomyosarcoma, salivary gland cancer, sarcoma, Sézary syndrome, skin cancer, small intestine cancer, soft tissue sarcoma, squamous cell carcinoma (nonmelanoma), stomach cancer, supratentorial primitive neuroectodermal tumors, T-cell lymphoma, testicular cancer, throat cancer, thymoma and thymic carcinoma, thyroid cancer, transitional cell cancer, urethral cancer, uterine sarcoma, vaginal cancer, visual pathway and hypothalamic glioma, vulvar cancer, Waldenström macroglobulinemia, Wilms tumor, and systemic and central metastases of any of the foregoing.

Methods provided by the present disclosure include methods of treating cancer, where the cancer is selected from breast cancer and melanoma.

Methods provided by the present disclosure include methods of treating an inflammatory disease in a patient comprising administering to a patient in need thereof a therapeutically effective amount of a compound or pharmaceutical composition provided by the present disclosure.

Examples of inflammatory diseases include allergy, Alzheimer's disease, anemia, ankylosing spondylitis, arthritis, atherosclerosis, asthma, autism, arthritis, carpal tunnel syndrome, celiac disease, colitis, Crohn's disease, congestive heart failure, dermatitis, diabetes, diverticulitis, eczema, fibromyalgia, fibrosis, gall bladder disease gastroesophageal reflux disease, Hashimoto's thyroiditis, heart attack, hepatitis, irritable bowel syndrome, kidney failure, lupus, multiple sclerosis, nephritis, neuropathy, pancreatitis, Parkinson's disease, psoriasis, polymyalgia rheumatica, rheumatoid arthritis, scleroderma, stroke, surgical complications, and ulcerative colitis.

Methods provided by the present disclosure include methods of treating an inflammatory disease in a patient, where the inflammatory disease is selected from, for example, acute respiratory distress syndrome, focal segmental glomerulonephritis, atherosclerosis/acute coronary syndrome, chronic obstructive pulmonary disease, asthma, inflammatory bowel disease, Crohn's disease, psoriasis, lupus, multiple sclerosis, inflammation in hypercholesteremia, pain, diabetes including Type 1 diabetes and Type 2 diabetes, and rheumatoid arthritis.

Methods provided by the present disclosure include methods of treating an autoimmune disease in a patient comprising administering to a patient in need thereof a therapeutically effective amount of a compound or pharmaceutical composition provided by the present disclosure.

A compound or a pharmaceutical composition provided by the present disclosure can be useful in treating autoimmune diseases. Autoimmune diseases can be defined as human diseases in which the immune system attacks its own proteins, cells, and/or tissues. A comprehensive listing and review of autoimmune diseases can be found, for example, in *The Autoimmune Diseases*, Rose and Mackay, 2014, Academic Press.

Examples of autoimmune diseases include Addison's disease, agammaglobulinemia, alopecia areata, amyloidosis, ankylosing spondylitis, anti-GBM/anti-TBN nephritis, antiphospholipid syndrome, autoimmune angioedema, autoimmune dysautonomia, autoimmune encephalomyelitis, autoimmune hepatitis, autoimmune inner ear disease, autoimmune myocarditis, autoimmune pancreatitis, autoimmune retinopathy, autoimmune urticaria, axonal and neuronal neuropathy, Balo disease, Bechet's disease, benign mucosal pemphigoid, bullous pemphigoid, Castleman disease, celiac disease, Chagas disease, chronic inflammatory demyelinating polyneuropathy, chronic recurrent multifocal osteomyelitis, Churg-Strauss, cicatricial pemphigoid, Cogan' syndrome, cold agglutinin disease, congenital heart block, Coxcackie myocarditis, CREST syndrome, Crohn's disease, dermatitis herpetiformis, dermatomyositis, Devic's disease, discoid lupus, Dressler's syndrome, endometriosis, eosinophilic esophagitis, eosinophilic fasciitis, erythema nodosum, essential mixed cryoglobulinemia, Evans syndrome, fibromyalgia, fibrosing alveolitis, giant cell arteritis, giant cell myocarditis, glomerulonephritis, Goodpasture's syndrome, granulomatosis with polyangiitis, Graves' disease, Gullain-Barre syndrome, Hashimoto's thyroiditis, hemolytic anemia, Henoch-Schoenlein purpura, herpes gestationis or pemphigoid gestationis, hypogammaglobulinemia, IgA nephropathy, IgG4-related sclerosing disease, immune thrombocytopenic purpura, inclusion body myositis, interstitial cystitis, juvenile arthritis, juvenile diabetes, juvenile myositis, Kawasaki disease, Lambert-Eaton syndrome, leukocytoclastic vasculitis, lichen planus, lichen sclerosis, ligneous conjunctivitis, linear IgA disease, lupus, Lyme disease chronic, Meniere's diseases, microscopic polyangiitis, mixed connective tissue disease, Mooren's ulcer, Mucha Habermann disease, multiple sclerosis, myasthenia gravis, myositis, narcolepsy, neuromyelitis, optica, neutropenia, ocular cicatricial pemphigoid, optic neuritis, palindromic rheumatism, PANDAS, paraneoplastic cerebellar degeneration, paroxysmal nocturnal hemoglobinuria, Parry Romberg syndrome, pars planitis, Parsonnage-Turner syndrome, pemphigus, peripheral neuropathy, perivenous encephalomyelitis, pernicious anemia, POEMS syndrome, polyarteritis nodosa, polyglandular syndromes, polymyalgia rheumatica, polymyositis, postmyocardial infarction syndrome, post-pericardiotomy syndrome, primary biliary cirrhosis, primary sclerosing cholangitis, progesterone dermatitis, psoriasis, psoriatic arthritis, pure red cell aplasia, pyoderma gangrenosum, Raynaud's phenomenon, reactive arthritis, reflex sympathetic dystrophy, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome, subacute bacterial endocarditis, Susac's syndrome, sympathetic ophthalmia, Takayasu's arteritis, temporal arteritis, thrombocytopenic purpura, Tolosa-Hunt syndrome, transverse myelitis, type 1 diabetes, ulcerative colitis, undifferentiated connective tissue disease, uveitis, vasculitis, vitiligo, and Wegener's granulomatosis.

A compound or a pharmaceutical composition provided by the present disclosure can be used to treat autoimmune disorders such as, for example, lupus, graft-versus-host disease, hepatitis C-induced vasculitis, Type I diabetes, multiple sclerosis, spontaneous loss of pregnancy, an atopic disease, and an inflammatory bowel disease.

A compound or a pharmaceutical composition provided by the present disclosure can be administered with one or more additional therapeutic agents for treating an autoimmune disease. A compound of Formula (1)-(2) or a pharmaceutical composition thereof may be administered in conjunction with one or more immunosuppressants including, for example, corticosteroids such as prednisone, budesonide, and prednisolone; Janus kinase inhibitors such as tofacitinib; calcineurin inhibitors such as cyclosporine and tacrolimus; mTOR inhibitors such as sirolimus and everolimus; IMDH inhibitors such as azathioprine, leflunomide, and mycophenolate; biologics such as abatacept adalimumab, anakinra, certolizumab, etanercept, golimumab, infliximab, ixekizumab, natalizumab, rituximab, secukinumab, tocilizumab, ustekinumab, and vedolizumab; and monoclonal antibodies such as basiliximab and daclizumab.

Methods provided by the present disclosure include methods of treating a disease in a patient comprising administering to a patient in need thereof a therapeutically effective amount of a compound or pharmaceutical composition provided by the present disclosure, wherein the disease is selected from acute coronary syndrome, acute lung injury, acute respiratory distress syndrome (ARDS), Alzheimer's disease, asthma, a cardiovascular disease, chronic obstructive pulmonary disease (COPD), inflammatory bowel disease, major depressive disorder, multiple sclerosis, neuropathic pain, and rheumatoid arthritis.

A compound or a pharmaceutical composition provided by the present disclosure can be administered with one or more additional therapeutic agents for treating an age-related disease such as hearing loss, muscle regeneration, and Werner's syndrome.

Methods provided by the present disclosure include methods of treating a disease in a patient comprising administering to a patient in need thereof a therapeutically effective amount of a compound or pharmaceutical composition provided by the present disclosure, wherein the disease is an age-related disease such as, for example, hearing loss, muscle degeneration, Werner's syndrome, cellular aging, or Alzheimer's disease.

Methods provided by the present disclosure include methods of treating a disease in a patient comprising administering to a patient in need thereof a therapeutically effective amount of a compound or pharmaceutical composition provided by the present disclosure, wherein the disease is selected from sudden idiopathic hearing loss, drug induced hearing loss, age-related hearing loss, and Duchenne muscular dystrophy.

Methods provided by the present disclosure include methods of treating a viral disease in a patient comprising administering to a patient in need thereof a therapeutically effective amount of a compound or pharmaceutical composition provided by the present disclosure. A viral disease can be SARS-CoV-19 and SARS-CoV-2.

The amount of a compound of Formula (1)-(2), or a pharmaceutical composition thereof that will be effective in the treatment of a disease can depend, at least in part, on the nature of the disease, and may be determined by standard clinical techniques known in the art. In addition, in vitro or in vivo assays may be employed to help identify optimal dosing ranges. Dosing regimens and dosing intervals may also be determined by methods known to those skilled in the art. The amount of a compound of Formula (1)-(2) administered may depend on, among other factors, the patient being treated, the weight of the patient, the severity of the disease, the route of administration, and the judgment of the prescribing physician.

For systemic administration, a therapeutically effective dose may be estimated initially from in vitro assays. Initial doses may also be estimated from in vivo data, e.g., animal models, using techniques that are known in the art. Such information may be used to more accurately determine useful doses in humans. One having ordinary skill in the art may optimize administration to humans based on animal data.

A dose of a compound of Formula (1)-(2) and appropriate dosing intervals may be selected to maintain a sustained therapeutically effective concentration of a compound of Formula (1)-(2) in the blood of a patient, and in certain embodiments, without exceeding a minimum adverse concentration.

A pharmaceutical composition comprising a compound of Formula (1)-(2) may be administered, for example once per week, every 2 weeks, every 3 weeks, every 4 weeks, every 5 weeks, or every 6 weeks. Dosing may be provided alone or in combination with other drugs and may continue as long as required for effective treatment of the disease. Dosing may also be undertaken using continuous or semi-continuous administration over a period of time. Dosing includes administering a pharmaceutical composition to a mammal, such as a human, in a fed or fasted state.

A pharmaceutical composition may be administered in a single dosage form or in multiple dosage forms or as a continuous or an accumulated dose over a period of time. When multiple dosage forms are used the amount of a compound of Formula (1)-(2) contained within each of the multiple dosage forms may be the same or different.

Suitable daily dosage ranges for administration can range, for example, from about 2 μg to about 200 mg of a compound of Formula (1)-(2) per kilogram body weight.

Suitable daily dosage ranges for administration may range, for example, from about 1 μg to about 50 mg of a compound of Formula (1)-(2) per square meter ($m^2$) of body surface.

A compound of Formula (1)-(2) may be administered to treat cancer in a patient in an amount, for example, from 0.001 mg/day to 100 mg/day, or in any other appropriate daily dose. A dose can be, for example, from 0.01 μg/kg body weight/week to 100 μg/kg body weight/week or any other suitable dose.

A pharmaceutical composition comprising a compound of Formula (1)-(2) may be administered to treat cancer in a patient so as to provide a therapeutically effective concentration of a compound of Formula (1)-(2) in the blood or plasma of the patient. A therapeutically effective concentration of a compound of a compound of Formula (1)-(2) in the blood of a patient can be, for example, from 0.01 μg/L to 1,000 μg/L, from 0.1 μg/L to 500 μg/L, from 1 μg/L to 250 μg/L, or from about 10 μg/L to about 100 μg/L. A therapeutically effective concentration of a compound of Formula (1)-(2) in the blood of a patient can be, for example, at least 0.01 μg/L, at least 0.1 μg/L, at least 1 μg/L, at least about 10 μg/L, or at least 100 μg/L. A therapeutically effective concentration of a compound of Formula (1)-(2) in the blood of a patient can be, for example, less than an amount that causes unacceptable adverse effects including adverse effects to homeostasis. A therapeutically effective concentration of a compound of Formula (1)-(2) in the blood of a patient can be an amount sufficient to restore and/or maintain homeostasis in the patient.

Pharmaceutical compositions provided by the present disclosure may be administered to treat a disease in a patient so as to provide a therapeutically effective concentration of a compound of Formula (1)-(2) in the blood of a patient for a period of time such as, for example, for 4 hours, 8 hours, 12 hours, 16 hours, 20 hours, 1 day, or 2 days.

The amount of a compound of Formula (1)-(2) administered may vary during a treatment regimen.

Pharmaceutical compositions provided by the present disclosure may further comprise one or more pharmaceutically active compounds in addition to a compound of Formula (1)-(2). Such compounds may be provided, for example, to treat the cancer being treated with the compound of Formula (1)-(2) or to treat a disease, disorder, or condition other than the cancer being treated with the compound of Formula (1)-(2), to treat a side-effect caused by administering the compound of Formula (1)-(2), to augment the efficacy of the compound of Formula (1)-(2), and/or to modulate the activity of the compound of Formula (1)-(2).

A compound of Formula (1)-(2) may be administered in combination with at least one other therapeutic agent. A compound of Formula (1)-(2) may be administered to a patient together with another compound for treating cancer in the patient. The at least one other therapeutic agent can be a second, different compound of Formula (1)-(2). A compound of Formula (1)-(2) and the at least one other therapeutic agent may act additively or, and in certain embodiments, synergistically with another compound of Formula (1)-(2). The at least one additional therapeutic agent may be included in the same pharmaceutical composition or vehicle comprising the compound of Formula (1)-(2) or may be in a separate pharmaceutical composition or vehicle. Accordingly, methods provided by the present disclosure further include, in addition to administering a compound of Formula (1)-(2), administering one or more therapeutic agents effective for treating cancer or a different disease, disorder or condition than cancer. Methods provided by the present disclosure include administration of a compound of Formula (1)-(2) and one or more other therapeutic agents provided that the combined administration does not inhibit the therapeutic efficacy of the compound of Formula (1)-(2) and/or does not produce adverse combination effects.

A pharmaceutical composition comprising a compound of Formula (1)-(2) may be administered concurrently with the administration of another therapeutic agent, which may be part of the same pharmaceutical composition as, or in a different pharmaceutical composition than that comprising a compound of Formula (1)-(2). A compound of Formula (1)-(2) may be administered prior or subsequent to administration of another therapeutic agent. In certain combination therapies, the combination therapy may comprise alternating between administering a compound of Formula (1)-(2) and a composition comprising another therapeutic agent, e.g., to minimize adverse drug effects associated with a particular drug. When a compound of Formula (1)-(2) is administered concurrently with another therapeutic agent that potentially may produce an adverse drug effect including, for example, toxicity, the other therapeutic agent may be administered at a dose that falls below the threshold at which the adverse drug reaction is elicited.

A pharmaceutical composition comprising a compound of Formula (1)-(2) provided by the present disclosure may be administered with one or more substances, for example, to enhance, modulate and/or control release, bioavailability, therapeutic efficacy, therapeutic potency, and/or stability, of the compound of Formula (1)-(2). For example, a pharmaceutical composition comprising a compound of Formula (1)-(2) can be co-administered with an active agent having pharmacological effects that enhance the therapeutic efficacy of the compound of Formula (1)-(2).

A compound of Formula (1)-(2), or a pharmaceutical composition thereof may be administered in conjunction with an agent known or believed to be effective in treating a disease such as cancer, an autoimmune disease, or an inflammatory disease in a patient, such as the same disease being treated with the compound of Formula (1)-(2).

A compound of Formula (1)-(2), or a pharmaceutical composition thereof may be administered in conjunction with an agent known or believed to interfere with cell proliferation.

A compound of Formula (1)-(2), or a pharmaceutical composition thereof may be administered in conjunction with an agent known or believed to interfere with cellular metabolism, to be an anti-metabolite, to interfere with RNA transcription, to interfere with RNA translation, to interfere with cellular protein synthesis, to interfere with synthesis of precursors for DNA synthesis and replication, to interfere with purine synthesis, to interfere with nucleoside synthesis, to interact with mTOR, to be an mTOR inhibitor, to interfere with cell cycle checkpoints.

A compound of Formula (1)-(2) or a pharmaceutical composition thereof may be administered in conjunction with a checkpoint inhibitor including a CTLA-4 inhibitor such as ipilimumab, a PD-1 inhibitor such as pembrolizumab and nivolumab, and/or a PD-LI inhibitor such as atezolizumab, avelumab, and durvalumab. A compound of Formula (1)-(2) or a pharmaceutical composition thereof may be administered in conjunction with an immunomodulator such as CD137/4-1BB, CD27, GIYR, and/or OC40.

A compound of Formula (1)-(2) or a pharmaceutical composition thereof may be administered in conjunction with an agent known or believed to be cytotoxic, to cause DNA damage, to cause cell cycle arrest, or to cause mitotic catastrophe.

A compound of Formula (1)-(2) or a pharmaceutical composition thereof may be administered in conjunction with an agent known or believed to modulate glutathione concentration, to modulate glutathione concentration within cells, to decrease glutathione concentration within cells, to reduce glutathione uptake into cells, to reduce glutathione synthesis, or to reduce glutathione synthesis within cells.

A compound of Formula (1)-(2) or a pharmaceutical composition thereof may be administered in conjunction with an agent known or believed to interfere with neovascularization, to reduce neovascularization, or to promote neovascularization.

A compound of Formula (1)-(2) or a pharmaceutical composition thereof may be administered in conjunction with an agent known or believed to interfere with hormone homeostasis, to interfere with hormone synthesis, to interfere with hormone receptor binding, or to interfere with hormone signal transduction.

A compound of Formula (1)-(2) or a pharmaceutical composition thereof may be administered in conjunction with an agent known or believed to interfere with growth factor homeostasis, to interfere with growth factor receptor expression, to interfere with growth factor binding to growth factor receptors, to interfere with growth factor receptor signal transduction, to interfere with the Hedgehog (Hh) signaling, to inhibit the Hedgehog pathway signaling, to inhibit ALK (anaplastic lymphoma kinase) pathway signaling, or to inhibit the non-homologous end joining (NHEJ) pathway.

A compound of Formula (1)-(2) or a pharmaceutical composition thereof may be administered in conjunction with one or more agents known or believed to be a VEGFR (vascular endothelial growth factor receptor) inhibitor, a RTK (receptor tyrosine kinase) inhibitor, a sodium channel current blocker, aFAK (focal adhesion kinase) inhibitor, a GLI (glioma-associated oncogene) inhibitor, a GLI1 inhibitor, a GLI2 inhibitor, a GLI3 inhibitor, a MAPK (mitogen-activated protein kinase) inhibitor, a MAPK/ERK pathway (also known as Ras-Raf-MEK-ERK pathways) inhibitor, a MEK1 inhibitor, a MEK2 inhibitor, a MEK5 inhibitor, a MEK5/ERK5 inhibitor, aRTA (renal tubular acidosis) inhibitor, a ALK (anaplastic lymphoma kinase) inhibitor, Aa LK kinase inhibitor, a nuclear translocation inhibitor, a PORCN (porcupine) inhibitor, a 5-ARI (5α-reductase inhibitor), topoisomerase inhibitor, a Ras (rat sarcoma) inhibitor, a K-ras inhibitor, a CERK (ceramide kinase) inhibitor, a PKB (protein kinase B, also known as AKT) inhibitor, a AKT1 inhibitor, EZH2 (enhancer of zeste homolog 2) inhibitor, a BET (bromodomain and extraterminal domain motif) inhibitor, a SYK (spleen tyrosine kinase) inhibitor, JAK (janus kinase) inhibitors, a SYK/JAK inhibitor, a IDO (indoleamine-pyrrole 2,3-dioxygenase) inhibitor, a IDO1 inhibitor, a RXR (retinoic X receptors) activating agent, a selective RXR activating agent, a p-glycoprotein inhibitor, a ERK inhibitor, a PI3K (phosphatidylinositol-4,5-bisphosphate 3-kinase) inhibitor, a BRD (bromodomain-containing protein) inhibitor, a BRD2 inhibitor, a BRD3 inhibitor, a BRD4 inhibitor, a BRDT (bromodomain testis-specific protein) inhibitor, a reverse transcriptase inhibitor, a NRT (nucleoside analog reverse-transcriptase) inhibitor, a PIM (proviral integrations of Moloney virus) inhibitor, a EGFR (epidermal growth factor receptor) inhibitor, a photosensitizer, a radiosensitizer, a ROS (proto-oncogene, receptor tyrosine kinase) inhibitor, a ROS1 (proto-oncogene 1) inhibitor, a CK (casein kinase) inhibitor, a CK2 inhibitor, a Bcr-Abl (breakpoint cluster region—Abelson proto-oncogene) tyrosine-kinase inhibitor such as dasatinib, a microtubule stabilizing agent, a microtubule depolymerization/disassembly inhibitor, a DNA intercalator, an androgen receptor antagonist, a chemoprotective agents, a HDAC (histone deacetylase) inhibitor, a DPP (dipeptidyl peptidase) inhibitor, a DPP-4 inhibitor, BTK (Bruton's tyrosine kinase) inhibitor, a kinase inhibitor such as imatinib, a tyrosine kinase inhibitor such as nilotinib, a ARP (poly (ADP-ribose) polymerase) inhibitor, a CDK (cyclin-dependent kinase) inhibitor, a CDK4 inhibitor, a CDK6 inhibitor, a CDK4/6 inhibitor, a HIF1α (hypoxia-inducible factor 1-α) inhibitor, a DNA ligase inhibitor, a DNA ligase IV inhibitor, a NHEJ (non-homologous end joining) inhibitor, a DNA ligase IV, a NHEJ inhibitor and a RAF inhibitor, a TKI and a RAF inhibitor, a TKI and RAF inhibitor such as sorafenib, a PDT (photodynamic therapy) sensitizer, an ATR (ataxia telangiectasia- and Rad3-related protein kinase) inhibitor, or a combination of any of the foregoing.

A compound of Formula (1)-(2) or a pharmaceutical composition thereof may be administered in conjunction with one or more chemotherapeutic agents, such as, for example, a VEGFR inhibitor such as fruquintinib, motesanib/AMG-706, vatalanib; a RTK inhibitor such as ponatinib; a sodium channel blocker such as GS967; a FAK inhibitor such as TAE226; a GLI1 and GLI2 inhibitor such as GANT61, a MEK inhibitor such as binimetinib; a RTA inhibitor such as linifanib; an ALK inhibitor such as brigstinib; bromopyruvic acid; a DNA alkylating agent such as thiotepa; nuclear translocations factors such as JSH-23; a PORCn inhibitor such as Wnt-C59; a 5α-reductase inhibitor such as dutasteride; a topoisomerase inhibitor such as carubicin; a RAS inhibitor such as Kobe0065; a CerK inhibitor such as NVP-231; an AKT inhibitor such as uprosertib; a EZH2 inhibitor such as GSK-503; a BET bromodomain inhibitor such as OTX015; a MEK5/ERK5 inhibitor such as BIX02189; a Syl/JAK inhibitor such as cerdulatinib; an IDO1 inhibitor such as NLG919; a retinoic X receptor activating agent such as bexsrotene; a PGP inhibitor such as acotiamide or actotiamide HCl; an Erk inhibitor such SCH772984; a PI3K inhibitor such as gedatolisib; a JAK inhibitor such as ruxolitinib; an AKT inhibitor such as afuresertib or afuresertib HCl; an ALK1 inhibitor such as ceritinib; an HDAC inhibitor such as abexinostat; a DPP inhibitor such as oamarigliptin; an EGFR inhibitor such as gefittinib; an EZH2 inhibitor such as GSK126; a BTK inhibitor such as ibrutinib; a kinase inhibitor such as imatinin HCl; an IDO inhibitor such as INCB024360; a DNA crosslinker such as mitomycin C; a tyrosine kinase inhibitor such as nilotinib, a PARP inhibitor such as olaparib; a tubulin stabilization promoter such as paclitaxel; a CDK4/6 inhibitor such as palbociclib; a RTK inhibitor such as sunitinib; a PDT sensitizer such as tslsporfin; a p-glycoprotein inhibitor such as tariquidar; an ATR inhibitor such as VE-822; an HDAC inhibitor such as PCI-24781; a DPP inhibitor such as omarigliptin; an EGFR inhibitor such as gefinib; an EZH2 inhibitor such as GSK126; a BTK inhibitor such as irbrutinib; an IDO inhibitor such as INCB024360; or a combination of any of the foregoing.

A compound of Formula (1)-(2) or a pharmaceutical composition thereof may be administered in conjunction with another chemotherapeutic agent, such as, for example, N-acetyl cysteine (NAC), adriamycin, alemtuzumab, amifostine, arsenic trioxide, ascorbic acid, bendamustine, bevacizumab, bortezomib, busulfan, buthionine sulfoxime, carfilzomib, carmustine, clofarabine, cyclophosphamide, cyclosporine, cytarabine, dasatinib, datinomycin, defibrotide, dexamethasone, docetaxel, doxorubicin, etoposide, filgrastim, floxuridine, fludarabine, gemcitabine, interferon alpha, ipilimumab, lenalidomide, leucovorin, melphalan, mycofenolate mofetil, paclitaxel, palifermin, panobinostat, pegfilrastim, prednisolone, prednisone, revlimid, rituximab, sirolimus, sodium 2-mercaptoethane sulfonate (MESNA), sodium thiosulfate, tacrolimus, temozolomide, thalidomide, thioguanine, thiotepa, topotecan, velcade, or a combination of any of the foregoing.

A compound of Formula (1)-(2) or a pharmaceutical compositions thereof can be used in combination therapy with other chemotherapeutic agents including one or more antimetabolites such as folic acid analogs; pyrimidine analogs such as fluorouracil, floxuridine, and cytosine arabinoside; purine analogs such as mercaptopurine, thiogunaine, and pentostatin; natural products such as vinblastine, vincristine, etoposide, tertiposide, dactinomycin, daunorubicin, doxorubicin, bleomycin, mithamycin, mitomycin C, L-asparaginase, and interferon alpha; platinum coordination complexes such as cis- platinum, and carboplatin; mitoxantrone; hydroxyurea; procarbazine; hormones and antagonists such as prednisone, hydroxyprogesterone caproate, medroxyprogesterone acetate, megestrol acetate, diethylstilbestrol, ethinyl estradiol, tamoxifen, testosterone propionate, fluoxymesterone, flutamide, and leuprolide, anti-angiogenesis agents or inhibitors such as angiostatin, retinoic acids, paclitaxel, estradiol derivatives, and thiazolopyrimidine derivatives; apoptosis prevention agents; triptolide; colchicine; luliconazole; and radiation therapy.

A compound of Formula (1)-(2) or a pharmaceutical composition thereof may be co-administered with a compound that inhibits DNA repair such as, for example, O6-benzylguanine (O6-BG).

A compound of Formula (1)-(2) or a pharmaceutical composition thereof may be administered in conjunction with one or more chemotherapeutic agents, such as, for example, abarelix, abiraterone, abiraterone acetate, n-acetyl cysteine, aclarubicin hydrochloride, adriamycin, adenine, afatinib, afatinib dimaleate, alemtuzumab, alendronate sodium, alitretinoin, allopurinol sodium, altretamine, amifostine, aminoglutethimide, aminolevulinic acid, amrubicin, amsacrine, anastrozole, angiostatin, apremilast, aprepitant, arsenic trioxide, ascorbic acid, 1-asparaginase, azacitidine, azathioprine sodium, bazedoxifene (serm), belinostat, bendamustine hcl, O6-benzylguanine, bevacizumab, bexarotene, bicalutamide, biricodar, bleomycin sulfate, bortezomib, bosutinib, brivudine, buserelin, busulfan, buthionine sulfoxime, cabazitaxel, cabozantinib, capecitabine, carboplatin, carboquone, carfilzomib, carmofur, carmustine, ceritinib, chlorambucil, cisplatin, cladribine, clodronate disodium, clofarabine, crizotinib, cyclophosphamide, cyclosporine, cytarabine, cytosine arabinoside, dabrafenib, dacarbazine, dactinomycin, dasatinib, datinomycin, daunorubicin, decitabine, defribrotide, degarelix acetate, dexamethasone, dexrazoxane hydrochloride, diaziquone, diethyl stilbestrol, docetaxel, doxifluridine, doxorubicin hydrochloride, doxorubicin free base, dromostanolone propionate, dutasteride, eltrombopag, enzalutamide, epirubicin hydrochloride, eribulin mesylate, erlotinib hydrochloride, estramustine phosphate sodium, ethinyl estradiol, etoposide phosphate, etoposide, everolimus, exemestane, fentanyl, filgrastim, fingolimod, floxuridine, fludarabine phosphate, fluorouracil, fluoxymesterone, flutamide, formestane, formylmelphalan, fosaprepitant, fotemustine, fulvestrant, gefitinib, gemcitabine hydrochloride, gemcitabine free base, glutathione, glyciphosphoramide, glyfosfin, goserelin acetate, granisetron hydrochloride, heptaplatin, hexyl 5-aminolevulinate, histrelin acetate, hydroxyprogesterone caproate, hydroxyurea, ibandronate sodium, ibrutinib, icotinib, idarubicin HCl, idelalisib, idoxuridine, ifosfamide, interferon alpha, imatinib mesylate, imiquimod, ingenol mebutate, ipilimumab, irinotecan hydrochloride, ixabepilone, lanreotide acetate, lapatinib free base, lapatinib ditosylate, lasofoxifene, lenalidomide, letrozole, leucovorin calcium, leuprolide acetate, levamisole hydrochloride, levoleucovorin calcium, iobenguane, lobaplatin, lomustine, maropitant, masoprocol, mechlorethamine hydrochloride, megestrol acetate, medroxyprogesterone acetate, melphalan hydrochloride, mercaptopurine, mercaptoethane sulfonate sodium, methotrexate, methoxsalen, methyl aminolevulinate, methylene blue, methylisoindigotin, mifamurtide, miltefosine, miriplatin, mithamycin, mitobronitol, mitomycin C, mitotane, mitoxantrone hydrochloride, mycophenolate mofetil, nabiximols, nafarelin, nandrolone, nedaplatin, nelarabine, netupitant, nilotinib, nilutamide, nimustine, nintedanib, nocodazole, octreotide, olaparib, omacetaxine mepesuccinate, ondansetron hydrochloride, oxaliplatin, paclitaxel, palbociclib, palifermin, palonosetron hydrochloride, pamidronate disodium, panobinostat, pasireotide, pazopanib hydrochloride, pegfilrastim, pemetrexed disodium, pentostatin, peplomycin, pipobroman, pirarubicin, plerixafor, plicamycin, pomalidomide, ponatinib, porfimer sodium, porfiromycin, pralatrexate, prednimustine, prednisolone, prednisone, procarbazine hydrochloride, quinagolide hydrochloride, raloxifene, raltitrexed, radotinib, ranimustine, retinoic acids, revlimide, rituxinab, romidepsin, ruxolitinib, ruxolitinib phosphate, semustine, sirolimus, sodium thiosulfate, sorafenib free base, sorafenib tosylate, streptozocin, sufentanil, sunitinib, tacrolimus, talaporfin sodium, tamibarotene, tamoxifen citrate, tapentadol, temoporfin, temozolomide, temsirolimus, teniposide, teriflunomide, tertiposide, testolactone, testosterone propionate, thalidomide, thioguanine, thiotepa, thymalfasin, toceranib phosphate, topotecan hydrochloride, toremifene citrate, trabectedin, trametinib, tretinoin, trilostane, triptorelin, tropisetron, uramustine, valrubicin, vandetanib, vedotin, vemurafenib, verteporfin, vinblastine, vincristine sulfate, vincristine free base, vindesine, vinorelbine tartrate, vorinostat, and zoledronic acid.

A compound of Formula (1)-(2) or a pharmaceutical composition thereof may be administered in conjunction with one or more chemotherapeutic agents such as, for example, abemaciclib, abiraterone acetate, ABVD, ABVE, ABVE-PC, AC, acalabrutinib, AC-T, ADE, ado-trastuzumab emtansine, afatinib dimaleate, aldesleukin, alectinib, alemtuzumab, alpelisib, amifostine, aminolevulinic acid hydrochloride, anastrozole, apalutamide, aprepitant, arsenic trioxide, asparaginase *Erwinia chrysanthemi*, atezolizumab, avelumab, axicabtagene ciloleucel, axitinib, azacitidine, BEACOPP, belinostat, bendamustine hydrochloride, BEP, bevacizumab, bexarotene, bicalutamide, binimetinib, bleomycin sulfate, blinatumomab, bortezomib, bosutinib, brentuximab vedotin, brigatinib, BuMel, busulfan, cabazitaxel, cabozantinib-s-malate, CAF, calaspargase pegol-mknl, capecitabine, caplacizumab-yhdp, CAPOX, carboplatin, carboplatin-taxol, carfilzomib, carmustine, carmustine implant, CEM, cemiplimab-rwlc, ceritinib, cetuximab, CEV, chlorambucil, chlorambucil-prednisone, CHOP, cisplatin, cladribine, clofarabine, CMF, cobimetinib, copanlisib hydrochloride, COPDAC, COPP, COPP-ABV, crizotinib, CVP, cyclophosphamide, cytarabine, cytarabine liposome, dabrafenib mesylate, dacarbazine, dacomitinib, dactinomycin, daratumumab, darbepoetin a, dasatinib, daunorubicin hydrochloride, daunorubicin hydrochloride and cytarabine liposome, decitabine, defibrotide sodium, degarelix, denileukin diftitox, denosumab, dexamethasone, dexrazoxane hydrochloride, dinutuximab, docetaxel, doxorubicin hydrochloride, doxorubicin hydrochloride liposome, durvalumab, duvelisib, elotuzumab, eltrombopag olamine, emapalumab-lzsg, enasidenib mesylate, encorafenib, enzalutamide, epirubicin hydrochloride, EPOCH, epoetin a, erdafitinib, eribulin mesylate, erlotinib hydrochloride, etoposide, etoposide phosphate, everolimus, exemestane, fec, filgrastim, fludarabine phosphate, fluorouracil injection, fluorouracil—topical, flutamide, folfiri, folfiri-bevacizumab, folfiri-cetuximab, folfirinox, folfox, fostamatinib disodium, FU-LV, fulvestrant, gefitinib, gemcitabine hydrochloride, gemcitabine-cisplatin, gemcitabine-oxaliplatin, gemtuzumab ozogamicin, gilteritinib fumarate, glasdegib maleate, glucarpidase, goserelin acetate, granisetron, HPV bivalent vaccine, HPV bivalent vaccine, recombinant HPV nonavalent vaccine, HPV nonavalent vaccine, recombinant, HPV quadrivalent vaccine, HPV uadrivalent vaccine recombinant, hydroxyurea, hyper-CVAD, ibritumomab tiuxetan, ibrutinib, ICE, idarubicin hydrochloride, idelalisib, ifosfamide, imatinib mesylate, imiquimod, inotuzumab ozogamicin, interferon α-2b recombinant, iobenguane $^{131}$I, ipilimumab, irinotecan hydrochloride, irinotecan hydrochloride liposome, ivosidenib, ixabepilone, ixazomib citrate, JEB, lanreotide acetate, lapatinib ditosylate, larotrectinib sulfate, lenalidomide, lenvatinib mesylate, letrozole, leucovorin calcium, leuprolide acetate, lomustine, lorlatinib, lutetium Lu 177-dotatate, mechlorethamine hydrochloride, megestrol acetate, melphalan, melphalan hydrochloride, mercaptopurine, mesna, methotrexate, methylnaltrexone bromide, midostaurin, mitomycin c, mitoxantrone hydrochloride, mogamulizumab-kpkc, moxetumomab pasudotox-tdfk, MVAC, necitumumab, nelarabine, neratinib maleate, netupitant and palonosetron hydrochloride, nilotinib, nilutamide, niraparib tosylate monohydrate, nivolumab, obinutuzumab, OEPA, ofatumumab, OFF, olaparib, olaratumab, omacetaxine mepesuccinate, ondansetron hydrochloride, OPPA, osimertinib mesylate, oxaliplatin, paclitaxel, paclitaxel albumin-stabilized nanoparticle formulation, PAD, palbociclib, palifermin, palonosetron hydrochloride, palonosetron hydrochloride and netupitant, pamidronate disodium, panitumumab, panobinostat, pazopanib hydrochloride, PCV, PEB, pegaspargase, pegfilgrastim, peginterferon α-2b, pembrolizumab, pemetrexed disodium, pertuzumab, plerixafor, polatuzumab vedotin-piiq, pomalidomide, ponatinib hydrochloride, pralatrexate, prednisone, procarbazine hydrochloride, propranolol hydrochloride, radium 223 dichloride, raloxifene hydrochloride, ramucirumab, rasburicase, ravulizumab-cwvz, R—CHOP, R—CVP, recombinant HPV bivalent vaccine, recombinant HPV nonavalent vaccine, recombinant HPV quadrivalent vaccine, recombinant interferon α-2b, regorafenib, R-EPOCH, ribociclib, R-ICE, rituximab, rituximab and hyaluronidase human, rolapitant hydrochloride, romidepsin, romiplostim, rucaparib camsylate, ruxolitinib phosphate, siltuximab, sipuleucel-t, sonidegib, sorafenib tosylate, STANFORD V, sunitinib malate, TAC, tagraxofusp-erzs, talazoparib tosylate, talc, talimogene laherparepvec, tamoxifen citrate, temozolomide, temsirolimus, thalidomide, thioguanine, thiotepa, tisagenlecleucel, tocilizumab, topotecan hydrochloride, toremifene, TPF, trabectedin, trametinib, trastuzumab, trastuzumab and hyaluronidase-oysk, trifluridine and tipiracil hydrochloride, uridine triacetate, VAC, Valrubicin, VAMP, vandetanib, VeIP, vemurafenib, venetoclax, vinblastine sulfate, vincristine sulfate liposome, vinorelbine tartrate, vip, vismodegib, vorinostat, XELIRI, XELOX, Ziv-aflibercept, zoledronic acid, and combinations of any of the foregoing.

A compound provided by the present disclosure or a pharmaceutically acceptable salt thereof or a pharmaceutical composition thereof can be administered to a patient in conjunction with another compound known to be useful for treating cancer, an inflammatory disease, an autoimmune disease, or other disease being treated using a compound of Formula (1)-(2).

ASPECTS OF THE INVENTION

The invention is further defined by one or more of the following aspects.

Aspect 1. A compound having the structure of Formula (1) or the structure of Formula (2):

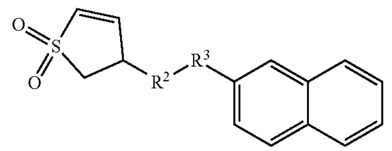

(1)

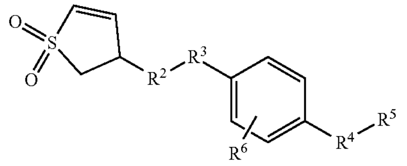

(2)

or is a pharmaceutically acceptable salt thereof, wherein, $R^2$ is selected from —O—, —NH—, and —N(—CH$_3$)—;

$R^3$ is selected from $C_{1-3}$ alkane-diyl and $C_{1-3}$ heteroalkane-diyl;

$R^4$ is absent or is selected from $C_{1-2}$ alkane-diyl, $C_{1-2}$ heteroalkane-diyl, substituted $C_{1-2}$ alkane-diyl, and substituted $C_{1-2}$ heteroalkane-diyl;

$R^5$ is selected from $C_{5-10}$ cycloalkyl, $C_{5-20}$ aryl, $C_{5-10}$ heterocycloalkyl, $C_{5-20}$ heteroaryl, substituted $C_{5-10}$ cycloalkyl, substituted $C_{5-20}$ aryl, substituted $C_{5-10}$ heterocycloalkyl, and substituted $C_{5-20}$ heteroaryl; and $R^6$ is absent or is selected from $C_{1-3}$ alkyl and $C_{1-3}$ alkoxy.

Aspect 2. The compound of aspect 1, wherein the carbon atom bonded to $R^2$ is in the (S)-configuration.

Aspect 3. The compound of aspect 1, wherein the carbon atom bonded to $R^2$ is in the (R)-configuration.

Aspect 4. The compound of any one of aspects 1 to 3, wherein $R^2$ is —O—.

Aspect 5. The compound of any one of aspects 1 to 3, wherein $R^2$ is —NH—.

Aspect 6. The compound of any one of aspects 1 to 3, wherein $R^2$ is —N(—CH$_3$)—.

Aspect 7. The compound of any one of aspects 1 to 6, wherein $R^3$ is $C_{1-3}$ alkane-diyl.

Aspect 8. The compound of any one of aspects 1 to 6, wherein $R^3$ is selected from methane-diyl and ethane-diyl.

Aspect 9. The compound of any one of aspects 1 to 6, wherein $R^3$ is $C_{1-3}$ heteroalkane-diyl.

Aspect 10. The compound of any one of aspects 1 to 6, wherein $R^3$ is $C_{1-2}$ heteroalkane-diyl.

Aspect 11. The compound of any one of aspects 1 to 6, wherein $R^3$ is $C_1$ heteroalkane-diyl.

Aspect 12. The compound of any one of aspects 1 to 6, wherein the $R^3$ heteroatomic group is selected from $—SO_2—$, —CO—, and —NH—.

Aspect 13. The compound of any one of aspects 1 to 6, wherein $R^3$ is selected from $—CH_2—$, $—CH_2CH_2—$, $—SO_2—$, $—SO_2—CH_2—$, $—CH_2—SO_2—$, —CO—, $—CO—CH_2—$, $—CH_2—CO—$, $—CH_2—NH—$, and —CO—NH—.

Aspect 14. The compound of any one of aspects 1 to 6, wherein $R^3$ is $—SO_2—$.

Aspect 15. The compound of any one of aspects 1 to 3, wherein $R^2$ is —O— and $R^3$ is $—SO_2—$.

Aspect 16. The compound of any one of aspects 1 to 15, wherein the compound has the structure of Formula (2).

Aspect 17. The compound of aspect 16, wherein $R^4$ is absent.

Aspect 18. The compound of aspect 16, wherein $R^4$ is $C_{1-2}$ alkane-diyl.

Aspect 19. The compound of aspect 16, wherein $R^4$ is $C_{1-2}$ heteroalkane-diyl.

Aspect 20. The compound of aspect 16, wherein $R^4$ is substituted $C_{1-2}$ alkane-diyl.

Aspect 21. The compound of aspect 16, wherein $R^4$ is selected from —O—, $—CH_2—$, $—O—CH_2—$, $—CH_2—O—$, —C(O)—, —C(—OH)—, —S—, and $—S(O)_2—$.

Aspect 22. The compound of any one of aspects 16 to 21, wherein $R^5$ is $C_{5-10}$ cycloalkyl.

Aspect 23. The compound of any one of aspects 16 to 21, wherein $R^5$ is $C_{5-10}$ aryl.

Aspect 24. The compound of any one of aspects 16 to 21, wherein $R^5$ is selected from phenyl and cyclohexyl.

Aspect 25. The compound of any one of aspects 16 to 21, wherein $R^5$ is phenyl.

Aspect 26. The compound of any one of aspects 16 to 21, wherein $R^5$ is cyclohexyl.

Aspect 27. The compound of any one of aspects 16 to 26, wherein $R^6$ is absent or is selected from methyl and methoxy.

Aspect 28. The compound of any one of aspects 16 to 26, wherein $R^6$ is absent.

Aspect 29. The compound of any one of aspects 16 to 26, wherein $R^6$ is methyl.

Aspect 30. The compound of any one of aspects 16 to 26, wherein $R^6$ is methoxy.

Aspect 31. The compound of any one of aspects 16 to 30, wherein $R^6$ is bonded to the 2-position of the phenyl ring.

Aspect 32. The compound of any one of aspects 16 to 30, wherein $R^6$ is bonded to the 3-position of the phenyl ring.

Aspect 33. The compound of aspect 16, wherein, $R^4$ is a bond or is —O—, $—CH_2—$, $—O—CH_2—$, $—CH_2—O—$, —C(O)—, —C(—OH)—, —S—, and $—S(O)_2—$; and $R^5$ is selected from phenyl and cyclohexyl.

Aspect 34. The compound of aspect 16, wherein, $R^2$ is —O—;

$R^3$ is $—S(O)_2—$;

$R^4$ is absent or is selected from —O—, $—CH_2—$, $—O—CH_2—$, $—CH_2—O—$, —C(O)—, —C(—OH)—, —S—, and $—S(O)_2—$;

$R^5$ is selected from phenyl and cyclohexyl; and $R^6$ is absent or is selected from methyl and methoxy.

Aspect 35. The compound of any one of aspects 1 to 15, wherein the compound has the structure of Formula (1).

Aspect 36. The compound of aspect 1, wherein the compound is selected from:

N-(1,1-dioxido-2,3-dihydrothiophen-3-yl)-N-methylnaphthalene-2-sulfonamide (2);

N-(1,1-dioxido-2,3-dihydrothiophen-3-yl)naphthalene-2-sulfonamide (3);

3-(naphthalen-2-ylmethoxy)-2,3-dihydrothiophene 1,1-dioxide (4);

3-([1,1'-biphenyl]-4-ylmethoxy)-2,3-dihydrothiophene 1,1-dioxide (5);

3-((4-phenoxybenzyl)oxy)-2,3-dihydrothiophene 1,1-dioxide (6);

3-(2-(naphthalen-2-yl)ethoxy)-2,3-dihydrothiophene 1,1-dioxide (7);

2-((1,1-dioxido-2,3-dihydrothiophen-3-yl)oxy)-1-(naphthalen-2-yl)ethan-1-one (8);

1-([1,1'-biphenyl]-4-yl)-2-((1,1-dioxido-2,3-dihydrothiophen-3-yl)oxy)ethan-1-one (9);

1,1-dioxido-2,3-dihydrothiophen-3-yl naphthalen-2-ylcarbamate (10);

1,1-dioxido-2,3-dihydrothiophen-3-yl [1,1'-biphenyl]-4-ylcarbamate (11);

1-(1,1-dioxido-2,3-dihydrothiophen-3-yl)-3-(naphthalen-2-yl)urea (12);

N-(1,1-dioxido-2,3-dihydrothiophen-3-yl)-2-naphthamide (14);

N-(1,1-dioxido-2,3-dihydrothiophen-3-yl)-2-(naphthalen-2-yl)acetamide (15);

N-(1,1-dioxido-2,3-dihydrothiophen-3-yl)-N-methylnaphthalene-2-sulfonamide (16);

1,1-dioxido-2,3-dihydrothiophen-3-yl 4-phenoxybenzoate (23);

1,1-dioxido-2,3-dihydrothiophen-3-yl [1,1'-biphenyl]-4-carboxylate (24);

1,1-dioxido-2,3-dihydrothiophen-3-yl 3-phenoxybenzenesulfonate (25);

1,1-dioxido-2,3-dihydrothiophen-3-yl [1,1'-biphenyl]-3-sulfonate (26);

1,1-dioxido-2,3-dihydrothiophen-3-yl 4-(benzyloxy)benzenesulfonate (27);

1,1-dioxido-2,3-dihydrothiophen-3-yl 4-benzylbenzenesulfonate (28);

1,1-dioxido-2,3-dihydrothiophen-3-yl 4-(phenoxymethyl)benzenesulfonate (29);

1,1-dioxido-2,3-dihydrothiophen-3-yl [1,1'-biphenyl]-4-sulfonate (33);

1,1-dioxido-2,3-dihydrothiophen-3-yl 4-cyclohexylbenzenesulfonate (34);

1,1-dioxido-2,3-dihydrothiophen-3-yl 3-cyclohexylbenzenesulfonate (35);

1,1-dioxido-2,3-dihydrothiophen-3-yl 4-(cyclohexyloxy)benzenesulfonate (36);

1,1-dioxido-2,3-dihydrothiophen-3-yl 3-(cyclohexyloxy)benzenesulfonate (37);

1,1-dioxido-2,3-dihydrothiophen-3-yl 4-benzoylbenzenesulfonate (38);

1,1-dioxido-2,3-dihydrothiophen-3-yl 4-(hydroxy(phenyl)methyl)benzenesulfonate (39);

1,1-dioxido-2,3-dihydrothiophen-3-yl 2-methyl-4-phenoxybenzenesulfonate (40);

1,1-dioxido-2,3-dihydrothiophen-3-yl 2-methoxy-4-phenoxybenzenesulfonate (41);

1,1-dioxido-2,3-dihydrothiophen-3-yl 4-benzyl-3-methylbenzenesulfonate (42);

1,1-dioxido-2,3-dihydrothiophen-3-yl 3-methoxy-4-phenoxybenzenesulfonate (43);

1,1-dioxido-2,3-dihydrothiophen-3-yl 4-(phenylthio)benzenesulfonate (44);

1,1-dioxido-2,3-dihydrothiophen-3-yl 4-(phenylsulfonyl) benzenesulfonate (45); and a pharmaceutically acceptable salt of any of the foregoing.

Aspect 37. The compound of aspect 1, wherein the compound is selected from:

N-(1,1-dioxido-2,3-dihydrothiophen-3-yl)naphthalene-2-sulfonamide (3);

3-(naphthalen-2-ylmethoxy)-2,3-dihydrothiophene 1,1-dioxide (4);

3-([1,1'-biphenyl]-4-ylmethoxy)-2,3-dihydrothiophene 1,1-dioxide (5);

3-((4-phenoxybenzyl)oxy)-2,3-dihydrothiophene 1,1-dioxide (6);

3-(2-(naphthalen-2-yl)ethoxy)-2,3-dihydrothiophene 1,1-dioxide (7);

2-((1,1-dioxido-2,3-dihydrothiophen-3-yl)oxy)-1-(naphthalen-2-yl)ethan-1-one (8);

1-([1,1'-biphenyl]-4-yl)-2-((1,1-dioxido-2,3-dihydrothiophen-3-yl)oxy)ethan-1-one (9);

1,1-dioxido-2,3-dihydrothiophen-3-yl naphthalen-2-ylcarbamate (10);

1,1-dioxido-2,3-dihydrothiophen-3-yl [1,1'-biphenyl]-4-ylcarbamate (11);

N-(1,1-dioxido-2,3-dihydrothiophen-3-yl)-2-(naphthalen-2-yl)acetamide (15);

1,1-dioxido-2,3-dihydrothiophen-3-yl 4-phenoxybenzoate (23);

1,1-dioxido-2,3-dihydrothiophen-3-yl 3-phenoxybenzenesulfonate (25);

1,1-dioxido-2,3-dihydrothiophen-3-yl [1,1'-biphenyl]-3-sulfonate (26);

1,1-dioxido-2,3-dihydrothiophen-3-yl 4-(benzyloxy)benzenesulfonate 1935;

1,1-dioxido-2,3-dihydrothiophen-3-yl 4-benzylbenzenesulfonate (28);

1,1-dioxido-2,3-dihydrothiophen-3-yl 4-(phenoxymethyl) benzenesulfonate (29);

1,1-dioxido-2,3-dihydrothiophen-3-yl [1,1'-biphenyl]-4-sulfonate (33);

1,1-dioxido-2,3-dihydrothiophen-3-yl 4-cyclohexylbenzenesulfonate (34);

1,1-dioxido-2,3-dihydrothiophen-3-yl 3-cyclohexylbenzenesulfonate (35);

1,1-dioxido-2,3-dihydrothiophen-3-yl 4-(cyclohexyloxy) benzenesulfonate (36);

1,1-dioxido-2,3-dihydrothiophen-3-yl 3-(cyclohexyloxy) benzenesulfonate (37);

1,1-dioxido-2,3-dihydrothiophen-3-yl 4-benzoylbenzenesulfonate (38);

1,1-dioxido-2,3-dihydrothiophen-3-yl 4-(hydroxy(phenyl) methyl)benzenesulfonate (39);

1,1-dioxido-2,3-dihydrothiophen-3-yl 2-methyl-4-phenoxybenzenesulfonate (40);

1,1-dioxido-2,3-dihydrothiophen-3-yl 2-methoxy-4-phenoxybenzenesulfonate (41);

1,1-dioxido-2,3-dihydrothiophen-3-yl 4-benzyl-3-methylbenzenesulfonate (42);

1,1-dioxido-2,3-dihydrothiophen-3-yl 3-methoxy-4-phenoxybenzenesulfonate (43);

1,1-dioxido-2,3-dihydrothiophen-3-yl 4-(phenylthio)benzenesulfonate (44);

1,1-dioxido-2,3-dihydrothiophen-3-yl 4-(phenylsulfonyl) benzenesulfonate 45; and a pharmaceutically acceptable salt of any of the foregoing.

Aspect 38. The compound of aspect 1, wherein the compound is selected from:

1,1-dioxido-2,3-dihydrothiophen-3-yl 3-phenoxybenzenesulfonate (25);

1,1-dioxido-2,3-dihydrothiophen-3-yl 4-benzoylbenzenesulfonate (38);

1,1-dioxido-2,3-dihydrothiophen-3-yl 2-methyl-4-phenoxybenzenesulfonate (40);

1,1-dioxido-2,3-dihydrothiophen-3-yl 2-methoxy-4-phenoxybenzenesulfonate (41);

1,1-dioxido-2,3-dihydrothiophen-3-yl 3-methoxy-4-phenoxybenzenesulfonate (43); and a pharmaceutically acceptable salt of any of the foregoing.

Aspect 39. The compound of aspect 1, wherein the compound is selected from:

N-(1,1-dioxido-2,3-dihydrothiophen-3-yl)-N-methylnaphthalene-2-sulfonamide (2);

N-(1,1-dioxido-2,3-dihydrothiophen-3-yl)naphthalene-2-sulfonamide (3);

3-(naphthalen-2-ylmethoxy)-2,3-dihydrothiophene 1,1-dioxide (4);

3-(2-(naphthalen-2-yl)ethoxy)-2,3-dihydrothiophene 1,1-dioxide (7);

2-((1,1-dioxido-2,3-dihydrothiophen-3-yl)oxy)-1-(naphthalen-2-yl)ethan-1-one (8);

1,1-dioxido-2,3-dihydrothiophen-3-yl naphthalen-2-ylcarbamate (10);

1-(1,1-dioxido-2,3-dihydrothiophen-3-yl)-3-(naphthalen-2-yl)urea (12);

1-([1,1'-biphenyl]-4-yl)-3-(1,1-dioxido-2,3-dihydrothiophen-3-yl)urea (13);

N-(1,1-dioxido-2,3-dihydrothiophen-3-yl)-2-naphthamide (14);

N-(1,1-dioxido-2,3-dihydrothiophen-3-yl)-2-(naphthalen-2-yl)acetamide (15);

N-(1,1-dioxido-2,3-dihydrothiophen-3-yl)-N-methylnaphthalene-2-sulfonamide (16);

a pharmaceutically acceptable salt of any of the foregoing.

Aspect 40. The compound of aspect 1, wherein the compound is selected from:

3-([1,1'-biphenyl]-4-ylmethoxy)-2,3-dihydrothiophene 1,1-dioxide (5);

1-([1,1'-biphenyl]-4-yl)-2-((1,1-dioxido-2,3-dihydrothiophen-3-yl)oxy)ethan-1-one (9);

1,1-dioxido-2,3-dihydrothiophen-3-yl [1,1'-biphenyl]-4-ylcarbamate (11);

1-([1,1'-biphenyl]-4-yl)-3-(1,1-dioxido-2,3-dihydrothiophen-3-yl)urea (13);

1,1-dioxido-2,3-dihydrothiophen-3-yl [1,1'-biphenyl]-4-carboxylate (24);

1,1-dioxido-2,3-dihydrothiophen-3-yl [1,1'-biphenyl]-3-sulfonate (26);

1,1-dioxido-2,3-dihydrothiophen-3-yl [1,1'-biphenyl]-4-sulfonate (33);

1,1-dioxido-2,3-dihydrothiophen-3-yl 4-cyclohexylbenzenesulfonate (34);

1,1-dioxido-2,3-dihydrothiophen-3-yl 3-cyclohexylbenzenesulfonate (35);

a pharmaceutically acceptable salt of any of the foregoing.

Aspect 41. The compound of aspect 1, wherein the compound is selected from:

3-((4-phenoxybenzyl)oxy)-2,3-dihydrothiophene 1,1-dioxide (6);

1,1-dioxido-2,3-dihydrothiophen-3-yl [1,1'-biphenyl]-4-ylcarbamate (11);

1,1-dioxido-2,3-dihydrothiophen-3-yl 4-phenoxybenzoate (23);

1,1-dioxido-2,3-dihydrothiophen-3-yl 3-phenoxybenzenesulfonate (25);

1,1-dioxido-2,3-dihydrothiophen-3-yl 4-(benzyloxy)benzenesulfonate (27);

1,1-dioxido-2,3-dihydrothiophen-3-yl 4-benzylbenzenesulfonate (28);

1,1-dioxido-2,3-dihydrothiophen-3-yl 4-(phenoxymethyl) benzenesulfonate (29);

1,1-dioxido-2,3-dihydrothiophen-3-yl 4-(cyclohexyloxy) benzenesulfonate (36);

1,1-dioxido-2,3-dihydrothiophen-3-yl 3-(cyclohexyloxy) benzenesulfonate (37);

1,1-dioxido-2,3-dihydrothiophen-3-yl 4-benzoylbenzenesulfonate (38);

1,1-dioxido-2,3-dihydrothiophen-3-yl 4-(hydroxy(phenyl) methyl)benzenesulfonate (39);

1,1-dioxido-2,3-dihydrothiophen-3-yl 2-methyl-4-phenoxybenzenesulfonate (40);

1,1-dioxido-2,3-dihydrothiophen-3-yl 2-methoxy-4-phenoxybenzenesulfonate (41);

1,1-dioxido-2,3-dihydrothiophen-3-yl 4-benzyl-3-methylbenzenesulfonate (42);

1,1-dioxido-2,3-dihydrothiophen-3-yl 3-methoxy-4-phenoxybenzenesulfonate (43);

1,1-dioxido-2,3-dihydrothiophen-3-yl 4-(phenylthio)benzenesulfonate (44);

1,1-dioxido-2,3-dihydrothiophen-3-yl 4-(phenylsulfonyl) benzenesulfonate 45; and a pharmaceutically acceptable salt of any of the foregoing.

Aspect 42. The compound of aspect 1, with the proviso that the compound is not selected from:

1,1-dioxido-2,3-dihydrothiophen-3-yl naphthalene-2-sulfonate (1):

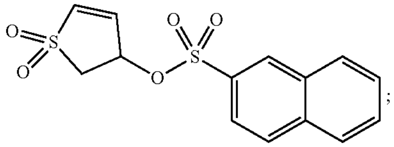 [SMILES: O=S1(=O)C=CC(OS(=O)(=O)c2ccc3ccccc3c2)C1]

;

1,1-dioxido-2,3-dihydrothiophen-3-yl [1,1'-biphenyl]-4-sulfonate (17):

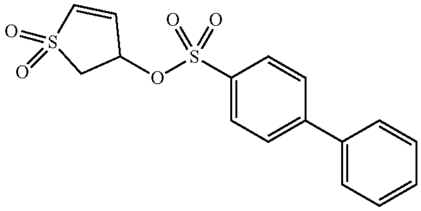

;

1,1-dioxido-2,3-dihydrothiophen-3-yl 4-phenoxybenzenesulfonate (18):

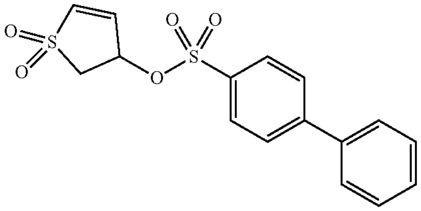

;

(S)-1,1-dioxido-2,3-dihydrothiophen-3-yl 4-phenoxybenzenesulfonate (21):

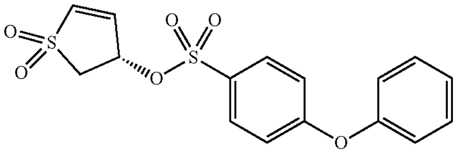

;

(R)-1,1-dioxido-2,3-dihydrothiophen-3-yl 4-phenoxybenzenesulfonate (22):

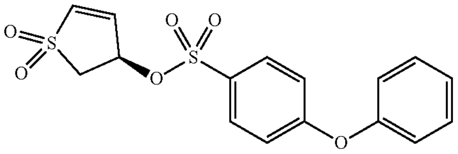

;

or a pharmaceutically acceptable salt of any of the foregoing.

Aspect 43. The compound of any one of aspects 1 to 42, wherein the compound is the free base.

Aspect 44. The compound of any one of aspects 1 to 42, wherein the compound is a pharmaceutically acceptable salt.

Aspect 45. The compound of any one of aspects 1 to 42, wherein the compound is the hydrochloric acid salt.

Aspect 46. A pharmaceutical composition comprising the compound of any one of aspects 1 to 45 or a pharmaceutically acceptable salt thereof, and a pharmaceutically acceptable vehicle.

Aspect 47. A method of treating a disease in a patient comprising administering to a patient in need of such treatment a therapeutically effective amount of the compound of any one of aspects 1 to 45 or a pharmaceutically acceptable salt thereof, or the pharmaceutical composition of aspect 50, wherein the disease is treated by inhibiting extracellular signal-regulated kinase 1 and/or extracellular signal-regulated kinase 2.

Aspect 48. A method of treating a disease in a patient comprising administering to a patient in need of such treatment a therapeutically effective amount of the compound of any one of aspects 1 to 45 or a pharmaceutically acceptable salt thereof, or the pharmaceutical composition of aspect 46, wherein the disease is selected from cancer, an inflammatory disease, an autoimmune disease, or a pulmonary disease.

Aspect 49. The method of aspect 48, wherein the disease is cancer.

Aspect 50. The method of aspect 49, wherein the cancer is selected from melanoma, glioblastoma, and human pancreatic carcinoma, and breast cancer.

Aspect 51. The method of aspect 48, wherein the disease is an inflammatory disease.

Aspect 52. The method of aspect 51, wherein the inflammatory disease is selected from acute respiratory distress syndrome, focal segmental glomerulonephritis, atherosclerosis/acute coronary syndrome, chronic obstructive pulmonary disease, asthma, inflammatory bowel disease, Crohn's disease, psoriasis, lupus, multiple sclerosis, inflammation in hypercholesteremia, pain, diabetes including Type 1 diabetes and Type 2 diabetes, and rheumatoid arthritis.

Aspect 53. The method of aspect 48, wherein the disease is an autoimmune disease.

Aspect 54. The method of aspect 53, wherein the autoimmune disease is selected from lupus, graft-versus-host disease, hepatitis C-induced vasculitis, Type I diabetes, multiple sclerosis, spontaneous loss of pregnancy, an atopic disease, and an inflammatory bowel disease.

Aspect 55. The method of aspect 48, wherein the disease is a pulmonary disease.

Aspect 56. A method of treating a disease in a patient comprising administering to a patient in need of such treatment a therapeutically effective amount of the compound of any one of aspects 1 to 45, or the pharmaceutical composition of aspect 46, wherein the disease is treated by inhibiting extracellular signal-regulated kinase 1 and/or extracellular signal-regulated kinase 2.

Aspect 57. A method of treating a disease in a patient comprising administering to a patient in need of such treatment a therapeutically effective amount of the compound of any one of aspects 1 to 45, or the pharmaceutical composition of aspect 46, wherein the disease is selected from cancer, an inflammatory disease, an autoimmune disease, or a pulmonary disease.

Aspect 58. The method of aspect 57, wherein the disease is cancer.

Aspect 59. The method of aspect 57, wherein the cancer is selected from melanoma, glioblastoma, and human pancreatic carcinoma, and breast cancer.

Aspect 60. The method of aspect 57, wherein the disease is an inflammatory disease.

Aspect 61. The method of aspect 57, wherein the inflammatory disease is selected from acute respiratory distress syndrome, focal segmental glomerulonephritis, atherosclerosis/acute coronary syndrome, chronic obstructive pulmonary disease, asthma, inflammatory bowel disease, Crohn's disease, psoriasis, lupus, multiple sclerosis, inflammation in hypercholesteremia, pain, diabetes including Type 1 diabetes and Type 2 diabetes, and rheumatoid arthritis.

Aspect 62. The method of aspect 57, wherein the disease is an autoimmune disease.

Aspect 63. The method of aspect 57, wherein the autoimmune disease is selected from lupus, graft-versus-host disease, hepatitis C-induced vasculitis, Type I diabetes, multiple sclerosis, spontaneous loss of pregnancy, an atopic disease, and an inflammatory bowel disease.

Aspect 64. The method of aspect 57, wherein the disease is a pulmonary disease.

Aspect 65. A method of treating a disease in a patient comprising administering to a patient in need of such treatment a therapeutically effective amount of the compound of any one of aspects 1 to 45 or a pharmaceutically acceptable salt thereof, or the pharmaceutical composition of aspect 46, wherein the disease is selected from acute coronary syndrome, acute lung injury, acute respiratory distress syndrome (ARDS), Alzheimer's disease, asthma, a cardiovascular disease, chronic obstructive pulmonary disease (COPD), inflammatory bowel disease, major depressive disorder, multiple sclerosis, neuropathic pain, and rheumatoid arthritis.

Aspect 66. A method of treating a disease in a patient comprising administering to a patient in need of such treatment a therapeutically effective amount of the compound of any one of aspects 1 to 45, or the pharmaceutical composition of aspect 46, wherein the disease is selected from acute coronary syndrome, acute lung injury, acute respiratory distress syndrome (ARDS), Alzheimer's disease, asthma, a cardiovascular disease, chronic obstructive pulmonary disease (COPD), inflammatory bowel disease, major depressive disorder, multiple sclerosis, neuropathic pain, and rheumatoid arthritis.

EXAMPLES

The following examples describe in detail the synthesis of compounds of Formula (1)-(45), the characterization of compounds of Formula (1)-(45), and uses of compounds of Formula (1)-(45). It will be apparent to those skilled in the art that many modifications, both to materials and methods, may be practiced without departing from the scope of the disclosure.

Example A

Synthesis of 6-oxa-3-thiabicyclo[3.1.0]hexane 3,3-dioxide (A)

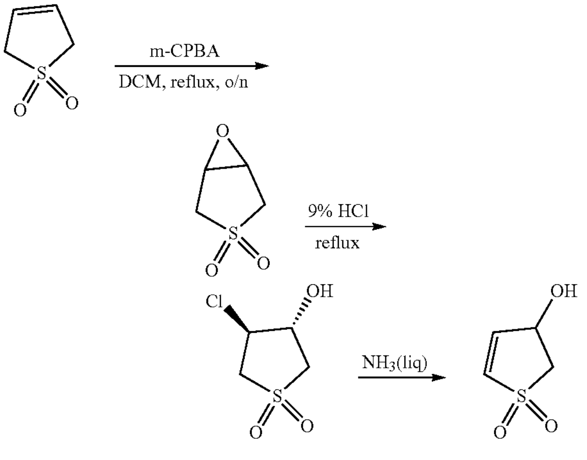

A

Step 1. Synthesis of 6-oxa-3-thiabicyclo[3.1.0]hexane 3,3-dioxide

To a solution of 2,5-dihydrothiophene 1,1-dioxide (25.0 g, 211.5 mmol) in DCM (500 mL) was added m-CPBA (91.2 g, 528.7 mmol) at 0° C. The reaction mixture was stirred at 40° C. under $N_2$ overnight. The reaction mixture was cooled down to 0° C., quenched with sat. $Na_2SO_3$ (aq) (1 L), stirred at 23° C. for 30 mins and filtered. The filtration was extracted with DCM (400 mL×2), the combined organic layers were washed with water, brine and concentrated in vacuum, purified by silica gel column chromatography (PE/EtOAc=1/1, v/v) to afford 6-oxa-3-thiabicyclo[3.1.0]hexane 3,3-dioxide (15 g, 52.9% yield) as a white solid. $^1$H NMR (400 MHz, DMSO-$d_6$) δ 3.99 (d, J=2.0 Hz, 2H), 3.58 (dd, J=14.9, 2.1 Hz, 2H), 3.39 (d, J=14.7 Hz, 2H).

Step 2. Synthesis of (3S,4R)-3-chloro-4-hydroxytetrahydrothiophene 1,1-dioxide

6-Oxa-3-thiabicyclo[3.1.0]hexane 3,3-dioxide (15 g, 111.8 mmol) was dissolved in 9% HCl (300 mL) and the mixture was heated to reflux overnight. The mixture was cooled to 0° C. and filtered. The filter cake was washed with water and dried to afford (3S,4R)-3-chloro-4-hydroxytetrahydrothiophene 1,1-dioxide (10 g, 52.4% yield) as a white solid. $^1$H NMR (400 MHz, DMSO-$d_6$) δ 6.32 (d, J=4.2 Hz, 1H), 4.65-4.59 (m, 1H), 4.55-4.47 (m, 1H), 3.77 (dd, J=14.2, 6.4 Hz, 1H), 3.55 (dd, J=13.8, 5.8 Hz, 1H), 3.43 (dd, J=14.3, 4.1 Hz, 1H), 3.12 (dd, J=13.8, 3.6 Hz, 1H).

Step 3. Synthesis of 6-oxa-3-thiabicyclo[3.1.0]hexane 3,3-dioxide (A)

(3S,4R)-3-Chloro-4-hydroxytetrahydrothiophene 1,1-dioxide (7 g, 41.1 mmol) was slowly added to liquid ammonia (80 mL) over 10 mins. The mixture was stirred at −70° C. for 1 hour and warmed to 23° C. for 30 min. DCM (20 mL) was added to the reaction mixture, stirred for 10 mins, and filtered. The filtrate was concentrated in vacuum to afford 6-oxa-3-thiabicyclo[3.1.0]hexane 3,3-dioxide (A) (1.5 g, 27.3% yield) as a colorless oil. $^1$H NMR (400 MHz, chloroform-d) δ 6.78 (dd, J=6.7, 2.8 Hz, 1H), 6.71 (dd, J=6.7, 1.3 Hz, 1H), 5.16-5.11 (m, 1H), 3.62 (dd, J=13.9, 7.4 Hz, 1H), 3.19 (dd, J=13.9, 3.6 Hz, 1H).

Example B

Synthesis of 3-amino-2,3-dihydrothiophene 1,1-dioxide (B)

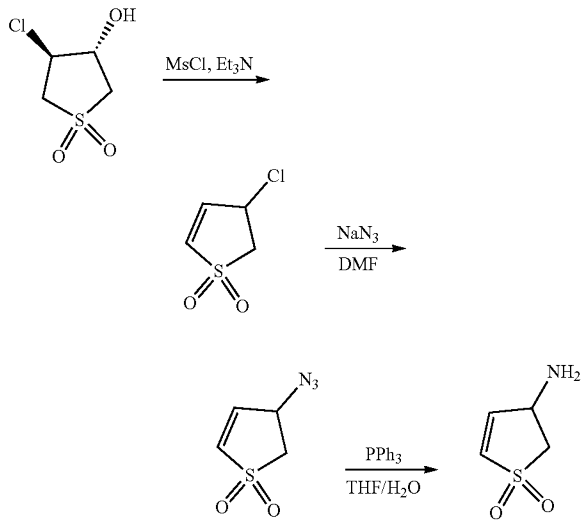

B

Step 1: Synthesis of dihydrothiophene 1,1-dioxide

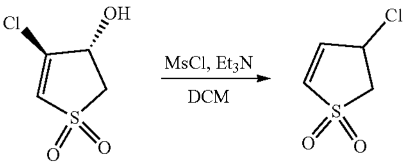

To a solution of (3S,4R)-3-chloro-4-hydroxytetrahydrothiophene 1,1-dioxide (17 g, 0.10 mol) in DCM (30 mL) was added $Et_3N$ (20.1 g, 0.20 mol) and MsCl (17.1 g, 0.15 mol) at 0° C. The mixture was stirred overnight at 23° C. The mixture was diluted with water (200 mL) and extracted with DCM (80 mL×2). The combined organic phase was washed by brine (100 mL), dried over $Na_2SO_4$, concentrated, and purified by silica chromatography gel (PE:EtOAc=5/1 to 3/1) to afford 3-chloro-2,3-dihydrothiophene 1,1-dioxide (4.4 g, 28.9% yield) as a white solid. $^1$HNMR: (400 MHz, Chloroform-d) δ 6.80 (dd, J=6.7, 1.4 Hz, 1H), 6.74 (dd, J=6.7, 2.7 Hz, 1H), 5.19-5.11 (m, 1H), 3.80 (dd, J=14.3, 7.8 Hz, 1H), 3.46 (dd, J=14.3, 3.9 Hz, 1H).

Step 2: Synthesis of 3-azido-2,3-dihydrothiophene 1,1-dioxide

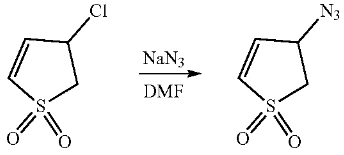

To a solution of 3-chloro-2,3-dihydrothiophene 1,1-dioxide (2.5 g, 16.4 mmol) in DMF (15 mL) was added $NaN_3$ (2.40 g, 36.8 mmol). The mixture was stirred at 23° C. for 4 h. The reaction mixture was then diluted with water (150 mL) and extracted with EtOAc (60 mL×3). The combined organic phase was washed with water (100 mL) and brine (100 mL), dried over $Na_2SO_4$, and concentrated to afford 3-azido-2,3-dihydrothiophene 1,1-dioxide (1.8 g, 69.0% yield) as a yellow solid. $^1$H NMR: (400 MHz, Chloroform-d) δ 6.86 (dd, J=6.7, 1.8 Hz, 1H), 6.72 (dd, J=6.7, 2.9 Hz, 1H), 4.80 (m, 1H), 3.65 (dd, J=13.9, 7.9 Hz, 1H), 3.23 (dd, J=13.9, 4.3 Hz, 1H).

Step 3. Synthesis of 3-amino-2,3-dihydrothiophene 1,1-dioxide (B)

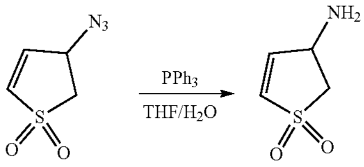

B

To a solution of 3-azido-2,3-dihydrothiophene 1,1-dioxide (1.8 g, 11.3 mmol) in THF (16 mL) and water (4 mL)

was added $PPh_3$ (4.45 g, 17.0 mmol). The mixture was stirred at 23° C. for 5 h. The solvent was removed in vacuo. The residue was purified by silica chromatography gel (DCM:MeOH=50/1 to 30/1) to afford 3-amino-2,3-dihydrothiophene 1,1-dioxide (B) (1.0 g, 66.4% yield) as a colorless oil. $^1H$ NMR (400 MHz, DMSO-$d_6$) δ 6.95 (dd, J=6.6, 2.0 Hz, 1H), 6.75 (dd, J=6.6, 2.5 Hz, 1H), 4.21-4.14 (m, 1H), 3.58 (dd, J=13.4, 7.5 Hz, 1H), 2.86 (dd, J=13.5, 5.0 Hz, 1H).

Example 1

Synthesis of 1,1-dioxido-2,3-dihydrothiophen-3-yl naphthalene-2-sulfonate (1)

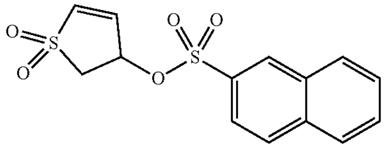 [SMILES: O=S1(=O)C=CC(OS(=O)(=O)c2ccc3ccccc3c2)C1]

1,1-Dioxido-2,3-dihydrothiophen-3-yl naphthalene-2-sulfonate (1) was synthesized using the method described in Scheme 1 of U.S. Pat. No. 9,155,122 B2 on columns 47-48.

Example 2

Synthesis of N-(1,1-dioxido-2,3-dihydrothiophen-3-yl)-N-methylnaphthalene-2-sulfonamide (2)

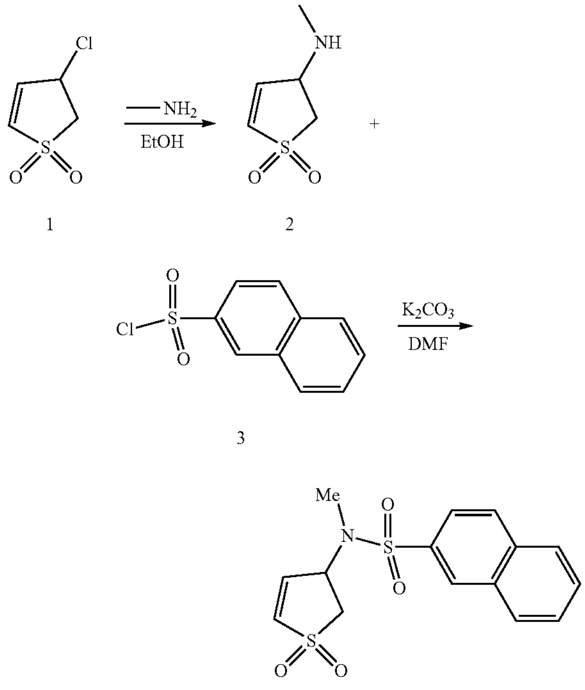

1
2
3
1896

Step 1. Synthesis of 3-(methylamino)-2,3-dihydrothiophene 1,1-dioxide (2b)

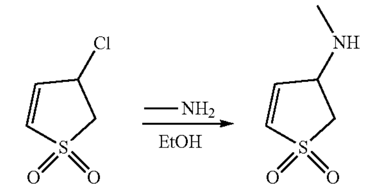

1
2

To a solution of 3-chloro-2,3-dihydrothiophene 1,1-dioxide (2a) (80 mg, 0.52 mmol) in EtOH (2 mL) was added methylamine (0.5 mL) (2N in THF). The mixture was stirred at 23° C. for 1 h. The reaction mixture was concentrated to dryness, the residue dissolved in DCM (5 mL), and filtered. The filtrate was concentrated to dryness to afford 3-(methylamino)-2,3-dihydrothiophene 1,1-dioxide (2b) (70 mg, 90.5% yield) as brown oil. $^1H$ NMR (400 MHz, DMSO-d6) δ 7.06 (dd, J=6.7, 2.0 Hz, 1H), 6.83 (dd, J=6.7, 2.6 Hz, 1H), 4.14-4.06 (m, 1H), 3.55 (dd, J=13.6, 7.5 Hz, 1H), 2.97 (dd, 1H), 2.26 (s, 3H).

Step 2. Synthesis of N-(1,1-dioxido-2,3-dihydrothiophen-3-yl)-N-methylnaphthalene-2-sulfonamide (2)

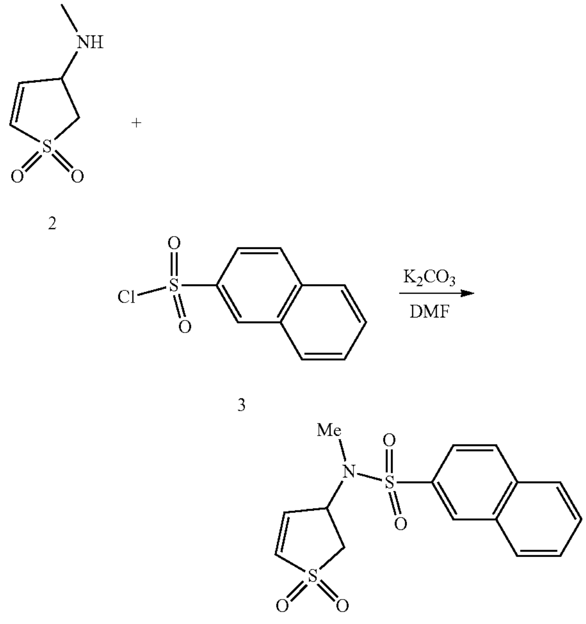

2
3
1896

To a solution of compound (2b) (70 mg, 0.48 mmol) in DMF (2 mL) was added $K_2CO_3$ (99 mg, 0.71 mmol) and naphthalene-2-sulfonyl chloride (2c) (108 mg, 0.48 mmol). The mixture was stirred at 50° C. for 5 min. The mixture was diluted with water (20 mL) and extracted with EtOAc (10 mL×3). The combined organic phase was washed with water (30 mL) and brine (30 mL), dried over $Na_2SO_4$, concentrated, and purified by Prep-TLC (PE:EtOAc=2:1) to afford N-(1,1-dioxido-2,3-dihydrothiophen-3-yl)-N-methylnaphthalene-2-sulfonamide (2) (41.1 mg, 25.7% yield) as a white solid. $^1$H NMR (400 MHz, DMSO-$d_6$) δ 8.55-8.54 (m, 1H), 8.21-8.17 (m, 2H), 8.10 (d, J=7.9 Hz, 1H), 7.88 (dd, J=8.7, 1.9 Hz, 1H), 7.78-7.67 (m, 2H), 7.31 (dd, J=6.7, 2.1 Hz, 1H), 6.61 (dd, J=6.7, 3.1 Hz, 1H), 5.64-5.57 (m, 1H), 3.54 (dd, J=14.4, 8.7 Hz, 1H), 2.84 (dd, J=14.4, 3.5 Hz, 1H), 2.63 (s, 3H). LCMS: 1.766 min, $C_{15}H_{15}NO_4S_2$; [M+1]=338.1, [M+23]=360.1.

Example 3

Synthesis of N-(1,1-dioxido-2,3-dihydrothiophen-3-yl)naphthalene-2-sulfonamide (3)

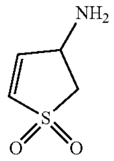

B

+

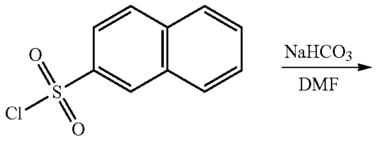

3a

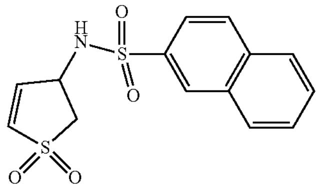

3

To a solution of compound (B) (Example B) (50 mg, 0.38 mmol) in DMF (3 mL) was added $NaHCO_3$ (63.2 mg, 0.75 mmol) and 3-(methylamino)-2,3-dihydrothiophene 1,1-dioxide (3a) ((85.2 mg, 0.38 mmol). The mixture was stirred at 50° C. for 4 h. The mixture was diluted with water (10 mL) and the pH was adjusted to 6-7 with HCOOH. The mixture was concentrated in vacuo and purified by Prep-HPLC to afford N-(1,1-dioxido-2,3-dihydrothiophen-3-yl) naphthalene-2-sulfonamide (3) (10.8 mg, 8.89% yield) as a white solid. $^1$H NMR: (400 MHz, DMSO-$d_6$) δ 8.61 (s, 1H), 8.52 (d, J=1.8 Hz, 1H), 8.18 (dd, J=8.8, 4.0 Hz, 2H), 8.07 (d, J=7.8 Hz, 1H), 7.87 (dd, J=8.7, 1.9 Hz, 1H), 7.78-7.65 (m, 2H), 7.17 (dd, J=6.7, 2.1 Hz, 1H), 6.58 (dd, J=6.7, 2.7 Hz, 1H), 4.94-4.74 (m, 1H), 3.51 (dd, J=13.8, 8.1 Hz, 1H), 2.79 (dd, J=13.8, 4.5 Hz, 1H). LCMS: 1.524 min, $C_{14}H_{13}NO_4S_2$; [M−1]=322.0.

Example 4

Synthesis of 3-(naphthalen-2-ylmethoxy)-2,3-dihydrothiophene 1,1-dioxide (4)

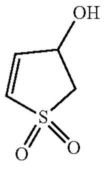

A

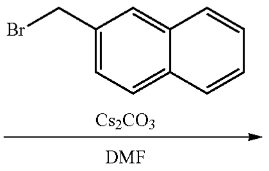

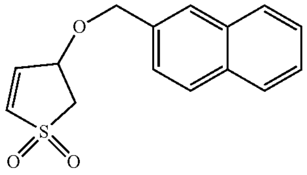

4

To a solution of compound A (Example A) (50.0 mg, 0.373 mmol) in DMF (2 mL) was added 2-(bromomethyl) naphthalene (82.5 mg, 0.373 mmol) and $Cs_2CO_3$ (181.9 mg, 0.559 mmol) at 0° C. The reaction mixture was stirred at room temperature for 0.5 h. Water (20 mL) was added and the mixture extracted with EtOAc (10 mL×2). The combined organic layers were washed with water, brine and concentrated, purified by Prep-TLC (DCM/MeOH=15/1, v/v) to afford 3-(naphthalen-2-ylmethoxy)-2,3-dihydrothiophene 1,1-dioxide (4) (20.1 mg, 19.7% yield) as a white solid. $^1$H NMR (400 MHz, chloroform-d) δ 7.88-7.83 (m, 3H), 7.78 (s, 1H), 7.55-7.49 (m, 2H), 7.45 (dd, J=8.5, 1.7 Hz, 1H), 6.76-6.70 (m, 2H), 4.97-4.92 (m, 1H), 4.84-4.73 (m, 2H), 3.54 (dd, J=13.6, 7.2 Hz, 1H), 3.23 (dd, J=13.6, 4.2 Hz, 1H). LCMS: 1.863 min, $C_{15}H_{14}O_3S$; [M+23]=297.0.

Example 5

Synthesis of 3-([1,1'-biphenyl]-4-ylmethoxy)-2,3-dihydrothiophene 1,1-dioxide (5)

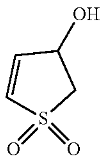

A

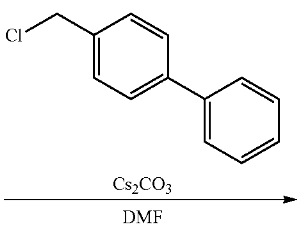

-continued

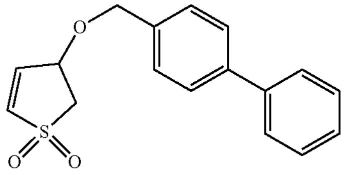

5

To a solution of compound A (Example A) (50.0 mg, 0.373 mmol) in DMF (2 mL) was added 4-(chloromethyl)-1,1'-biphenyl (75.6 mg, 0.373 mmol) and $Cs_2CO_3$ (181.9 mg, 0.559 mmol) at 0° C. The reaction mixture was stirred at room temperature for 0.5 h. Water (20 mL) was added and extracted with EtOAc (10 mL×2). The combined organic layers were washed with water and brine, and concentrated to afford the crude product which was purified by Prep-TLC (DCM/MeOH=15/1, v/v) to afford 3-([1,1'-biphenyl]-4-ylmethoxy)-2,3-dihydrothiophene 1,1-dioxide (5) (19.1 mg, 17.1% yield) as a white solid. $^1$H NMR (400 MHz, chloroform-d) δ 7.60 (t, J=8.2 Hz, 4H), 7.49-7.33 (m, 5H), 6.79-6.70 (m, 2H), 4.97-4.91 (m, 1H), 4.71-4.61 (m, 2H), 3.57 (dd, J=13.5, 7.2 Hz, 1H), 3.24 (dd, J=13.5, 4.2 Hz, 1H). LCMS: 2.071 min, $C_{17}H_{16}O_3S$; [M+18]=318.1, [M+23]=323.1.

Example 6

Synthesis of 3-((4-phenoxybenzyl)oxy)-2,3-dihydrothiophene 1,1-dioxide (6)

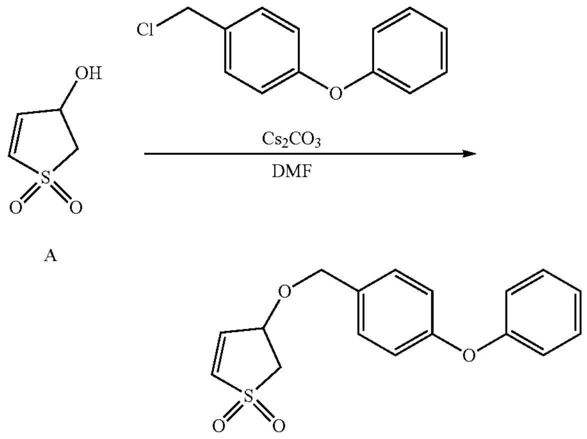

A

6

To a solution of compound A (Example A) (50.0 mg, 0.373 mmol) in DMF (2 mL) was added 1-(chloromethyl)-4-phenoxybenzene (81.6 mg, 0.373 mmol) and $Cs_2CO_3$ (181.9 mg, 0.559 mmol) at 0° C. The reaction mixture was stirred at 23° C. for 0.5 h. Water (20 mL) was added and extracted with EtOAc (10 mL×2). The combined organic layers were washed with water and brine, concentrated, and purified by Prep-TLC (DCM/MeOH=15/1, v/v) to afford 3-((4-phenoxybenzyl)oxy)-2,3-dihydrothiophene 1,1-dioxide (6) (19.3 mg, 16.4% yield) as a white solid. $^1$H NMR (400 MHz, Chloroform-d) δ 7.40-7.32 (m, 2H), 7.31-7.26 (m, 2H), 7.13 (t, J=7.4 Hz, 1H), 7.05-6.96 (m, 4H), 6.77-6.68 (m, 2H), 4.93-4.87 (m, 1H), 4.63-4.54 (m, 2H), 3.55 (dd, J=13.5, 7.2 Hz, 1H), 3.20 (dd, J=13.5, 4.3 Hz, 1H). LCMS: 2.069 min, $C_{17}H_{16}O_4S$; [M+18]=334.1, [M+23]=339.1.

Example 7

Synthesis of 3-(2-(naphthalen-2-yl)ethoxy)-2,3-dihydrothiophene 1,1-dioxide (7)

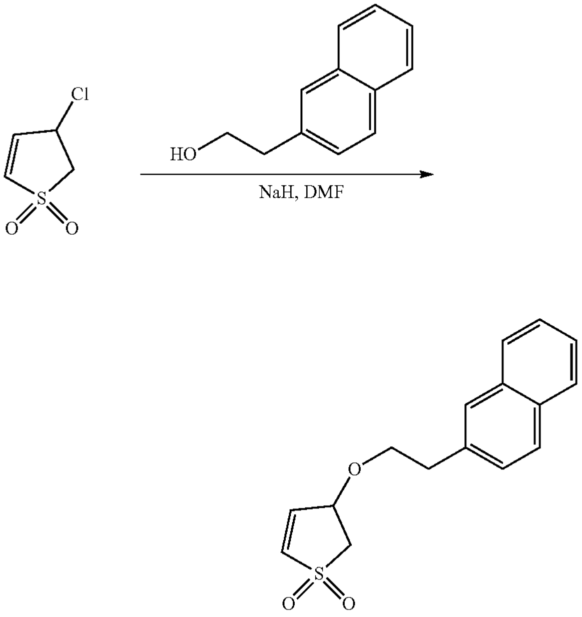

7

To a solution of 2-(naphthalen-2-yl)ethan-1-ol (226.3 mg, 1.32 mmol) in DMF (3 mL) was added NaH (31.7 mg, 0.792 mmol) at 0° C., and the mixture was stirred at 23° C. for 1 h. 3-Chloro-2,3-dihydrothiophene 1,1-dioxide (100 mg, 0.66 mmol) was added. The reaction was stirred at room temperature for 0.5 h. Water (30 mL) was added and extracted with EtOAc (15 mL×3). The combined organic layers were washed with water, brine and concentrated, purified by Prep-TLC (DCM/MeOH=15/1, v/v) to afford 3-(2-(naphthalen-2-yl)ethoxy)-2,3-dihydrothiophene 1,1-dioxide (7) (18.2 mg, 9.6% yield) as a white solid. $^1$H NMR (400 MHz, chloroform-d) δ 7.85-7.75 (m, 3H), 7.65 (s, 1H), 7.51-7.42 (m, 2H), 7.33 (dd, J=8.3, 1.7 Hz, 1H), 6.70-6.65 (m, 2H), 4.83-4.77 (m, 1H), 3.86-3.79 (m, 2H), 3.53 (dd, J=13.5, 7.2 Hz, 1H), 3.14 (dd, J=13.5, 4.1 Hz, 1H), 3.06 (t, J=6.7 Hz, 2H). LCMS: 1.997 min, $C_{16}H_{16}O_3S$; [M+18]=306.1, [M+23]=311.1.

Example 8

Synthesis of 2-((1,1-dioxido-2,3-dihydrothiophen-3-yl)oxy)-1-(naphthalen-2-yl)ethan-1-one (8)

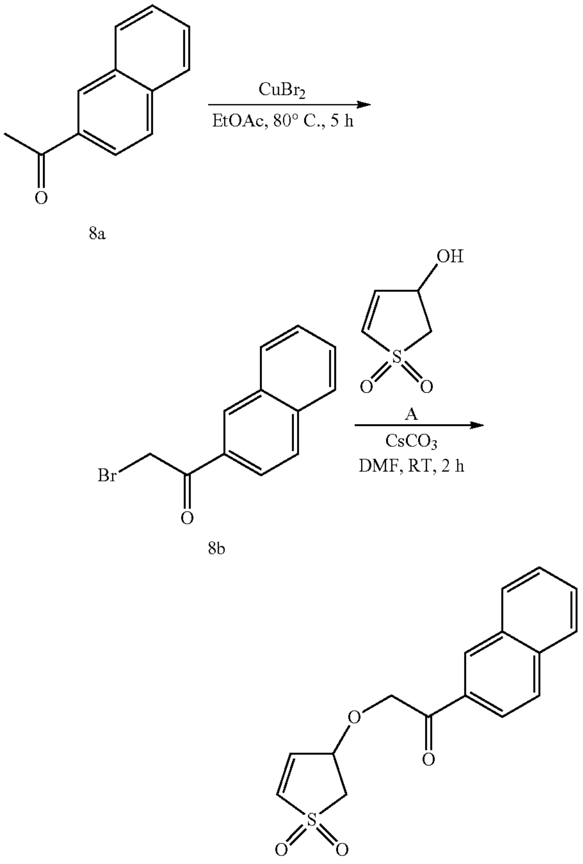

8a

8b

8

Step 1. Synthesis of 3-bromo-1-(naphthalen-2-yl) propan-1-one (8b)

To a solution of 2-naphthyl chloride (8a) (6 g, 35.25 mmol) in EtOAc (50 mL) was added $CuBr_2$ (15.75 g, 70.50 mmol) at 23° C. and stirred at 80° C. for 5 h. The reaction mixture was cooled to 23° C., diluted with water (80 mL), extracted with EtOAc (40 mL×3). The combined organic layers were washed with brine, dried over $Na_2SO_4$, and concentrated. The residue was purified by silica gel column chromatography (PE/EtOAc=50:1, v/v) to afford 3-bromo-1-(naphthalen-2-yl)propan-1-one (8b) (3.8 g, 43.27% yield) as a white solid. $^1$H NMR (400 MHz, DMSO-d6) δ 8.75 (s, 1H), 8.14-8.11 (m, 1H), 8.07-7.99 (m, 3H), 7.72-7.64 (m, 2H), 5.06 (s, 2H).

Step 2. Synthesis of 2-((1,1-dioxido-2,3-dihydrothiophen-3-yl)oxy)-1-(naphthalen-2-yl)ethan-1-one (8)

To a solution of compound A (Example A) (100 mg, 0.745 mmol) in DMF (2 mL) were added $Cs_2CO_3$ (364.32 mg, 1.12 mmol) and 3-bromo-1-(naphthalen-2-yl)propan-1-one (8b) (278.54 mg, 1.12 mmol) at 0° C. The reaction mixture was warmed to 23° C. and stirred for 2 h. The mixture was diluted with water (20 mL) and extracted with EtOAc (15 mL×3). The combined organic layers were washed with brine, dried over $Na_2SO_4$, filtered and concentrated. The residue was purified by Prep-TLC×2 (DCM/MeOH=15/1, v/v) and Prep-HPLC to afford 2-((1,1-dioxido-2,3-dihydrothiophen-3-yl)oxy)-1-(naphthalen-2-yl)ethan-1-one (8) (30 mg, 13.31% yield) as a white solid. $^1$H NMR (400 MHz, chloroform-d) δ 8.41 (s, 1H), 8.00-7.87 (m, 4H), 7.68-7.55 (m, 2H), 6.99-6.91 (m, 1H), 6.77 (dd, J=6.8, 1.7 Hz, 1H), 5.11-4.97 (m, 3H), 3.73-3.65 (m, 1H), 3.43-3.35 (m, 1H). LCMS: 1.681 min, $C_{16}H_{14}O_4S$; [M+1]=303.1, [M+18]=320.1, [M+23]=325.1.

Example 9

Synthesis of 1-([1,1'-biphenyl]-4-yl)-2-((1,1-dioxido-2,3-dihydrothiophen-3-yl)oxy)ethan-1-one (9)

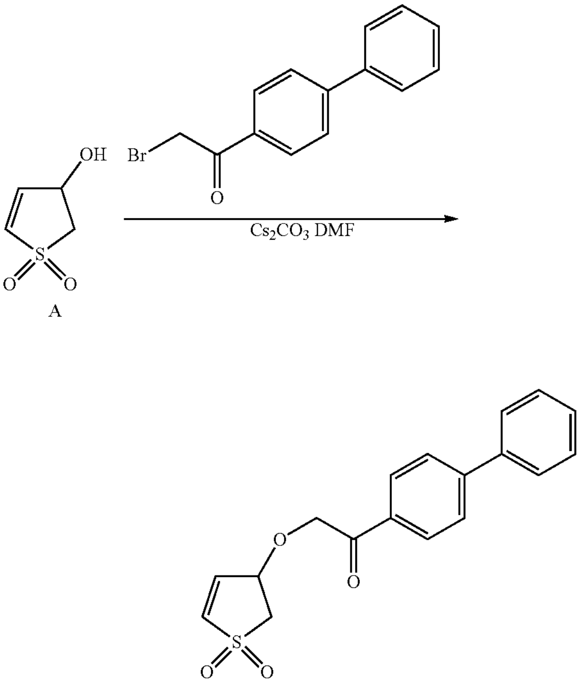

A

9

To a solution of compound (A) (100.0 mg, 0.746 mmol) in DMF (2 mL) were added 1-([1,1'-biphenyl]-4-yl)-2-bromoethan-1-one (205 mg, 0.746 mmol) and $Cs_2CO_3$ (363.8 mg, 1.12 mmol) at 0° C. The reaction mixture was stirred at 23° C. for 1 h. Water (20 mL) was added and extracted with EtOAc (15 mL×3). The combined organic layers were washed with water and brine, concentrated, and purified by Prep-TLC (DCM/MeOH=15/1, v/v) to afford 1-([1,1'-biphenyl]-4-yl)-2-((1,1-dioxido-2,3-dihydrothiophen-3-yl)oxy)ethan-1-one (9) (18.1 mg, 7.4% yield) as a white solid. $^1$H NMR (400 MHz, chloroform-d) δ 7.97 (d, J=8.1 Hz, 2H), 7.72 (d, J=8.0 Hz, 2H), 7.63 (d, J=7.5 Hz, 2H), 7.52-7.40 (m, 3H), 6.94 (dd, J=6.8, 2.6 Hz, 1H), 6.77 (d, J=6.7 Hz, 1H), 5.06-5.00 (m, 1H), 5.00-4.87 (m, 2H), 3.67 (dd, J=13.7, 7.3 Hz, 1H), 3.37 (dd, J=13.7, 3.9 Hz, 1H). LCMS: 1.902 min, $C_{18}H_{16}O_4S$; [M+1]=329.1, [M+23]=351.1.

Example 10

Synthesis of 1,1-dioxido-2,3-dihydrothiophen-3-yl naphthalen-2-ylcarbamate (10)

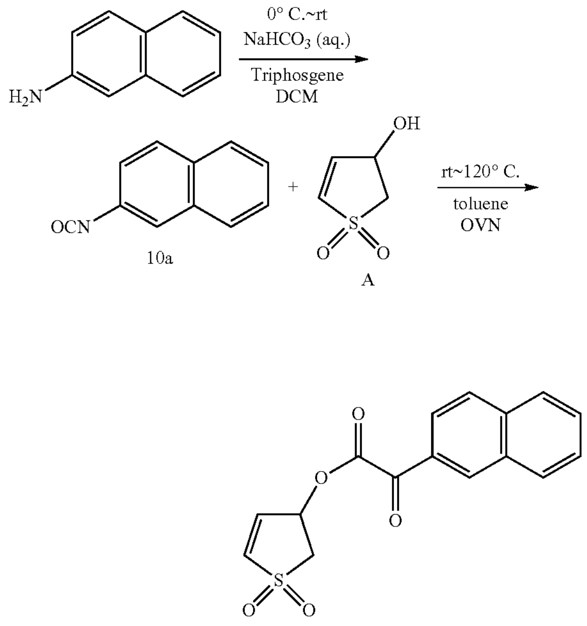

10a
A

10

Step 1. Synthesis of 2-cyanothaphthalene (10a)

To a solution of naphthalen-2-amine (50 mg, 0.35 mmol) in DCM (5 mL) and $NaHCO_3$ (aq) (5 mL) was added triphosgene (36 mg, 0.12 mmol) in DCM (1 mL) at 0° C. The mixture was stirred at 23° C. for 1 h. The organic layer was separated, dried over $Na_2SO_4$ and concentrated in vacuum to afford 2-cyanothaphthalene (10a) (59 mg) as a yellow oil, used directly in the next step.

Step 2. Synthesis of 1,1-dioxido-2,3-dihydrothiophen-3-yl naphthalen-2-ylcarbamate (10)

To a solution of compound (A) (47 mg, 0.35 mmol) in toluene (5 mL) was added 2-cyanothaphthalene (10a) (59 mg, 0.35 mmol). The mixture was stirred overnight at 120° C. The mixture was cooled to 23° C. and quenched with water (20 mL) and extracted with EtOAc (20 mL×2). The combined organic layers were washed by water (20 mL) and brine (20 mL), dried over $Na_2SO_4$, and concentrated in vacuum and purified by Prep-TLC (PE./EtOAc=2/1) to afford 1,1-dioxido-2,3-dihydrothiophen-3-yl naphthalen-2-ylcarbamate (10) (25 mg, 23.6% yield) as a white solid. $^1H$ NMR (400 MHz, DMSO-$d_6$): δ 10.18 (s, 1H), 8.07 (s, 1H), 7.88-7.76 (m, 3H), 7.54 (d, J=10.3 Hz, 1H), 7.48-7.37 (m, 3H), 7.07 (dd, J=6.7, 3.3 Hz, 1H), 6.07-5.99 (m, 1H), 3.83 (dd, J=14.6, 7.6 Hz, 1H), 3.41 (dd, J=14.5, 2.5 Hz, 1H). LCMS: 1.765 min, $C_{15}H_{13}NO_4S$; [M+23]=326.0.

Example 11

Synthesis of 1,1-dioxido-2,3-dihydrothiophen-3-yl [1,1'-biphenyl]-4-ylcarbamate (11)

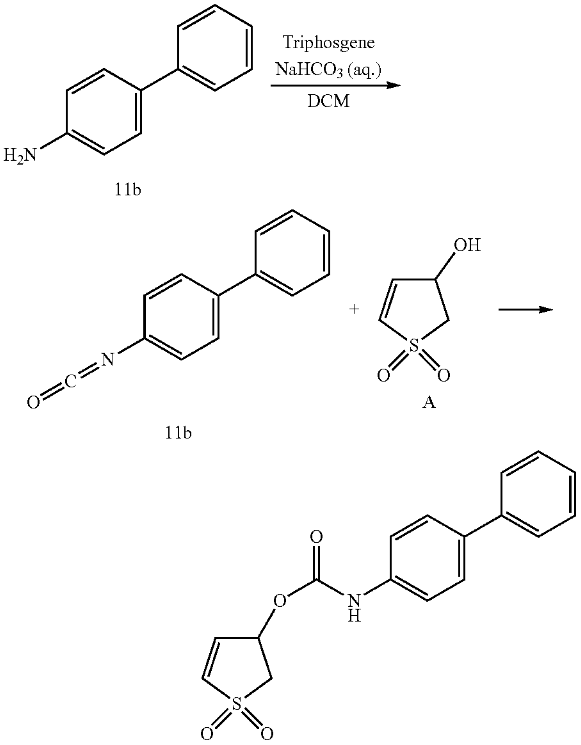

11b
11b
A

11

Step 1. Synthesis of 4-cyanato-1,1'-biphenyl (11b)

To a solution of [1,1'-biphenyl]-4-amine (11a) (200 mg, 1.18 mmol) in DCM (4 mL) and $NaHCO_3$ (aq) (4 mL) was added and triphosgene (175 mg, 0.59 mmol) in DCM (1 mL) at 0° C. The mixture was stirred at 23° C. for 2 h. The mixture was diluted with water (10 mL), extracted with DCM (10 mL). The organic phase was washed by brine (30 mL), dried over $Na_2SO_4$ and concentrated in vacuum to afford 4-cyanato-1,1'-biphenyl (11b) (210 mg, 91.0% yield) as a yellow solid.

Step 2. Synthesis of 1,1-dioxido-2,3-dihydrothiophen-3-yl [1,1'-biphenyl]-4-ylcarbamate (11)

A solution of 4-cyanato-1,1'-biphenyl (11b) ((100 mg, 0.75 mmol) and compound (A) (Example A) (146 mg, 0.75 mmol) in toluene (5 mL) was stirred at 120° C. overnight. The reaction mixture was concentrated and purified by silica gel column chromatography (DCM/MeOH=500/1, v/v) to afford 1,1-dioxido-2,3-dihydrothiophen-3-yl [1,1'-biphenyl]-4-ylcarbamate (11) (14.0 mg, 5.6% yield) as a white solid. $^1H$ NMR (400 MHz, DMSO-$d_6$) δ 10.06 (s, 1H), 7.64-7.61 (m, 4H), 7.56 (d, J=8.4 Hz, 2H), 7.47-7.39 (m, 3H), 7.32 (t, J=7.2 Hz, 1H), 7.06 (dd, J=6.7, 3.3 Hz, 1H), 6.02-5.98 (m, 1H), 3.81 (dd, J=14.5, 7.6 Hz, 1H), 3.39 (dd, J=14.6, 2.5 Hz, 1H). LCMS: 1.972 min, $C_{17}H_{15}NO_4S$; [M+23]=352.1.

Example 12

Synthesis of 1-(1,1-dioxido-2,3-dihydrothiophen-3-yl)-3-(naphthalen-2-yl)urea (12)

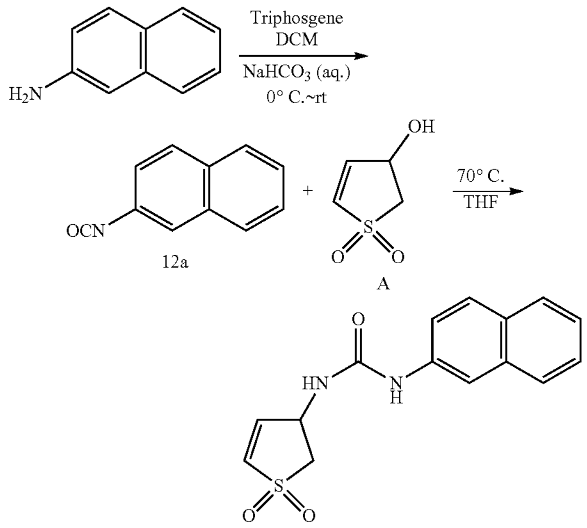

12a

A

12

Step 1. Synthesis of 2-cyanatonaphthalene

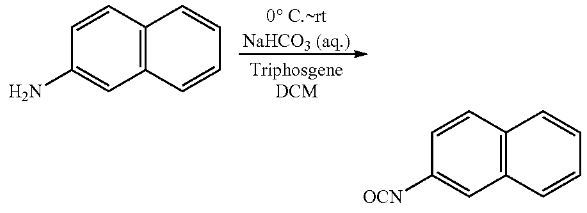

12a

To a solution of naphthalen-2-amine (86 mg, 0.60 mmol) in DCM (5 mL) and $NaHCO_3$ (aq) (5 mL) was added triphosgene (71 mg, 0.24 mmol) at 0° C. The mixture was stirred at 23° C. 1 h. The organic layer was separated and dried over $Na_2SO_4$, concentrated in vacuum to afford 2-cyanatonaphthalene (12a) (101 mg, 99.5% yield) as a yellow oil, used directly in the next step.

Step 2. Synthesis of 1-(1,1-dioxido-2,3-dihydrothiophen-3-yl)-3-(naphthalen-2-yl)urea (12)

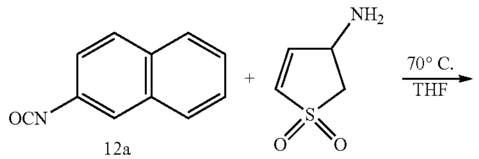

12a

B

-continued

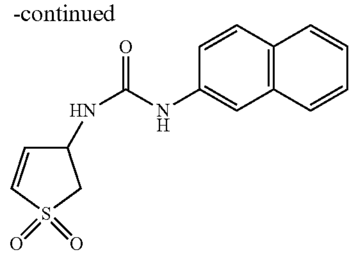

12

To a solution of compound (B) (80 mg, 0.60 mmol) in THF (10 mL) was added 2-cyanatonaphthalene (12a) (101 mg, 0.60 mmol) and the mixture was heated to 70° C. overnight. The mixture was cooled down to 23° C. and quenched with water (20 mL), extracted with EtOAc (20 mL×2). The combined organic layer was washed by water (20 mL) and brine (20 mL), dried over $Na_2SO_4$, concentrated in vacuum and purified by silica gel column chromatography (from DCM to DCM/MeOH=30/1) to afford 1-(1,1-dioxido-2,3-dihydrothiophen-3-yl)-3-(naphthalen-2-yl) urea (12). (85 mg, 46.8% yield) as a white solid. $^1H$ NMR (400 MHz, DMSO-$d_6$): δ 8.83 (s, 1H), 8.03 (d, J=2.1 Hz, 1H), 7.83-7.71 (m, 3H), 7.50-7.39 (m, 2H), 7.37-7.29 (m, 1H), 7.20 (dd, J=6.6, 1.9 Hz, 1H), 6.93 (dd, J=6.6, 2.9 Hz, 1H), 6.88 (d, J=8.1 Hz, 1H), 5.28-5.04 (m, 1H), 3.71 (dd, J=13.7, 7.8 Hz, 1H), 3.19 (dd, J=13.6, 4.3 Hz, 1H). LCMS: 1.435 min, $C_{15}H_{14}N_2O_3S$; [M+1]=303.1.

Example 13

Synthesis of 1-([1,1'-biphenyl]-4-yl)-3-(1,1-dioxido-2,3-dihydrothiophen-3-yl)urea (13)

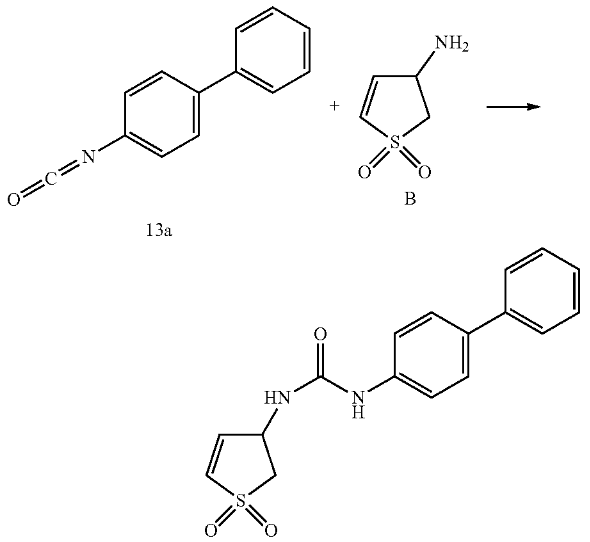

B

13a

13

A solution of 2-cyanatonaphthalene (13a) (100 mg, 0.75 mmol) and compound (B) (146 mg, 0.75 mmol) in THF (5 mL) was stirred at 70° C. 4 h. The reaction mixture was cooled down to 23° C. and diluted with EtOAc (10 mL), filtered the solid. The solid was diluted with DMF, purified by RP column chromatography to afford 1-([1,1'-biphenyl]-

4-yl)-3-(1,1-dioxido-2,3-dihydrothiophen-3-yl)urea (13) (22.6 mg, 20.3%) as a white solid. $^{1}$H NMR (400 MHz, DMSO-$d_6$) δ 8.72 (s, 1H), 7.61 (d, J=7.0 Hz, 2H), 7.57 (d, J=8.6 Hz, 2H), 7.49 (d, J=8.6 Hz, 2H), 7.42 (t, J=7.7 Hz, 2H), 7.30 (t, J=7.3 Hz, 1H), 7.19 (dd, J=6.6, 2.0 Hz, 1H), 6.91 (dd, J=6.6, 2.9 Hz, 1H), 6.82 (d, J=8.2 Hz, 1H), 5.20-5.09 (m, 1H), 3.70 (dd, J=13.7, 7.8 Hz, 1H), 3.16 (dd, J=13.7, 4.2 Hz, 1H). LCMS: 1.659 min, $C_{17}H_{16}N_2O_3S_2$; [M+1]=329.1, [M+23]=351.1.

Example 14

Synthesis of N-(1,1-dioxido-2,3-dihydrothiophen-3-yl)-2-naphthamide (14)

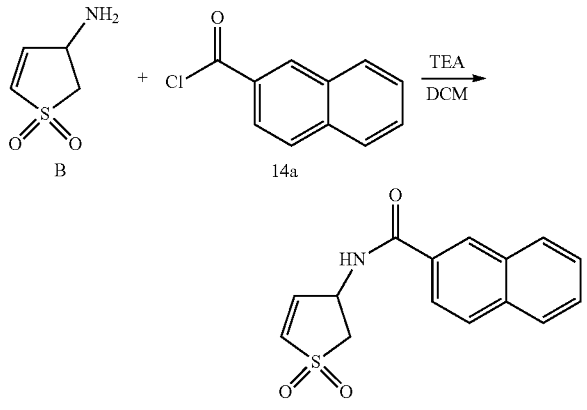

B 14a

14

To a solution of compound (B) (Example B) (50 mg, 0.38 mmol) in DCM (2 mL) was added 2-naphthoyl chloride (72 mg, 0.38 mmol) and DIEA (97 mg, 0.75 mmol). The mixture was stirred at 23° C. for 1 h. The mixture was diluted with water (40 mL) and extracted with DCM (20 mL×3). The combined organic phases were washed with water (30 mL) and brine (30 mL), dried over $Na_2SO_4$, concentrated, and purified by Prep-TLC (DCM/MeOH=10/1) to afford N-(1,1-dioxido-2,3-dihydrothiophen-3-yl)-2-naphthamide (14) (32.5 mg, 29.8%) as a white solid. $^{1}$H NMR (400 MHz, DMSO-$d_6$) δ 9.25 (s, 1H), 8.50 (d, J=1.6 Hz, 1H), 8.07-7.90 (m, 4H), 7.68-7.56 (m, 2H), 7.27 (dd, J=6.7, 2.2 Hz, 1H), 6.96 (dd, J=6.6, 2.6 Hz, 1H), 5.50-5.41 (m, 1H), 3.85 (dd, J=13.7, 8.0 Hz, 1H), 3.32-3.24 (m, 1H). LCMS: 1.409 min, $C_{15}H_{13}NO_3S$; [M+1]=288.1.

Example 15

Synthesis of N-(1,1-dioxido-2,3-dihydrothiophen-3-yl)-2-(naphthalen-2-yl)acetamide (15)

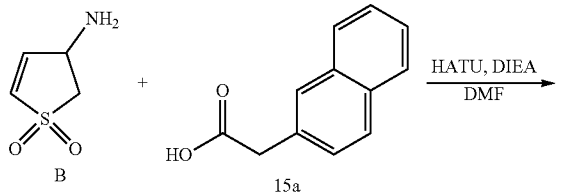

B 15a

-continued

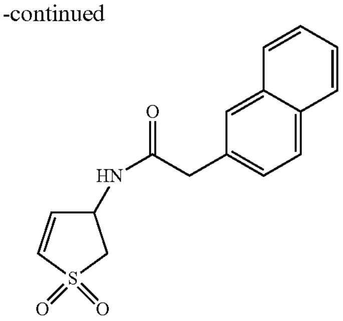

15

To a solution of compound (B) (Example B) (50 mg, 0.38 mmol) in DMF (2 mL) was added 2-(naphthalen-2-yl)acetic acid (15a) (70 mg, 0.38 mmol), HATU (210 mg, 0.56 mmol) and DIEA (97 mg, 0.75 mmol). The mixture was stirred at 23° C. overnight. The mixture was diluted with water (40 mL), extracted with EtOAc (20 mL×3). The combined organic phase was washed with water (30 mL) and brine (30 mL), dried over $Na_2SO_4$, concentrated and purified by Prep-TLC twice (PE:EtOAc=1:1) to afford N-(1,1-dioxido-2,3-dihydrothiophen-3-yl)-2-(naphthalen-2-yl)acetamide (15) (48.0 mg, 42.4% yield) as a white solid. $^{1}$H NMR: (400 MHz, DMSO-$d_6$) δ 8.83 (d, J=7.6 Hz, 1H), 7.91-7.82 (m, 3H), 7.75 (s, 1H), 7.53-7.45 (m, 2H), 7.43 (dd, J=8.4, 1.7 Hz, 1H), 7.21 (dd, J=6.7, 2.1 Hz, 1H), 6.83 (dd, J=6.7, 2.8 Hz, 1H), 5.20-5.11 (m, 1H), 3.72 (dd, J=13.8, 8.1 Hz, 1H), 3.63 (s, 2H), 3.03 (dd, J=13.8, 4.5 Hz, 1H). LCMS: 1.424 min, $C_{16}H_{15}NO_3S$; [M−1]=300.1.

Example 16

Synthesis of N-(1,1-dioxido-2,3-dihydrothiophen-3-yl)-N-methylnaphthalene-2-sulfonamide (16)

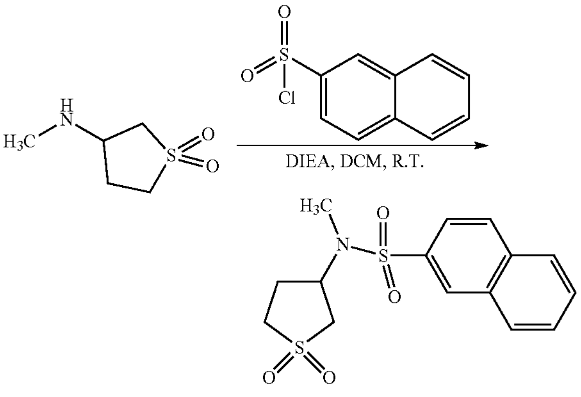

16

To a solution of 3-(methylamino)tetrahydrothiophene 1,1-dioxide (150 mg, 1.01 mmol) in DCM (3 mL) was added DIEA (273 mg, 1.2 mmol) at 0° C. Naphthalene-2-sulfonyl chloride (228 mg, 1.01 mmol) was added slowly at 0° C. and the reaction was stirred at 23° C. for 1 h. The mixture was diluted with water (30 mL) and extracted with DCM (20 mL×3). The organic phase was washed with brine (30 mL), dried over $Na_2SO_4$, and concentrated in vacuo. The residue was purified by Prep-TLC (DCM/MeOH=10/1) to afford N-(1,1-dioxido-2,3-dihydrothiophen-3-yl)-N-methylnaphthalene-2-sulfonamide (16) (32 mg, 9.4% yield) as a white solid. $^1$H NMR (400 MHz, chloroform-d) δ 8.39 (d, J=1.8 Hz, 1H), 8.03-7.96 (m, 2H), 7.94 (d, J=7.9 Hz, 1H), 7.77-7.63 (m, 3H), 4.96-4.85 (m, 1H), 3.23-3.15 (m, 1H), 3.05-2.94 (m, 2H), 2.86 (s, 3H), 2.76-2.67 (m, 1H), 2.37-2.28 (m, 1H), 2.27-2.14 (m, 1H). LCMS: 1.687 min, $C_{15}H_{17}NO_4S_2$; [M+1]=340.1, [M+18]=357.2.

Example 17

Synthesis of 1,1-dioxido-2,3-dihydrothiophen-3-yl [1,1'-biphenyl]-4-sulfonate (17)

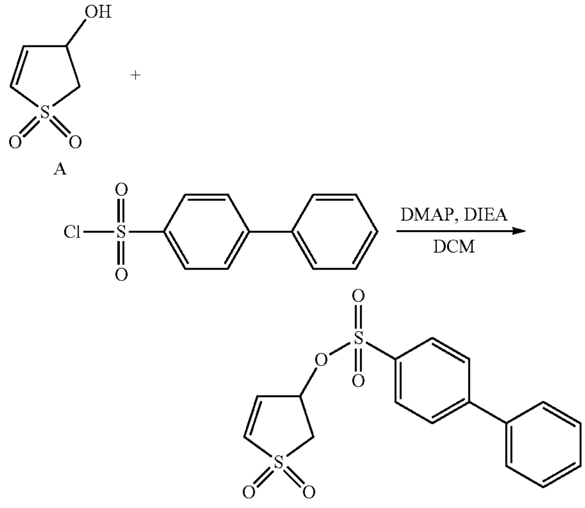

A

17

To a solution of compound (A) (Example A) (50 mg, 0.37 mmol) in DCM (2 mL) was added DMAP (2.2 mg, 0.018 mmol) and DIEA (58.1 mg, 0.45 mmol) at 23° C., [1,1'-biphenyl]-4-sulfonyl chloride (103.6 mg, 0.41 mmol) was added at 0° C. The mixture was stirred at 23° C. for 2 h. The reaction mixture was diluted with water (20 mL) and extracted with DCM (10 mL×2). The combined organic phase was washed with water (10 mL) and brine (20 mL), dried over $Na_2SO_4$, concentrated in vacuo, and purified by silica gel column chromatography (PE/EtOAc=100/1 to 5/1, v/v) to afford 1,1-dioxido-2,3-dihydrothiophen-3-yl [1,1'-biphenyl]-4-sulfonate (17) (30 mg, 23.0% yield) as a white solid. $^1$H NMR (400 MHz, chloroform-d) δ 7.99 (d, J=8.2 Hz, 2H), 7.81 (d, J=8.2 Hz, 2H), 7.62 (dd, J=7.4, 1.8 Hz, 2H), 7.55-7.43 (m, 3H), 6.85 (dd, J=6.9, 1.5 Hz, 1H), 6.70 (dd, J=6.8, 2.8 Hz, 1H), 5.79-5.73 (m, 1H), 3.62 (dd, J=14.2, 7.6 Hz, 1H), 3.32 (dd, J=14.2, 3.9 Hz, 1H). LCMS: 2.051 min, $C_{16}H_{14}O_5S_2$; [M+18]=368.0, [M+23]=373.0.

Example 18

Synthesis of 1,1-dioxido-2,3-dihydrothiophen-3-yl 4-phenoxybenzenesulfonate (18)

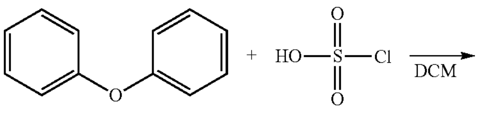

18a

-continued

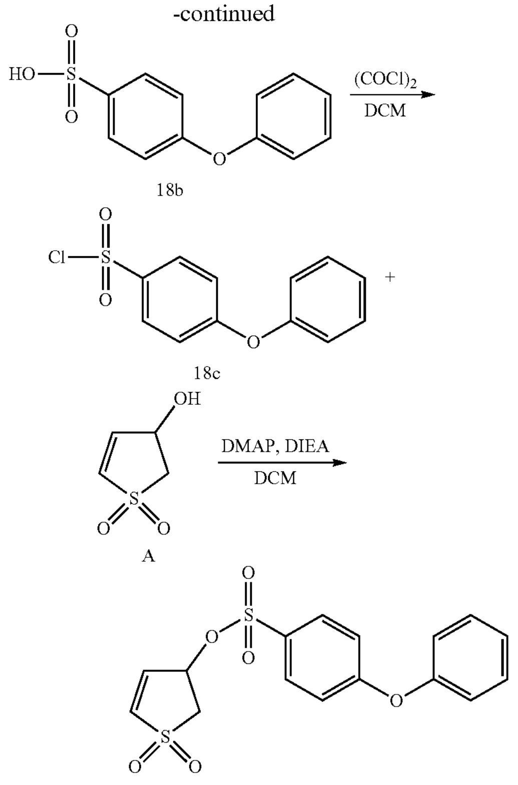

18b

18c

A

18

Step 1. Synthesis of 4-phenoxybenzenesulfonic acid (18b)

To a solution of oxydibenzene (18a) (2.0 g, 11.75 mmol) in DCM (60 mL) was added sulfurochloridic acid (1.37 g, 11.75 mol) at 0° C. The mixture was stirred at 23° C. for 2 h. The mixture was concentrated in vacuum to afford 4-phenoxybenzenesulfonic acid (18b) (2.8 g, 95.2%) as a yellow oil. $^1$H NMR: (400 MHz, dhloroform-d) δ 9.89 (s, 1H), 7.75 (d, J=8.4 Hz, 2H), 7.36 (t, J=7.8 Hz, 2H), 7.17 (t, J=7.5 Hz, 1H), 7.03-6.99 (m, 2H), 6.92 (d, J=8.4 Hz, 2H).

Step 3. Synthesis of 4-phenoxybenzenesulfonyl chloride (18c)

To a solution of 4-phenoxybenzenesulfonic acid (18b) (500.0 mg, 2.0 mmol) in DCM (5 mL) was added $(COCl)_2$ (304.3 mL, 2.4 mmol) at 0° C. The mixture was stirred at 23° C. for 2 h. The reaction mixture was diluted with water (20 mL), extracted with DCM (10 mL×2). The combined organic phase was washed by water (20 mL) and brine (20 mL), dried over $Na_2SO_4$, concentrated in vacuo and purified by silica gel column chromatography (PE/EtOAc=200/1 to 50/1, v/v) to afford 4-phenoxybenzenesulfonyl chloride (18c) (351 mg, 65.2%) as a colorless oil. $^1$H NMR: (400 MHz, dhloroform-d) δ 8.01-7.95 (m, 2H), 7.49-7.42 (m, 2H), 7.31-7.26 (m, 1H), 7.14-7.04 (m, 4H).

Step 4. Synthesis of 1,1-dioxido-2,3-dihydrothiophen-3-yl 4-phenoxybenzenesulfonate (18)

To a solution of compound (A) (Example A) (50 mg, 0.37 mmol) in DCM (2 mL) was added DMAP (2.2 mg, 0.018 mmol), DIEA (58.1 mg, 0.45 mmol) and 4-phenoxybenzenesulfonyl chloride (18c) (116.8 mg, 0.41 mmol) at 0° C. The reaction mixture was stirred at 23° C. for 2 h. The mixture was diluted with water (20 mL) and extracted with DCM (10 mL×2). The combined organic phase was washed with water (20 mL) and brine (20 mL), dried over $Na_2SO_4$, concentrated in vacuo and purified by silica gel column chromatography (PE/EtOAc=5/1, v/v) and Prep-TLC (PE/EtOAc=2/1, v/v) to afford 1,1-dioxido-2,3-dihydrothiophen-3-yl 4-phenoxybenzenesulfonate (18) (15.0 mg, 23.3%) as a white solid. $^1$H NMR (400 MHz, Chloroform-d) δ 7.86 (d, J=8.9 Hz, 2H), 7.45 (t, J=7.1 Hz, 2H), 7.29 (d, J=6.7 Hz, 1H), 7.10 (dd, J=8.6, 3.3 Hz, 4H), 6.84 (d, J=6.7 Hz, 1H), 6.69 (dd, J=6.7, 2.6 Hz, 1H), 5.74-5.67 (m, 1H), 3.59 (dd, J=14.2, 7.6 Hz, 1H), 3.29 (dd, J=14.2, 3.9 Hz, 1H). LCMS: 2.075 min, $C_{16}H_{14}O_6S_2$; [M+18]=384.1, [M+23]=389.0.

Examples 19 and 20

Synthesis of N-(1,1-dioxido-4,5-dihydrothiophen-3-yl)-N-methylnaphthalene-2-sulfonamide (19) and N-(1,1-dioxido-2,5-dihydrothiophen-3-yl)-N-methylnaphthalene-2-sulfonamide (20)

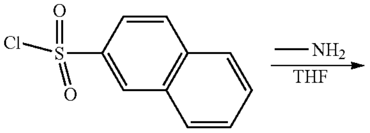

19a

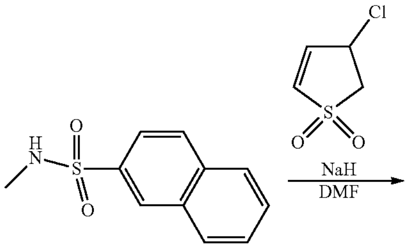

19b

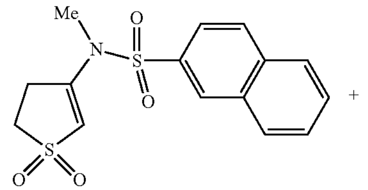

19

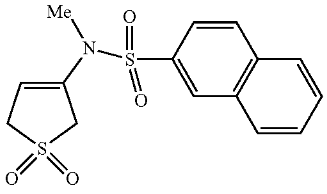

20

Step 1. Synthesis of N-methylnaphthalene-2-sulfonamide (19b)

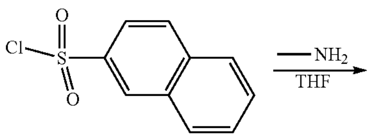

19a

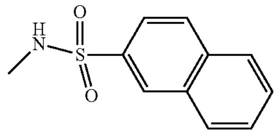

19b

To a solution of naphthalene-2-sulfonyl chloride (19a) (200 mg, 0.88 mmol) in THF (3 mL) was added methylamine in THF (2 mL, 2M, 4 mmol) at 0° C. The mixture was stirred at 23° C. for 1 h. The solvent was removed. The crude residue was diluted with water (40 mL), extracted with EtOAc (20 mL×3). The combined organic phase was washed with brine (40 mL), dried over $Na_2SO_4$, and concentrated to afford N-methylnaphthalene-2-sulfonamide (19b) (190 mg, 97.3%) as a white solid. $^1$H NMR: (400 MHz, DMSO-$d_6$) δ 8.41 (d, J=1.8 Hz, 1H), 8.15 (t, J=8.0 Hz, 2H), 8.04 (d, J=7.3 Hz, 1H), 7.80 (dd, J=8.6, 1.9 Hz, 1H), 7.73-7.64 (m, 2H), 7.53 (s, 1H), 2.43 (s, 3H).

Step 2. Synthesis of N-(1,1-dioxido-4,5-dihydrothiophen-3-yl)-N-methylnaphthalene-2-sulfonamide (19) and N-(1,1-dioxido-2,5-dihydrothiophen-3-yl)-N-methylnaphthalene-2-sulfonamide (20)

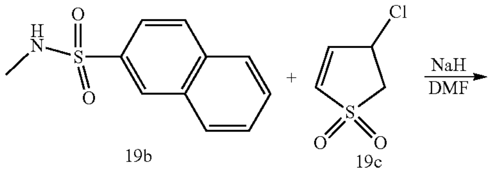

19b 19c

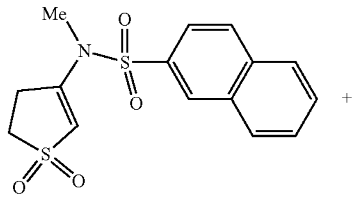

19

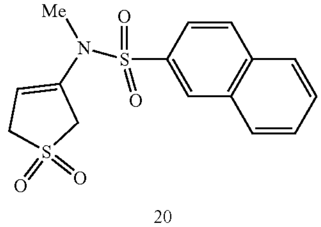

20

To a solution of N-methylnaphthalene-2-sulfonamide (19b) (100 mg, 0.46 mmol) in DMF (3 mL) was added NaH (60%, w/w, dispersed in oil, 27.1 mg, 0.68 mmol) at 0° C.

The mixture was stirred at 23° C. for 30 min, 3-chloro-2,3-dihydrothiophene 1,1-dioxide (19c) (70 mg, 0.46 mmol) was added and the resulting mixture was stirred at 23° C. for 5 min. The mixture was diluted with water (40 mL) and extracted with EtOAc (20 mL×3). The combined organic phase was washed with water (30 mL) and brine (30 mL), dried over $Na_2SO_4$, concentrated, and purified by Prep-HPLC to afford N-(1,1-dioxido-4,5-dihydrothiophen-3-yl)-N-methylnaphthalene-2-sulfonamide (19) (31.3 mg, 20.5% yield) and N-(1,1-dioxido-2,5-dihydrothiophen-3-yl)-N-methylnaphthalene-2-sulfonamide (20) (6.1 mg, 4.0% yield) as a yellow solid.

N-(1,1-Dioxido-4,5-dihydrothiophen-3-yl)-N-methyl-naphthalene-2-sulfonamide (19): $^1$H NMR: (400 MHz, DMSO-$d_6$) δ8.68 (d, J=2.0 Hz, 1H), 8.23 (dd, J=16.8, 8.4 Hz, 2H), 8.11 (d, J=8.0 Hz, 1H), 7.87 (dd, J=8.7, 2.0 Hz, 1H), 7.81-7.71 (m, 2H), 6.46 (d, J=1.4 Hz, 1H), 3.39-3.34 (m, 2H), 3.29-3.22 (m, 5H). LCMS: 1.537 min, $C_{15}H_{15}NO_4S_2$; [M+1]=337.95.

N-(1,1-Dioxido-2,5-dihydrothiophen-3-yl)-N-methyl-naphthalene-2-sulfonamide (20): LCMS: 1.624 min, $C_{15}H_{15}NO_4S_2$; [M+1]=337.95. $^1$H NMR: (400 MHz, DMSO-$d_6$) δ8.54 (d, J=1.9 Hz, 1H), 8.23 (d, J=8.0 Hz, 1H), 8.17 (d, J=8.7 Hz, 1H), 8.09 (d, J=8.0 Hz, 1H), 7.81 (dd, J=8.7, 2.0 Hz, 1H), 7.78-7.68 (m, 2H), 5.61-5.55 (m, 1H), 4.15 (d, J=1.7 Hz, 2H), 3.92-3.86 (m, 2H), 2.99 (s, 3H). LCMS: 1.624 min, $C_{15}H_{15}NO_4S_2$; [M+1]=337.95.

Example 21

Synthesis of (S)-1,1-Dioxido-2,3-dihydrothiophen-3-yl 4-phenoxybenzenesulfonate (21)

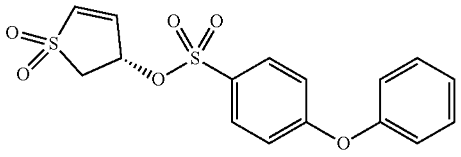 [SMILES: O=S1(=O)C=C[C@H](OS(=O)(=O)c2ccc(Oc3ccccc3)cc2)C1]

1,1-Dioxido-2,3-dihydrothiophen-3-yl 4-phenoxybenzenesulfonate (1) prepared as described in Example 1 (500.0 mg, 1.86 mmol) was purified by chiral separation to afford (S)-1,1-dioxido-2,3-dihydrothiophen-3-yl 4-phenoxybenzenesulfonate (21) (100.4 mg, 20% yield) as white solid. Chiral separation method: ColunmChiralcel®0J-H, column size: 4.6 mm×25 cm, 5 m, Injection: 5 μL, mobile phase: 100% EtOH, Flow rate: 1.0 mL/min, wavelength: UV 254 nm, temperature: 35° C., Sample solution: 1.0 mg/mL in MeOH (50%) and EtOH (50%), HPLC equipment: Shimadzu 2020. $^1$H NMR (400 MHz, $CDCl_3$) δ 7.86 (d, J=8.8 Hz, 2H), 7.45 (t, J=7.9 Hz, 2H), 7.29 (t, J=7.4 Hz, 1H), 7.14-7.06 (m, 4H), 6.85 (dd, J=6.8, 1.5 Hz, 1H), 6.69 (dd, J=6.7, 2.8 Hz, 1H), 5.73-5.69 (m, 1H), 3.59 (dd, J=14.2, 7.6 Hz, 1H), 3.29 (dd, J=14.2, 3.9 Hz, 1H). LCMS: m/z: 384.1[M+18]+. HPLC: 11.610 min, m/z, 98.76% at 254 nm, 98.68% at 214 nm. ee=95.28%.

Example 22

Synthesis of (R)-1,1-Dioxido-2,3-dihydrothiophen-3-yl 4-phenoxybenzenesulfonate (22)

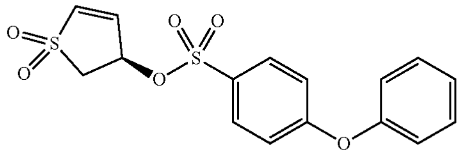 [SMILES: O=S1(=O)C=C[C@@H](OS(=O)(=O)c2ccc(Oc3ccccc3)cc2)C1]

1,1-Dioxido-2,3-dihydrothiophen-3-yl 4-phenoxybenzenesulfonate (1) prepared as described in Example 1 (500.0 mg, 1.86 mmol) was purified by chiral separation to afford (R)-1,1-dioxido-2,3-dihydrothiophen-3-yl 4-phenoxybenzenesulfonate (22) (100.5 mg, 20% yield) as white solid. Chiral separation method:Column:Chiralcel®0J-H, column size: 4.6 mm×25 cm, 5 μm, Injection: 5 μL, mobile phase: 100% EtOH, Flow rate: 1.0 mL/min, wavelength: UV 254 nm, temperature: 35° C., Sample solution: 1.0 mg/mL in MeOH (50%) and EtOH (50%), HPLC equipment: Shimadzu 2020. $^1$H NMR (400 MHz, $CDCl_3$) δ 7.86 (d, J=9.0 Hz, 2H), 7.45 (t, J=7.9 Hz, 2H), 7.29 (t, J=7.4 Hz, 1H), 7.14-7.06 (m, 4H), 6.85 (dd, J=6.7, 1.6 Hz, 1H), 6.69 (dd, J=6.8, 2.8 Hz, 1H), 5.76-5.66 (m, 1H), 3.59 (dd, J=14.2, 7.7 Hz, 1H), 3.29 (dd, J=14.2, 3.9 Hz, 1H). LCMS: m/z: 384.1[M+18]+. HPLC: 11.595 min, m/z, 99.07% at 254 nm, 98.78% at 214 nm. ee=95.45%.

Example 23

Synthesis of 1,1-Dioxido-2,3-dihydrothiophen-3-yl 4-phenoxybenzoate (23)

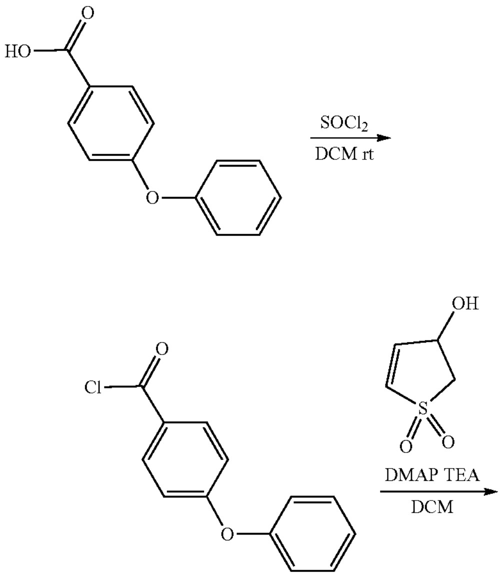

23a

-continued

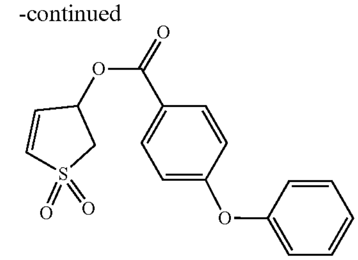

23

Step 1. Synthesis of 4-(cyclohexyloxy)benzenesulfonyl chloride (23a)

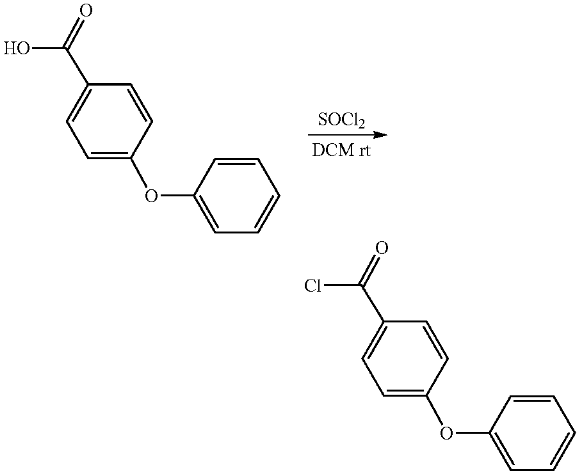

123a

To a solution of 4-phenoxybenzoic acid (240 mg, 1.12 mmol) in DCM (5 mL) was added thionyl chloride (199 mg, 1.68 mmol) at 0° C., the mixture was stirred at 23° C. for 2 h. The mixture solution was concentrated under vacuum to afford 4-(cyclohexyloxy)benzenesulfonyl chloride (23a) (260 mg, 99.9%) as a white solid.

Step 2. Synthesis of 1,1-dioxido-2,3-dihydrothiophen-3-yl 4-phenoxybenzoate (23)

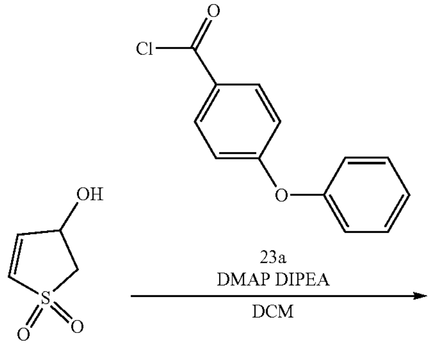

A

-continued

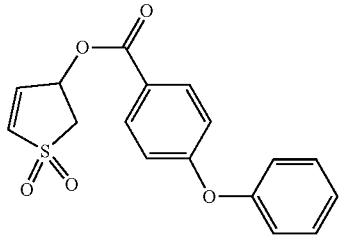

23

To a solution of compound (A) (52.5 mg, 0.39 mmol) in DCM (3 mL) was added DMAP (4.9 mg, 0.04 mmol), DIPEA (101 mg, 0.78 mmol) and 4-(cyclohexyloxy)benzenesulfonyl chloride (23a) (100 mg, 0.43 mmol) at 0° C. The mixture was stirred at 23° C. for 1 h and diluted with water (10 mL) and extracted with DCM (10 mL×2). The combined organic layers were washed with brine, dried over $Na_2SO_4$, filtered, and concentrated. The residue was purified by Prep-TLC (EtOAc/PE=3/1) to afford 1,1-dioxido-2,3-dihydrothiophen-3-yl 4-phenoxybenzoate (23) (100 mg, 77.7% yield) as a white solid. LCMS: m/z: 348.05 [M+18]+. HPLC: 5.315 min, m/z, 98.58% at 214 nm, 98.59% at 254 nm. $^1H$ NMR (400 MHz, DMSO-$d_6$) δ 7.98 (d, J=8.8 Hz, 2H), 7.47 (t, J=7.8 Hz, 3H), 7.25 (t, J=7.4 Hz, 1H), 7.14-7.04 (m, 5H), 6.19-6.12 (m, 1H), 3.85 (dd, J=14.6, 7.6 Hz, 1H), 3.51 (dd, J=14.6, 2.8 Hz, 1H).

Example 24

Synthesis of 1,1-dioxido-2,3-dihydrothiophen-3-yl [1,1'-biphenyl]-4-carboxylate (24)

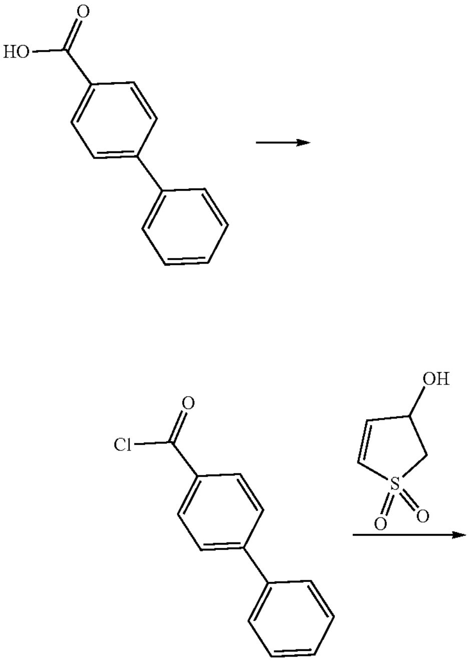

24a

-continued

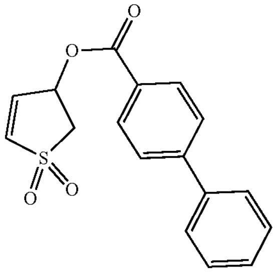

24

Step 1. Synthesis of 4-(cyclohexyloxy)benzenesulfonyl chloride

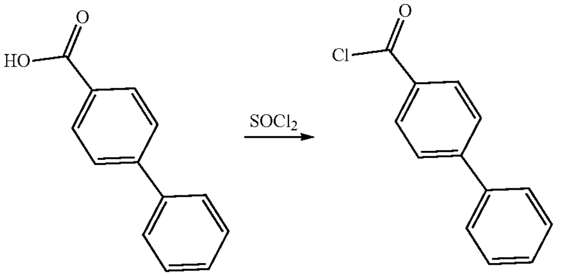

24a

To a solution of [1,1'-biphenyl]-4-carboxylic acid (50 mg, 0.25 mmol) in DCM (3 mL) was added thionyl chloride (45 mg, 0.38 mmol) at 0° C. The mixture was stirred at 23° C. for 2 h. The mixture was concentrated under vacuum to afford 4-(cyclohexyloxy)benzenesulfonyl chloride (24a) (50 mg, 92.3% yield) as a white solid.

Step 2. Synthesis of 1,1-dioxido-2,3-dihydrothiophen-3-yl [1,1'-biphenyl]-4-carboxylate (24)

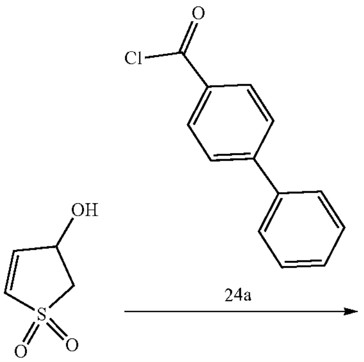

A

-continued

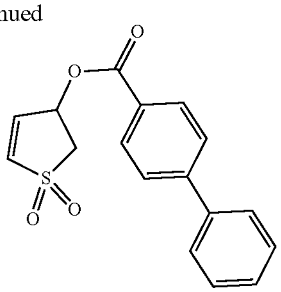

24

To a solution of compound A (28.2 mg, 0.21 mmol) in DCM (3 mL) was added DMAP (2.5 mg, 0.02 mmol), DIPEA (40.7 mg, 0.32 mmol) and 4-(cyclohexyloxy)benzenesulfonyl chloride (24a) (50 mg, 0.23 mmol) at 0° C. The mixture was stirred at 23° C. for 1 h and diluted with water (10 mL) and extracted with DCM (10 mL×2). The combined organic layers were washed with brine, dried over $Na_2SO_4$, filtered, and concentrated. The residue was purified by Prep-TLC (EtOAc/PE=3/1) to afford 1,1-dioxido-2,3-dihydrothiophen-3-yl [1,1'-biphenyl]-4-carboxylate (24) (15.3 mg, 23.2%) as a white solid. LCMS: m/z: 332.05 [M+18]+. HPLC: 4.534 min, m/z, 98.49% at 214 nm, 99.85% at 254 nm. $^1$H NMR (400 MHz, DMSO-$d_6$) δ 8.09-8.00 (m, 2H), 7.90-7.81 (m, 2H), 7.78-7.71 (m, 2H), 7.55-7.41 (m, 4H), 7.11 (dd, J=6.8, 3.2 Hz, 1H), 6.20 (dtd, J=7.6, 3.0, 1.2 Hz, 1H), 3.88 (dd, J=14.4, 7.6 Hz, 1H), 3.57 (dd, J=14.6, 2.8 Hz, 1H).

Example 25

Synthesis of 1,1-dioxido-2,3-dihydrothiophen-3-yl 3-phenoxybenzenesulfonate (25)

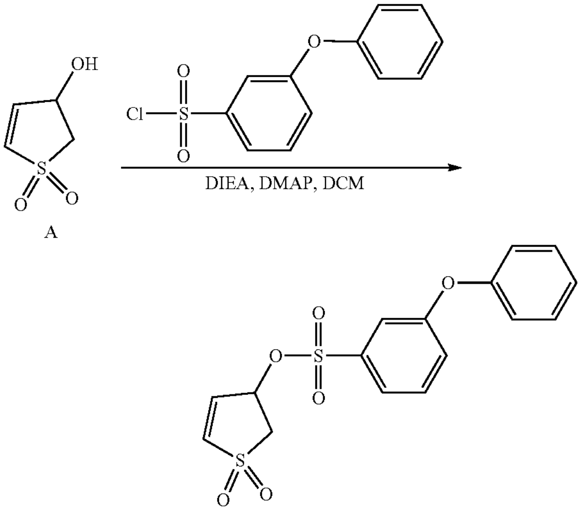

A

25

To a solution of compound (A) (100 mg, 0.745 mmol) in DCM (3 mL) was added DIPEA (145 mg. 1.12 mmol), DMAP (9.1 mg, 0.075 mmol), and 3-phenoxybenzenesulfonyl chloride (220 mg, 0.82 mmol). The resulting mixture was stirred at 23° C. for 15 min. The reaction mixture was diluted with water (20 mL) and extracted by DCM (10 mL×2). The combined organic phase was washed with brine (30 mL), dried over $Na_2SO_4$, and concentrated in vacuo to give the crude product which was purified by silica gel column chromatography (PE/EtOAc=20/1 to 5/1, v/v) to afford 1,1-dioxido-2,3-dihydrothiophen-3-yl 3-phenoxybenzenesulfonate (25) (15.2 mg, 5.7% yield) as a white solid. LCMS: m/z: 383.95 [M+18]+. HPLC: 11.54 min, m/z, 99.9% at 214 nm. $^1$H NMR (400 MHz, chloroform-d) δ 7.61 (dt, J=7.8, 1.4 Hz, 1H), 7.54 (t, J=8.0 Hz, 1H), 7.48 (t, J=2.2 Hz, 1H), 7.46-7.39 (m, 2H), 7.34-7.28 (m, 1H), 7.24 (t, J=7.6 Hz, 1H), 7.10-7.02 (m, 2H), 6.85 (dd, J=6.8, 1.6 Hz, 1H), 6.66 (dd, J=6.8, 2.8 Hz, 1H), 5.75-5.67 (m, 1H), 3.58 (dd, J=14.2, 7.8 Hz, 1H), 3.27 (dd, J=14.2, 3.8 Hz, 1H).

Example 26

Synthesis of 1,1-dioxido-2,3-dihydrothiophen-3-yl [1,1'-biphenyl]-3-sulfonate (26)

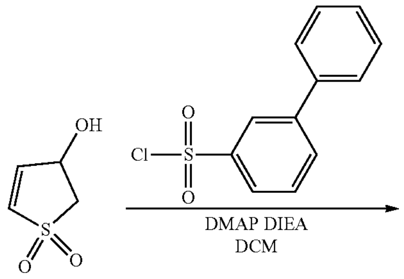

A

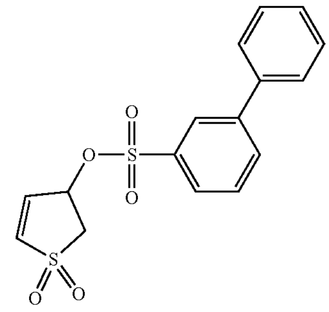

26

To a solution of compound (A) (97 mg, 0.723 mmol) in DCM (3 mL) was added DMAP (8.8 mg, 0.072 mmol), DIPEA (187 mg, 1.45 mmol), and 4-cyclohexylbenzenesulfonyl chloride (183 mg, 0.723 mmol) at 23° C. The reaction mixture was stirred at 23° C. for 1.0 h and diluted with water (10 mL) and extracted with DCM (10 mL). The organic layer was washed with brine (20 mL), dried over $Na_2SO_4$, concentrated in vacuo. The crude product was purified by Prep-TLC (PE:EtOAc=2:1) to afford 1,1-dioxido-2,3-dihydrothiophen-3-yl [1,1'-biphenyl]-3-sulfonate (26) (21 mg, 8.3% yield) as a white solid. LCMS: m/z: 368.0 [M+18]+. HPLC: 12.507 min, m/z, 99.84% at 254 nm, 99.84% at 214 nm. $^1$H NMR (400 MHz, DMSO-$d_6$) δ 8.21-8.14 (m, 2H), 8.00 (d, J=7.8 Hz, 1H), 7.83 (dd, J=14.0, 7.4 Hz, 3H), 7.52 (dq, J=22.2, 7.4 Hz, 4H), 6.91 (dd, J=6.8, 3.4 Hz, 1H), 5.99 (dt, J=6.6, 2.8 Hz, 1H), 3.72 (dd, J=14.6, 7.8 Hz, 1H), 3.42 (dd, J=14.8, 2.2 Hz, 1H).

Example 27

Synthesis of 1,1-dioxido-2,3-dihydrothiophen-3-yl 4-(benzyloxy)benzenesulfonate (27)

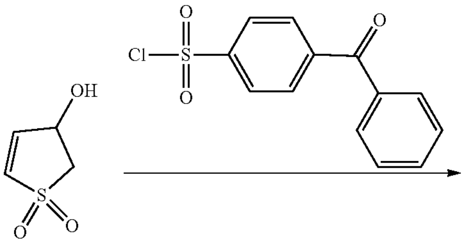

A

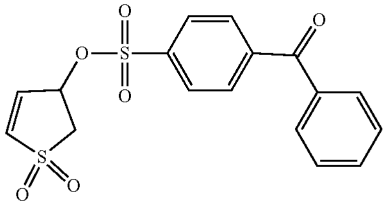

27

To a solution of compound A (90 mg, 0.67 mmol) in DCM (3 mL) was added 4-benzoylbenzenesulfonyl chloride (208 g, 0.74 mmol), DIEA (129 mL, 1 mmol), and DMAP (8.6 mg, 0.07 mmol) at 0° C. The reaction mixture was stirred at 0° C. for 30 min. The mixture was diluted with water (10 mL) and extracted with DCM (10 mL×2). The combined organic layer was washed with brine, dried over $Na_2SO_4$, filtered, and concentrated. The residue was purified by silica gel column chromatography (PE:EtOAc=20/1 to 5/1, v/v) to afford 1,1-dioxido-2,3-dihydrothiophen-3-yl 4-(benzyloxy) benzenesulfonate (27) (25 mg, 10%) as a white solid. LCMS: m/z: 398.00 $[M+18]^+$. HPLC: 11.54 min, m/z, 98.05% at 214 nm, 98.57% at 254 nm. $^1$H NMR (400 MHz, DMSO-$d_6$) δ 7.95-7.88 (m, 2H), 7.49-7.34 (m, 6H), 7.32-7.27 (m, 2H), 6.83 (dd, J=6.8, 3.4 Hz, 1H), 5.82 (dt, J=7.8, 2.8 Hz, 1H), 5.25 (s, 2H), 3.67 (dd, J=14.6, 7.8 Hz, 1H), 3.28 (dd, J=14.8, 2.4 Hz, 1H).

Example 28

Synthesis of 1,1-dioxido-2,3-dihydrothiophen-3-yl 4-benzylbenzenesulfonate (28)

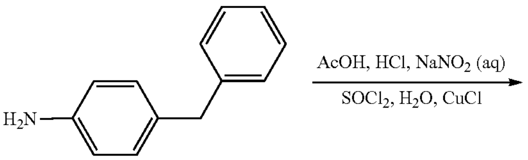

-continued

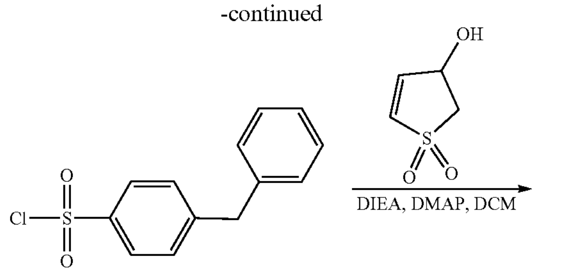

28a

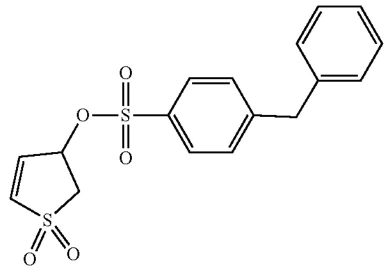

28

Step 1. Synthesis of 1-(chlorodioxo-17-methyl)-4-ethylbenzene (28a)

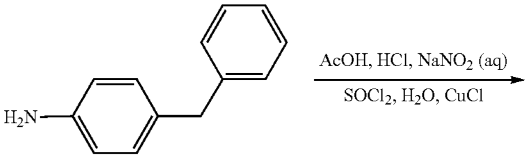

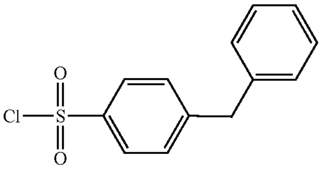

28a

To a three-necked bottle was added 4-benzylaniline (500 mg, 2.73 mmol), AcOH (5 mL), concentrated HCl (1.1 mL, 13.65 mmol) and aqueous $NaNO_2$ (207 mg, 3.0 mmol) at 0° C. The mixture was stirred at 0° C. for 30 min. Meantime, to a solution of copper(I) chloride (109 mg, 1.1 mmol) in water (30 mL) was added thionyl chloride (1.6 g, 13.65 mmol) at 0° C. After stirring at 0° C. for 30 min, the above diazonium salt mixture was added at 0° C. and stirred at 23° C. for 20 min. The reaction mixture was diluted with water (30 mL) and extracted with EtOAc (30 mL×2). The organic phase was washed by brine, dried over $Na_2SO_4$, and concentrated in vacuo to afford the crude product which was purified by silica gel column chromatography (PE/EtOAc=50/1, v/v) to afford 1-(chlorodioxo-17-methyl)-4-ethylbenzene (28a) (440 mg, 60.4% yield) as a yellow oil.

Step 2. 1,1-dioxido-2,3-dihydrothiophen-3-yl 4-benzylbenzenesulfonate (28)

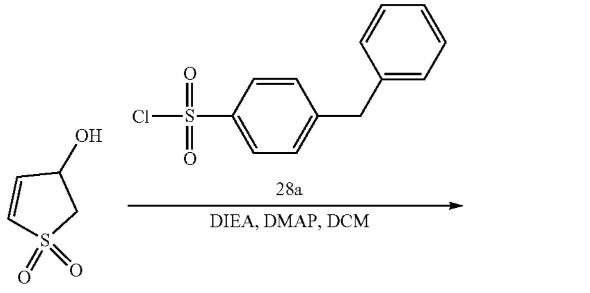

A

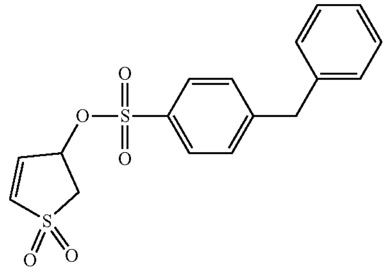

28

To a solution of compound A (46 mg, 341 μmol) in DCM (3 mL) was added DIPEA (66 mg, 512 μmol), DMAP (4.2 mg, 34 μmol) and 1-(chlorodioxo-17-methyl)-4-ethylbenzene (28a) (100 mg, 375 μmol). The resulting mixture was stirred at 23° C. for 15 min. The reaction mixture was diluted with water (20 mL) and extracted by DCM (10 mL×2). The combined organic phase was washed with brine (30 mL), dried over $Na_2SO_4$, and concentrated in vacuo to give the crude product which was purified by silica gel column chromatography (PE/EtOAc=20/1 to 5/1, v/v) and washed by methanol to afford 1,1-dioxido-2,3-dihydrothiophen-3-yl 4-benzylbenzenesulfonate (28) (15 mg, 12.1% yield) as a white solid. LCMS: m/z: 382.0 [M+18]+. HPLC: 12.730 min, m/z, 99.2% at 254 nm, 99.2% at 214 nm. $^1$H NMR (400 MHz, chloroform-d) δ 7.83 (d, J=8.4 Hz, 2H), 7.41 (d, J=8.1 Hz, 2H), 7.33 (dd, J=8.0, 6.5 Hz, 2H), 7.28 (d, J=1.3 Hz, 1H), 7.20-7.14 (m, 2H), 6.83 (dd, J=6.8, 1.6 Hz, 1H), 6.66 (dd, J=6.8, 2.8 Hz, 1H), 5.72-5.67 (m, 1H), 4.09 (s, 2H), 3.57 (dd, J=14.2, 7.6 Hz, 1H), 3.26 (dd, J=14.2, 3.9 Hz, 1H).

Example 29

Synthesis of 1,1-dioxido-2,3-dihydrothiophen-3-yl 4-(phenoxymethyl)benzenesulfonate (29)

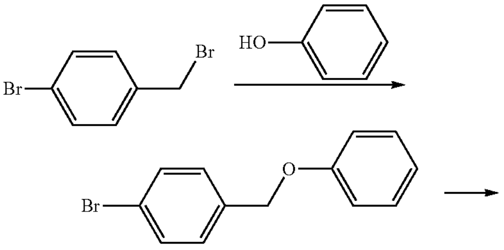

1

-continued

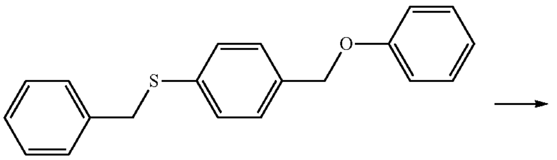

2

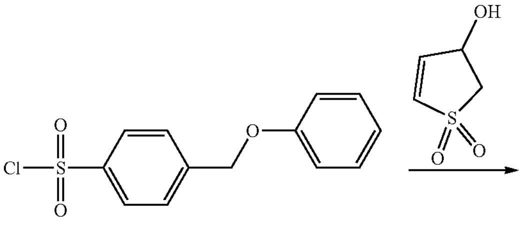

3

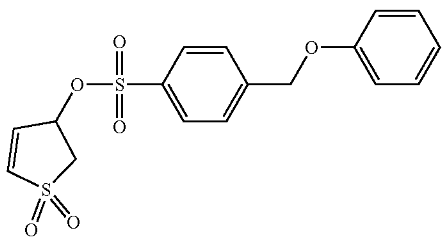

GEn-1937

Step 1. Synthesis of 1-bromo-4-(phenoxymethyl)benzene (29a)

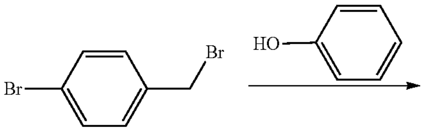

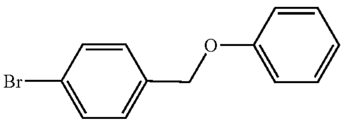

29a

To a solution of 1-bromo-4-(bromomethyl)benzene (5.0 g, 20.01 mmol) in DMF (30 mL) was added phenol (1.9 g, 20.01 mmol) and $K_2CO_3$ (3.4 g, 24.01 mmol), and the mixture was stirred at 20° C. for 8 h. Water (300 mL) was added and the mixture extracted with EtOAc (100 mL). The organic layers were washed with water and brine (300 mL), dried over $Na_2SO_4$, and concentrated to afford 1-bromo-4-(phenoxymethyl)benzene (29a) (4 g, 76% yield) as a colorless oil.

Step 2. Synthesis benzyl(4-(phenoxymethyl)phenyl)sulfane (29b)

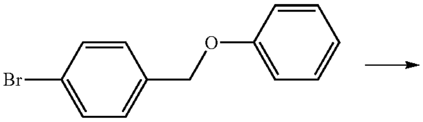

29a

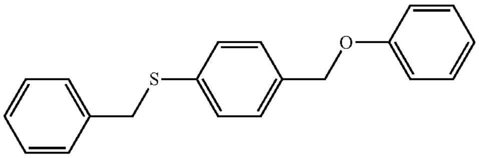

29b

To a solution of 1-bromo-4-(phenoxymethyl)benzene (29a) (520 mg, 1.9 mmol) in 1,4-dioxane (5 mL) were added phenylmethanethiol (472 mg, 3.8 mmol), $Pd_2(dba)_3$ (173 mg, 0.19 mmol), Xantphos (220 mg, 0.38 mmol), and DIEA (0.6 mL, 3.8 mmol). The mixture was stirred at 110° C. under $N_2$ for 16 h. The mixture was cooled down to 23° C. and concentrated. The crude product was purified by silica gel column chromatography (10% EtOAc in PE) to afford benzyl(4-(phenoxymethyl)phenyl)sulfane (29b) (170 mg, 29% yield) as a colorless oil. $^1$H NMR (400 MHz, DMSO-$d_6$) δ 7.39-7.14 (m, 12H), 7.03-6.89 (m, 3H), 5.04 (s, 2H), 4.24 (s, 2H).

Step 3. Synthesis of 4-(phenoxymethyl)benzenesulfonyl chloride (29c)

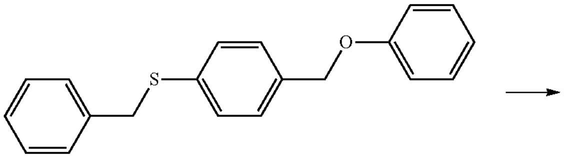

29b

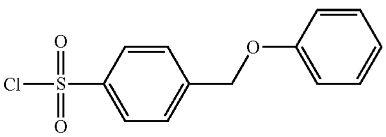

29c

To a solution of benzyl(4-(phenoxymethyl)phenyl)sulfane (29b) (170 mg, 0.56 mmol) in AcOH/$H_2O$ (4 mL/2 mL) was added N-chlorosuccinimide (NCS) (224 mg, 1.68 mmol) at 0° C. The mixture was stirred at 23° C. for 2 h. Water (20 mL) was added and extracted with EtOAc (10 mL×3). The combined organic layers were washed with brine (30 mL), dried over $Na_2SO_4$, concentrated and purified by silica gel column chromatography (5% EtOAc in PE) to afford 4-(phenoxymethyl)benzenesulfonyl chloride (29c) (100 mg, 63% yield) as a colorless oil. $^1$H NMR (400 MHz, Chloroform-d) δ 7.49 (d, J=8.0 Hz, 2H), 7.43-7.37 (m, 2H), 7.30 (t, J=7.8 Hz, 3H), 6.98 (h, J=8.1 Hz, 4H), 5.20-5.07 (m, 2H).

Step 4. Synthesis of 1,1-dioxido-2,3-dihydrothiophen-3-yl 4-(phenoxymethyl)benzenesulfonate (29)

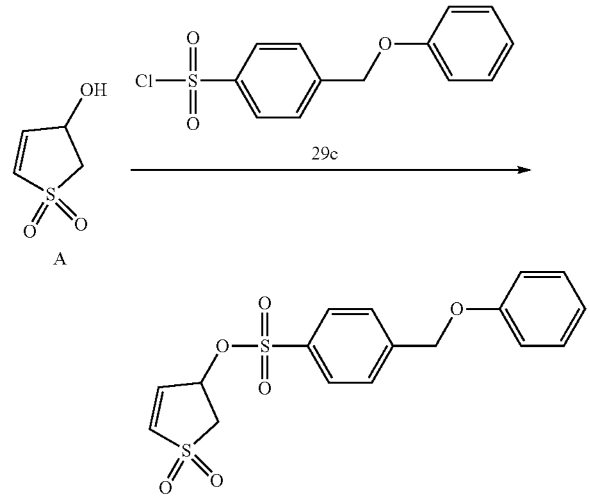

29

To a solution of compound (A) (50 mg, 0.36 mmol) in DCM (5 mL) was added DIPEA (93 mg, 0.72 mmol), DMAP (4 mg, 0.036 mmol) and 4-(phenoxymethyl)benzenesulfonyl chloride (29c) (100 mg, 0.35 mmol) at 0° C. The mixture was stirred at 23° C. for 2 h and diluted with DCM (30 mL), washed with brine (30 mL), dried over $Na_2SO_4$, concentrated and purified by silica gel column chromatography (10% to 20% EtOAc in PE) to afford 1,1-dioxido-2,3-dihydrothiophen-3-yl 4-(phenoxymethyl)benzenesulfonate (29) (21 mg, 16% yield) as a white solid. LCMS: m/z: 398.00 [M+18]+. HPLC: 6.245 min, m/z, 97.5% at 214 nm. $^1$H NMR (400 MHz, chloroform-d) δ 7.96-7.94 (m, 2H), 7.69 (d, J=8.2 Hz, 2H), 7.34-7.30 (m, 2H), 7.03-6.96 (m, 3H), 6.85-6.83 (m, 1H), 6.66 (dd, J=6.7, 2.8 Hz, 1H), 5.74-5.72 (m, 1H), 5.19 (s, 2H), 3.58 (dd, J=14.2, 7.7 Hz, 1H), 3.28 (dd, J=14.2, 3.9 Hz, 1H).

Example 30

Synthesis of methyl naphthalene-2-sulfonate (30)

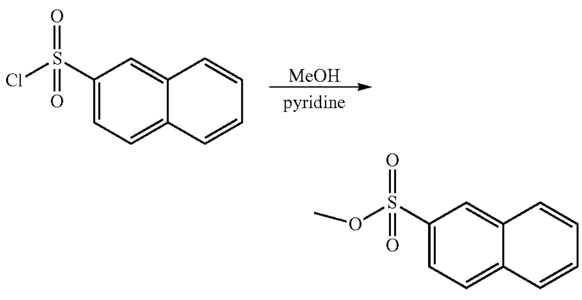

30

To a solution of naphthalene-2-sulfonyl chloride (1 g, 4.41 mmol) in dry pyridine (5 mL) was added MeOH (1 mL) at 23° C. The mixture was stirred at 23° C. for 2 h, diluted with water (30 mL), and extracted with DCM (20 mL). The organic layer was washed with brine (30 mL), dried over $Na_2SO_4$, concentrated, and purified by silica gel column chromatography (5% EtOAc in PE) to afford methyl naphthalene-2-sulfonate (30) (500 mg, 51% yield) as a white solid. $^1$H NMR (400 MHz, chloroform-d) δ 8.52-8.48 (m, 1H), 8.01 (dd, J=8.5, 5.0 Hz, 2H), 7.95 (d, J=8.0 Hz, 1H), 7.87 (dd, J=8.7, 1.9 Hz, 1H), 7.67 (dddd, J=18.6, 8.1, 6.9, 1.3 Hz, 2H), 3.79 (d, J=0.7 Hz, 3H). HPLC: 3.879 min, m/z, 95.86% at 254 nm, 99.06% at 214 nm.

Example 31

Synthesis of ethyl naphthalene-2-sulfonate (31)

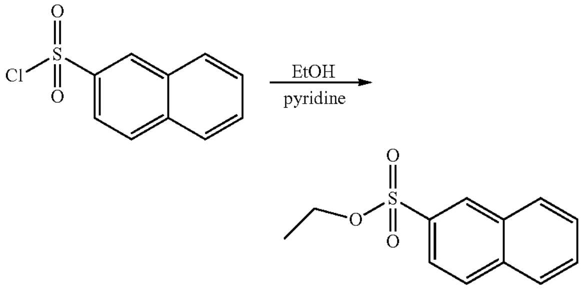

31

To a solution of naphthalene-2-sulfonyl chloride (1 g, 4.41 mmol) in dry pyridine (5 mL) was added EtOH (1 mL) at 23° C. The mixture was stirred at 23° C. for 2 h and diluted with water (30 mL), extracted with DCM (20 mL). The organic layer was washed with brine (30 mL), dried over $Na_2SO_4$, concentrated, and purified by silica gel column chromatography (5% EtOAc in PE) to afford ethyl naphthalene-2-sulfonate (31) (800 mg, 77% yield) as a white solid. LCMS: m/z: 237.00 $[M+H]^+$. HPLC: 4.969 min, m/z, 98.07% at 254 nm, 99.33% at 214 nm. $^1$H NMR (400 MHz, chloroform-d) δ 8.51-8.48 (m, 1H), 8.00 (dd, J=8.4, 4.0 Hz, 2H), 7.94 (d, J=8.0 Hz, 1H), 7.87 (dd, J=8.7, 1.8 Hz, 1H), 7.71-7.62 (m, 2H), 4.17 (q, J=7.1 Hz, 2H), 1.31 (t, J=7.1 Hz, 3H).

Example 32

Synthesis of isopropyl naphthalene-2-sulfonate (32)

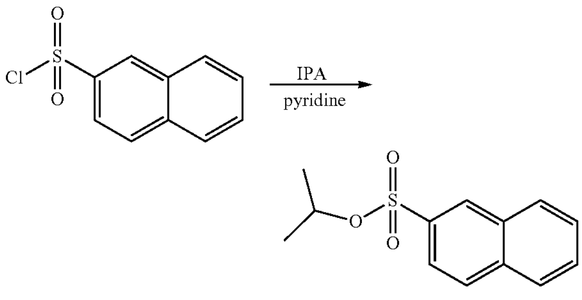

32

To a solution of naphthalene-2-sulfonyl chloride (1 g, 4.41 mmol) in dry pyridine (5 mL) was added IPA (1 ml) at 23° C. The mixture was stirred at 23° C. for 2 h and diluted with water (30 mL), extracted with DCM (20 mL). The organic layer was washed with brine (30 mL), dried over $Na_2SO_4$, concentrated and purified by silica gel column chromatography (5% EtOAc in PE) to afford isopropyl naphthalene-2-sulfonate (32) (640 mg, 58% yield) as a white solid. LCMS: m/z: 267.95 $[M+18]^+$. HPLC: 4.787 min, m/z, 99.48% at 254 nm, 99.82% at 214 nm. $^1H$ NMR (400 MHz, chloroform-d) δ 8.50 (d, J=1.8 Hz, 1H), 7.99 (d, J=8.3 Hz, 2H), 7.93 (d, J=8.0 Hz, 1H), 7.87 (dd, J=8.6, 1.8 Hz, 1H), 7.66 (dtd, J=13.3, 7.0, 3.5 Hz, 2H), 4.81 (p, J=6.3 Hz, 1H), 1.29 (d, J=6.2 Hz, 6H).

Example 33

Synthesis of 1,1-dioxido-2,3-dihydrothiophen-3-yl [1,1'-biphenyl]-4-sulfonate (33)

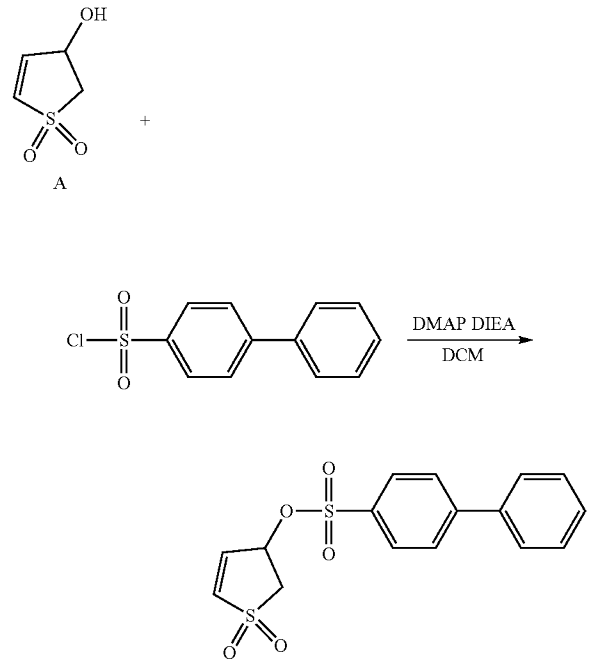

A

+

33

To a solution of compound (A) (250 mg, 1.86 mmol) in DCM (5 mL) was added DMAP (45 mg, 0.368 mmol), DIPEA (480 mg, 3.72 mmol), and 4-cyclohexylbenzenesulfonyl chloride (470 mg, 1.86 mmol) at 23° C. The reaction mixture was stirred at 23° C. for 1.0 h and diluted with water (30 mL) and extracted with DCM (20 mL). The organic layer was washed with brine (50 mL), dried over $Na_2SO_4$, and concentrated in vacuo. The crude product was purified by Prep-TLC (PE:EtOAc=2:1) to afford 1,1-dioxido-2,3-dihydrothiophen-3-yl [1,1'-biphenyl]-4-sulfonate (33) (110 mg, 16.9% yield) as a white solid. $^1H$ NMR (400 MHz, DMSO-$d_6$) δ 8.07-7.99 (m, 4H), 7.79 (d, J=7.3 Hz, 2H), 7.57-7.46 (m, 4H), 6.89 (dd, J=6.7, 3.4 Hz, 1H), 5.92 (dt, J=6.6, 2.7 Hz, 1H), 3.73 (dd, J=14.8, 7.5 Hz, 1H), 3.38 (dd, J=14.8, 2.2 Hz, 1H). LCMS: m/z: 368.0 $[M+18]^+$. HPLC: 11.350 min, m/z, 97.01% at 254 nm, 98.90% at 214 nm.

Example 34

Synthesis of 1,1-dioxido-2,3-dihydrothiophen-3-yl 4-cyclohexylbenzenesulfonate (34)

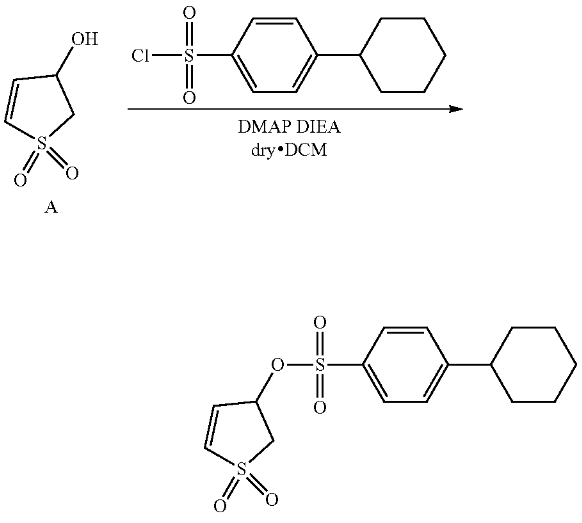

A

34

To a solution of compound (A) (Example A) (300 mg, 2.24 mmol) in dry DCM (5 mL) was added DIEA (578 mg, 4.47 mmol), DMAP (54.6 mg, 0.45 mmol) and 4-cyclohexylbenzenesulfonyl chloride (578 mg, 2.24 mmol) at 23° C. The mixture was stirred at 23° C. for 2 h, diluted with water (30 mL), and extracted with DCM (20 mL). The organic layer was washed with brine (30 mL), dried over $Na_2SO_4$, concentrated under vacuum, and purified by RP-column chromatography (0.1% HCOOH/$H_2O$ and acetonitrile) to afford 200 mg of the crude product, which was washed by water/MeOH=10/1 to afford 1,1-dioxido-2,3-dihydrothiophen-3-yl 4-cyclohexylbenzenesulfonate (34) (117 mg, 14.68% yield) as a white solid. $^1H$ NMR (400 MHz, DMSO-$d_6$) δ 7.89 (d, J=8.4 Hz, 2H), 7.56 (d, J=8.4 Hz, 2H), 7.48 (dd, J=6.7, 1.1 Hz, 1H), 6.85 (dd, J=6.7, 3.4 Hz, 1H), 5.95-5.80 (m, 1H), 3.69 (dd, J=14.7, 7.5 Hz, 1H), 3.35 (d, J=2.2 Hz, 1H), 2.67 (t, J=11.0 Hz, 1H), 1.81 (d, J=10.3 Hz, 4H), 1.72 (d, J=12.9 Hz, 1H), 1.50-1.33 (m, 4H), 1.30-1.19 (m, 1H). LCMS: m/z: 374.1 $[M+18]^+$; HPLC: 15.756 min, m/z, 97.09% at 254 nm, 97.20% at 214 nm.

Example 35

Synthesis of 1,1-dioxido-2,3-dihydrothiophen-3-yl 3-cyclohexylbenzenesulfonate (35)

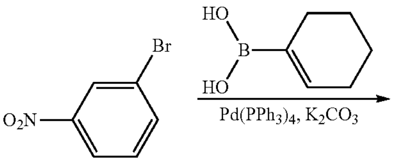

-continued

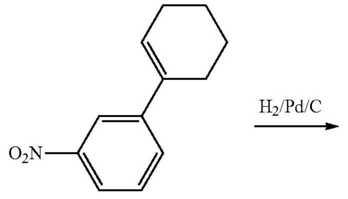

35a

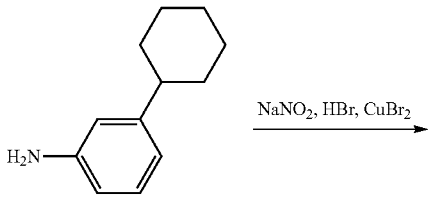

35b

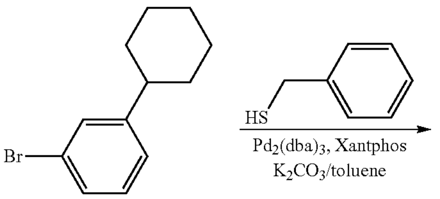

35c

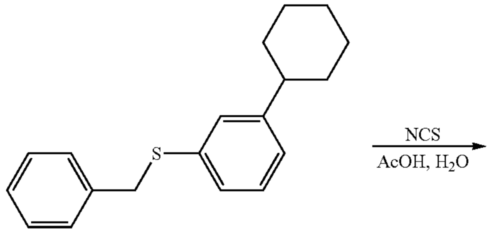

35d

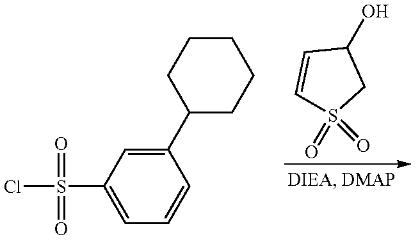

35e

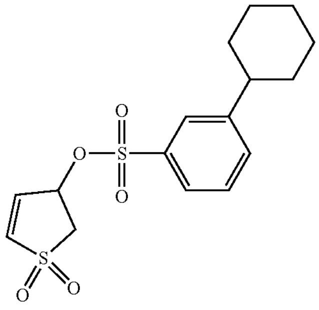

35

Step 1. Synthesis of 3'-nitro-2,3,4,5-tetrahydro-1,1'-biphenyl (35a)

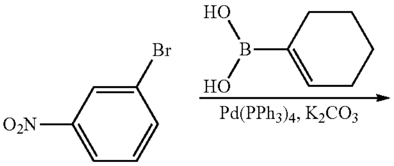

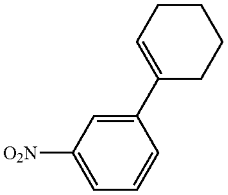

35a

To a solution of 1-bromo-3-nitrobenzene (7.0 g, 34.65 mmol) and cyclohex-1-en-1-ylboronic acid (35a) (5.25 g, 41.58 mmol) in 1,4-dioxane (50 mL)/$H_2O$ (10 mL) was added Pd(PPh$_3$)$_4$ (2.0 g, 1.73 mmol) and $K_2CO_3$ (9.45 g, 69.30 mmol). The mixture was stirred at 110° C. under nitrogen for 16 h. The mixture was concentrated and diluted with DCM (200 mL), washed with brine (300 mL), dried over $Na_2SO_4$, concentrated, and purified by silica gel column chromatography (5% EtOAc in PE) to afford 3'-nitro-2,3,4,5-tetrahydro-1,1'-biphenyl (35a) (6 g, 86% yield) as a colorless oil. $^1$H NMR (400 MHz, chloroform-d) δ 8.22 (t, J=2.1 Hz, 1H), 8.05 (dd, J=8.2, 2.2 Hz, 1H), 7.69 (dt, J=7.9, 1.3 Hz, 1H), 7.45 (t, J=8.0 Hz, 1H), 6.31-6.19 (m, 1H), 2.43 (ddt, J=6.2, 4.1, 2.2 Hz, 2H), 2.25 (dq, J=6.1, 3.3 Hz, 2H), 1.86-1.77 (m, 2H), 1.73-1.63 (m, 2H).

Step 2. Synthesis of 3-cyclohexylaniline (35b)

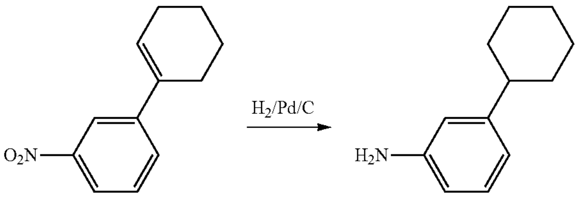

35a 35b

A solution of 3'-nitro-2,3,4,5-tetrahydro-1,1'-biphenyl (35a) (6 g, 29.52 mmol) in MeOH (50 mL) was added Pd/C (600 mg), the mixture was stirred under 1 atm $H_2$ at room temperature for 16 h. The mixture was filtered and concentrated to afford 3-cyclohexylaniline (35b) (5.2 g, 100% yield) as a colorless oil. $^1$H NMR (400 MHz, chloroform-d) δ 7.08 (t, J=7.7 Hz, 1H), 6.63 (d, J=7.6 Hz, 1H), 6.58-6.49 (m, 2H), 2.46-2.35 (m, 1H), 1.92-1.69 (m, 6H), 1.46-1.14 (m, 6H).

Step 3. Synthesis of 1-bromo-3-cyclohexylbenzene (35c)

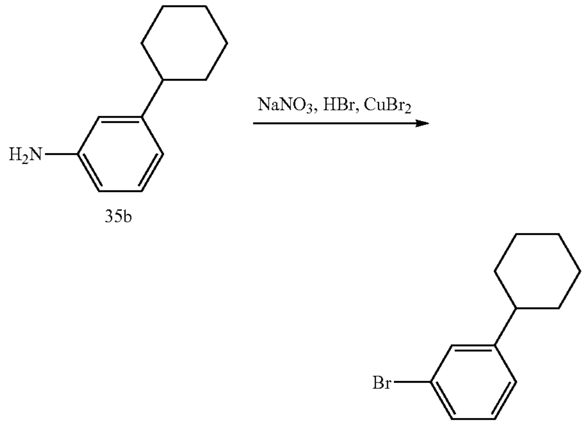

35b

35c

To a solution of 3-cyclohexylaniline (35b) (2.0 g, 11.42 mmol) in HBr.aq (10 mL) was added $NaNO_2$ (1.0 g, 14.85 mmol) and $CuBr_2$ (2.3 g, 14.85 mmol) at 0° C. The mixture was stirred at 23° C. for 2 h and diluted with DCM (30 mL), washed with brine (30 mL), dried over $Na_2SO_4$, concentrated, and purified by silica gel column chromatography (5% EtOAc in PE) to afford 1-bromo-3-cyclohexylbenzene (35c) (900 mg, 33% yield) as a colorless oil.

Step 4. Synthesis of benzyl(3-cyclohexylphenyl)sulfane (35d)

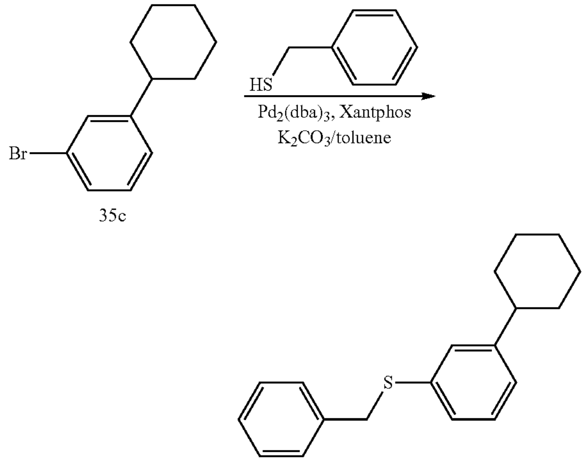

35c

35d

To a solution of 1-bromo-3-cyclohexylbenzene (35c) (2.7 g, 11.34 mmol) in toluene (50 mL) was added phenylmethanethiol (2.8 g, 22.69 mmol), $Pd_2(dba)_3$ (945 mg, 1.13 mmol), Xantphos (1.21 g, 2.27 mmol), and $K_2CO_3$ (3.09 g, 22.69 mmol). The mixture was stirred at 110° C. under $N_2$ for 16 h. The mixture was cooled to 23° C. and diluted with DCM (100 mL), washed with brine (200 mL), dried over $Na_2SO_4$, concentrated, and purified by silica gel column chromatography (10% EtOAc in PE) to afford benzyl(3-cyclohexylphenyl)sulfane (35d) (2.2 g, 68% yield) as a colorless oil.

Step 5. Synthesis of 3-cyclohexylbenzenesulfonyl chloride (35e)

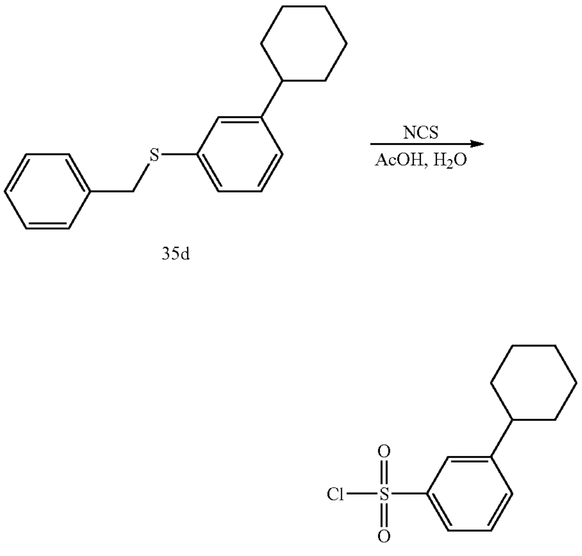

35d

35e

To a solution of benzyl(3-cyclohexylphenyl)sulfane (35d) (2.0 g, 7.09 mmol) in AcOH (30 mL)/$H_2O$ (15 mL) was added NCS (3.3 g, 21.27 mmol) at 0° C. The mixture was stirred at 23° C. for 16 h. The mixture was concentrated and diluted with DCM (100 mL), washed with brine (200 mL), dried over $Na_2SO_4$, concentrated, and purified by silica gel column chromatography (10% EtOAc in PE) to afford 3-cyclohexylbenzenesulfonyl chloride (35e) (800 mg, 43% yield) as a yellow oil. $^1H$ NMR (400 MHz, DMSO-d6) δ 7.47 (d, J=1.8 Hz, 1H), 7.43-7.40 (m, 1H), 7.24 (t, J=7.5 Hz, 1H), 7.19-7.16 (m, 1H), 2.50 (s, 1H), 1.80 (dp, J=8.7, 2.9, 2.5 Hz, 6H), 1.39 (ddt, J=10.2, 7.8, 2.2 Hz, 4H).

Step 6. Synthesis of 1,1-dioxido-2,3-dihydrothiophen-3-yl 3-cyclohexylbenzenesulfonate (35)

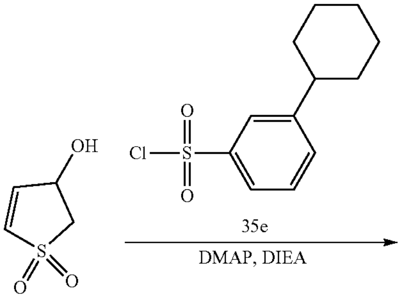

A

35e

-continued

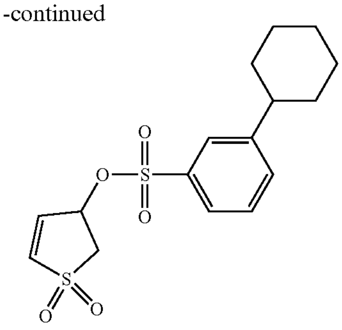

35

To a solution of compound (A) in DCM (15 mL) was added DIPEA (800 mg, 6.18 mmol), DMAP (38 mg, 0.31 mmol) and 3-cyclohexylbenzenesulfonyl chloride (35e) (800 mg, 3.09 mmol) at 0° C. The mixture was stirred at 23° C. for 2 h and diluted with DCM (100 mL), washed with brine (200 mL), dried over $Na_2SO_4$, concentrated, and purified by silica gel column chromatography (10% to 20% EtOAc in PE) to afford 1,1-dioxido-2,3-dihydrothiophen-3-yl 3-cyclohexylbenzenesulfonate (35) (125.7 mg, 12% yield) as a white solid. $^1H$ NMR (400 MHz, chloroform-d) δ 7.74 (dd, J=9.0, 1.8 Hz, 2H), 7.59-7.54 (m, 1H), 7.51 (t, J=7.6 Hz, 1H), 6.83 (dd, J=6.8, 1.5 Hz, 1H), 6.65 (dd, J=6.8, 2.8 Hz, 1H), 5.75-5.66 (m, 1H), 3.55 (dd, J=14.2, 7.7 Hz, 1H), 3.25 (dd, J=14.3, 3.9 Hz, 1H), 2.62 (s, 1H), 1.94-1.74 (m, 5H), 1.50-1.27 (m, 5H). LCMS: m/z: 374.00 $[M+18]^+$; HPLC: 6.245 min, m/z, 96.43% at 214 nm.

Example 36

Synthesis of 1,1-dioxido-2,3-dihydrothiophen-3-yl 4-(cyclohexyloxy)benzenesulfonate (36)

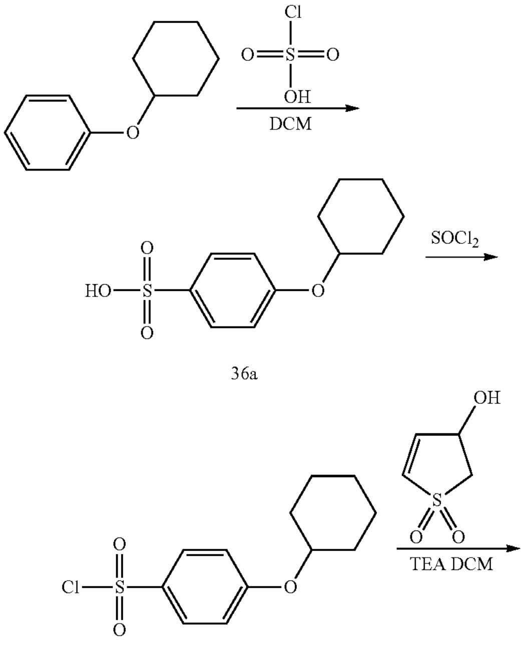

36a

36b

-continued

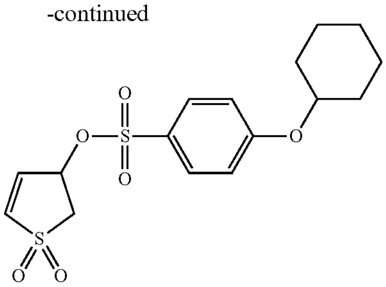

36

Step 1. Synthesis of 4-(cyclohexyloxy)benzenesulfonic acid (36a)

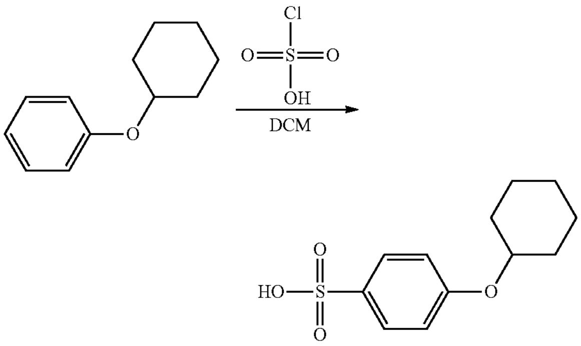

36a

To a solution of (cyclohexyloxy)benzene (2.0 g, 11.35 mmol) in DCM (20 mL) was added $HSO_3Cl$ (1.30 g, 11.35 mmol). The reaction was stirred at room temperature for 3 h. The mixture was concentrated to afford 4-(cyclohexyloxy) benzenesulfonic acid (36a) (1.3 g) as a yellow oil.

Step 2. Synthesis of 4-(cyclohexyloxy)benzenesulfonyl chloride (36b)

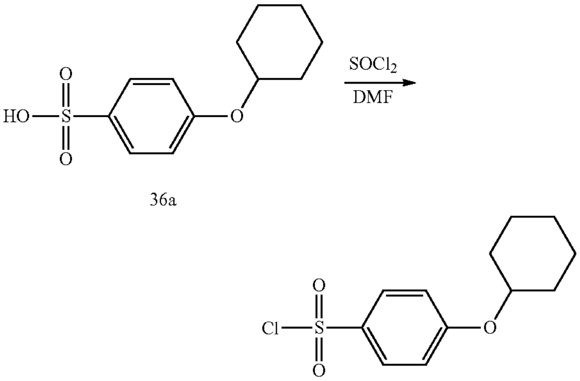

36a

36b

To a solution of 4-(cyclohexyloxy)benzenesulfonic acid (36a) (1.3 g, 5.08 mmol) in DMF (15 mL) was added thionyl chloride (0.9 g, 7.62 mmol) at 0° C., and the mixture was stirred at 23° C. for 2 h. The mixture was diluted with water (150 mL) and extracted with EtOAc (50 mL×2). The combined organic layers were washed with brine, dried over $Na_2SO_4$ and concentrated. The residue was purified by silica gel column chromatography (10% EtOAc in PE) to afford 4-(cyclohexyloxy)benzenesulfonyl chloride (36b) (340 mg, 24.5% yield) as a white solid. $^1H$ NMR (400 MHz, chloroform-d) δ 7.94 (d, J=8.8 Hz, 2H), 7.01 (d, J=8.8 Hz, 2H), 4.40 (dt, J=8.8, 4.8 Hz, 1H), 2.03-1.95 (m, 3H), 1.83 (ddd, J=17.8, 7.4, 3.8 Hz, 3H), 1.45-1.35 (m, 4H).

Step 3. Synthesis of 1,1-dioxido-2,3-dihydrothiophen-3-yl 4-(cyclohexyloxy)benzenesulfonate (36)

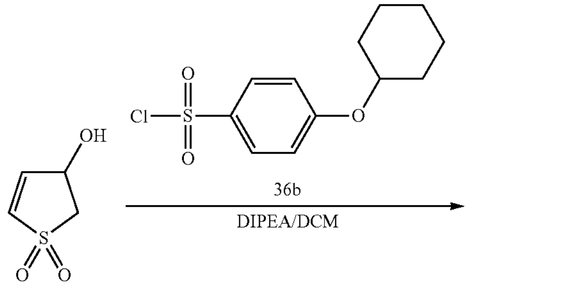

A

36b

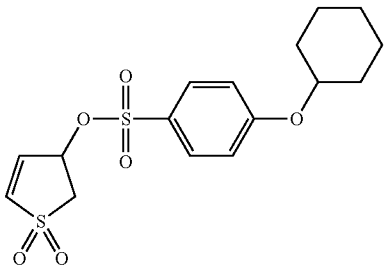
36

To a solution of compound (A) (151 mg, 1.13 mmol) in DCM (5 mL) was added DMAP (13.8 mg, 0.11 mmol), DIPEA (218 mg, 1.69 mmol) and 4-(cyclohexyloxy)benzenesulfonyl chloride (36b) (340 mg, 1.24 mmol) at 0° C. The mixture was stirred at 23° C. for 1 h, diluted with water (30 mL), and extracted with DCM (30 mL×2). The combined organic layers were washed with brine, dried over $Na_2SO_4$, filtered, and concentrated. The residue was purified by silica gel column chromatography on silica gel (10% to 20% EtOAc in PE) to afford 1,1-dioxido-2,3-dihydrothiophen-3-yl 4-(cyclohexyloxy)benzenesulfonate (36) (121.8 mg, 26.4% yield) as a white solid. LCMS: m/z: 390.1 $[M+18]^+$; HPLC: 5.518 min, m/z, 99.77% at 214 nm, 99.73% at 254 nm; $^1H$ NMR (400 MHz, chloroform-d) δ 7.86-7.78 (m, 2H), 7.05-6.98 (m, 2H), 6.82 (dd, J=6.8, 1.6 Hz, 1H), 6.67 (d, J=2.8 Hz, 1H), 5.66 (dt, J=6.2, 2.4 Hz, 1H), 4.38 (tt, J=8.6, 3.8 Hz, 1H), 3.56 (dd, J=14.2, 7.6 Hz, 1H), 3.25 (dd, J=14.2, 4.0 Hz, 1H), 1.99 (dt, J=8.2, 4.4 Hz, 2H), 1.82 (dd, J=11.4, 5.0 Hz, 2H), 1.58 (q, J=9.2 Hz, 4H), 1.44-1.37 (m, 2H).

Example 37

Synthesis of 1,1-dioxido-2,3-dihydrothiophen-3-yl 3-(cyclohexyloxy)benzenesulfonate (37)

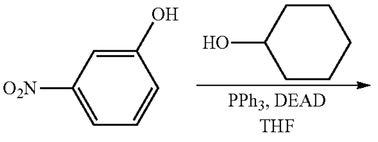

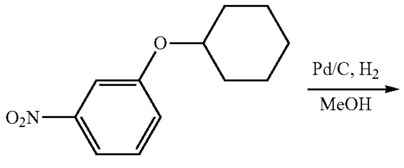

37a

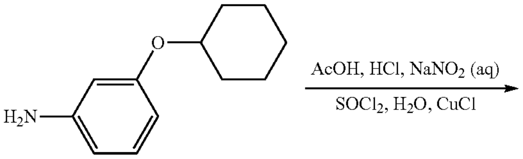

37b

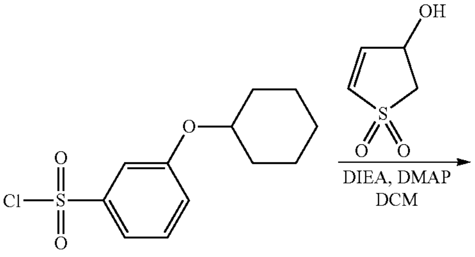

37c

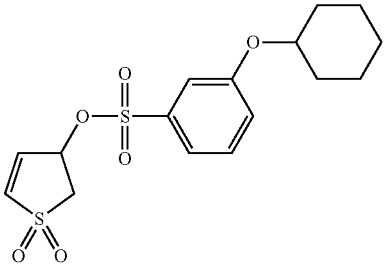
37

Step 1. Synthesis of afford 1-(cyclohexyloxy)-3-nitrobenzene (37a)

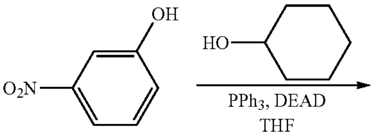

-continued

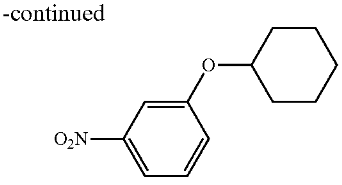

37a

To a solution of 3-nitrophenol (5.0 g, 35.9 mmol) in THF (70 mL) was added cyclohexanol (7.2 g, 71.8 mmol), triphenylphosphine (11.3 g, 43.1 mmol) and DIAD (8.7 g, 43.1 mmol) at 0° C., the resulting mixture was stirred at 23° C. for 16 h. The reaction mixture was concentrated in vacuo and purified by silica gel column chromatography (PE/EtOAc=100/1, v/v) to afford 1-(cyclohexyloxy)-3-nitrobenzene (37a) (2.5 g, 31.5% yield) as a colorless oil. $^1$H NMR (400 MHz, DMSO-$d_6$) δ 7.77 (ddd, J=8.2, 2.2, 0.9 Hz, 1H), 7.67 (t, J=2.4 Hz, 1H), 7.55 (t, J=8.2 Hz, 1H), 7.42 (ddd, J=8.3, 2.5, 0.9 Hz, 1H), 4.52 (tt, J=8.5, 3.7 Hz, 1H), 1.93 (d, J=12.0 Hz, 2H), 1.71 (dd, J=9.2, 4.1 Hz, 2H), 1.58-1.26 (m, 7H).

Step 2. Synthesis of 3-(cyclohexyloxy)aniline (37b)

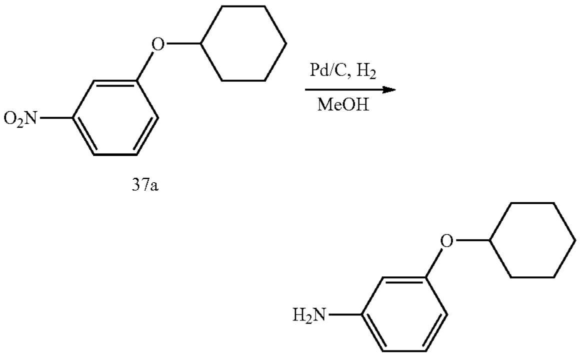

37a

37b

To a solution of 1-(cyclohexyloxy)-3-nitrobenzene (37a) (2.5 g, 11.3 mmol) in MeOH (20 mL) was added Pd/C (250 mg). The mixture was stirred at 23° C. under an $H_2$ atmosphere (1 atm) for 16 h. The reaction mixture was filtered and concentrated in vacuo to afford 3-(cyclohexyloxy)aniline (37b) (2.0 g, 92.9% yield) as a yellow oil. $^1$H NMR (400 MHz, DMSO-$d_6$) δ 6.86 (t, J=7.9 Hz, 1H), 6.16-6.08 (m, 2H), 6.06 (ddd, J=8.2, 2.4, 1.0 Hz, 1H), 4.95 (s, 2H), 4.15 (tt, J=8.5, 3.6 Hz, 1H), 1.94-1.84 (m, 2H), 1.74-1.63 (m, 2H), 1.52 (ddd, J=11.8, 6.0, 3.7 Hz, 1H), 1.44-1.21 (m, 5H).

Step 3. Synthesis of 3-(cyclohexyloxy)benzenesulfonyl chloride (37c)

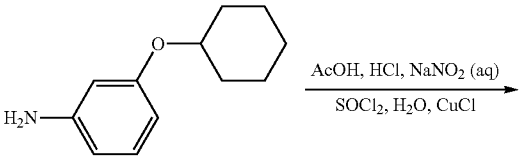

37b

-continued

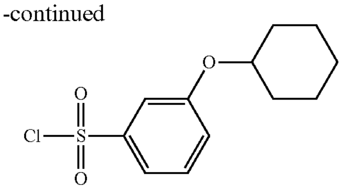

37c

To a three-necked bottle was added 3-(cyclohexyloxy)aniline (37b) (2.0 g, 10.5 mmol), AcOH (12 mL), concentrated HCl (3.5 mL, 42.0 mmol) and aqueous $NaNO_2$ (800 mg, 11.6 mmol) at 0° C. The mixture was stirred at 23° C. for 30 min. Meantime, to a solution of copper(I) chloride (416 mg, 4.2 mmol) in water (40 mL) was added thionyl chloride (6.2 g, 52.5 mmol) at 0° C. After stirring at 23° C. for 30 min, the diazonium salt mixture was added at 0° C. and stirred at 23° C. for 20 min. The reaction mixture was diluted with water (50 mL) and extracted with EtOAc (40 mL). The organic phase was washed by brine, dried over $Na_2SO_4$ and concentrated in vacuo to afford the crude product which was purified by silica gel column chromatography (PE/EtOAc=50/1, v/v) to afford 3-(cyclohexyloxy)benzenesulfonyl chloride (37c) (1.2 g, 41.6% yield) as a yellow oil. $^1$H NMR (400 MHz, DMSO-$d_6$) δ 7.21 (t, J=7.8 Hz, 1H), 7.17-7.09 (m, 2H), 6.86 (ddd, J=8.0, 2.7, 1.2 Hz, 1H), 4.29 (tt, J=8.4, 3.7 Hz, 1H), 1.90 (dq, J=9.9, 3.5 Hz, 2H), 1.75-1.65 (m, 2H), 1.57-1.29 (m, 6H).

Step 4. Synthesis of 1,1-dioxido-2,3-dihydrothiophen-3-yl 3-(cyclohexyloxy)benzenesulfonate (37)

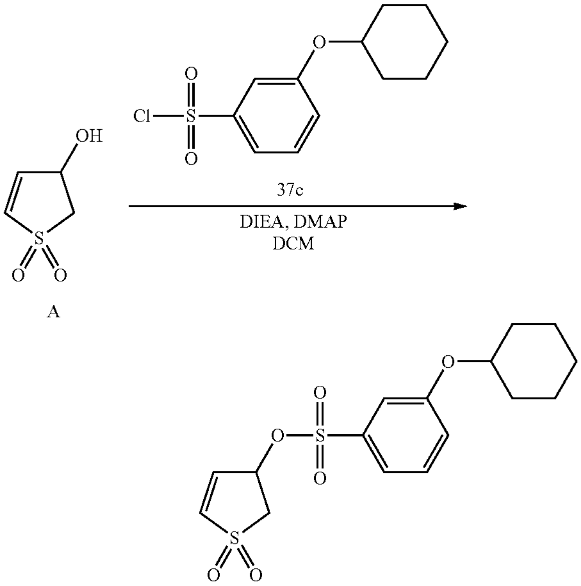

A

37

To a solution of compound (A) (Example A) (332 mg, 2.48 mmol) in DCM (5 mL) was added DIPEA (481 mg, 3.72 mmol), DMAP (31 mg, 0.25 mmol) and 3-(cyclohexyloxy)benzenesulfonyl chloride (37c) (750 mg, 2.73 mmol). The mixture was stirred at 23° C. for 15 min. The reaction mixture was diluted with water (20 mL) and extracted by DCM (10 mL×2). The combined organic phase was washed by brine (30 mL), dried over $Na_2SO_4$, and concentrated in vacuo to give the crude product which was purified by silica gel column chromatography (PE/EtOAc=10/1 to 2/1, v/v) to afford 1,1-dioxido-2,3-dihydrothiophen-3-yl 3-(cyclohexyloxy)benzenesulfonate (37) (234.5 mg, 25.4% yield) as a white solid. $^1H$ NMR (400 MHz, chloroform-d) δ 7.51-7.42 (m, 2H), 7.39 (t, J=2.0 Hz, 1H), 7.21 (ddd, J=7.8, 2.5, 1.6 Hz, 1H), 6.84 (dd, J=6.8, 1.6 Hz, 1H), 6.66 (dd, J=6.8, 2.8 Hz, 1H), 5.70 (dddd, J=8.2, 4.2, 2.8, 1.6 Hz, 1H), 4.34 (tt, J=8.5, 3.7 Hz, 1H), 3.57 (dd, J=14.2, 7.6 Hz, 1H), 3.27 (dd, J=14.2, 3.9 Hz, 1H), 2.03-1.93 (m, 2H), 1.87-1.78 (m, 2H), 1.60 (dd, J=10.2, 3.6 Hz, 2H), 1.56-1.51 (m, 1H), 1.46-1.32 (m, 3H). LCMS: m/z: 390.1 $[M+18]^+$; HPLC: 5.872 min, m/z, 99.9% at 214 nm.

Example 38

Synthesis of 1,1-dioxido-2,3-dihydrothiophen-3-yl 4-benzoylbenzenesulfonate (38)

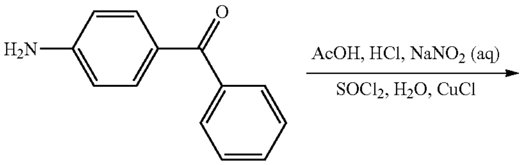

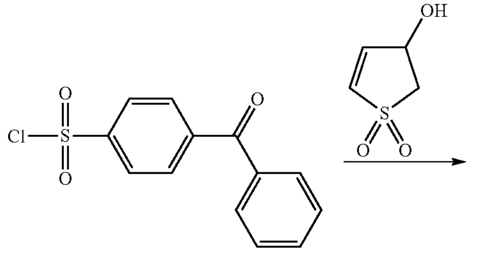

38a
2

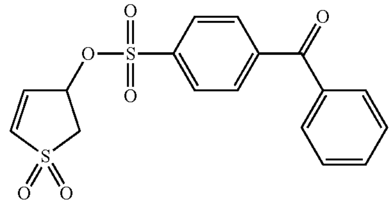

38

Step 1. Synthesis of 4-benzoylbenzenesulfonyl chloride (38a)

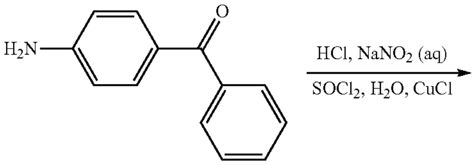

-continued

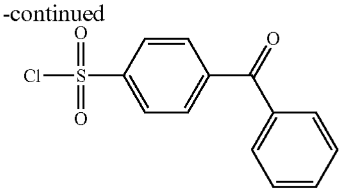

38a

To a solution of (4-aminophenyl)(phenyl)methanone (5.0 g, 25.35 mmol) in con. HCl (10 mL) and $H_2O$ (10 mL) was added a solution of $NaNO_2$ (2.37 g, 27.89 mmol) in $H_2O$ (6 mL) at 0° C. The reaction mixture was stirred at 0° C. for 30 min to obtain the diazonium salt solution. To a solution of CuCl (25 mg, 0.25 mmol) in $H_2O$ (50 mL) was added $SOCl_2$ (13.57 g, 114.08 mmol) at 0° C., stirred at 0° C. for 30 min, the above diazonium salt solution was added. The mixture was stirred at 23° C. for 20 min and extracted with DCM (50 mL×2). The combined organic layer was washed with brine (50 mL), dried over $Na_2SO_4$ and concentrated. The residue was purified by silica gel column chromatography (eluent: PE:EtOAc=5:1) to afford 4-benzoylbenzenesulfonyl chloride (38a) (2.1 g, 30% yield) as a yellow solid. TLC: Rf=0.6 (silica gel, PE:EtOAc=5:1, v/v).

Step 2. Synthesis of 1,1-dioxido-2,3-dihydrothiophen-3-yl 4-benzoylbenzenesulfonate (38)

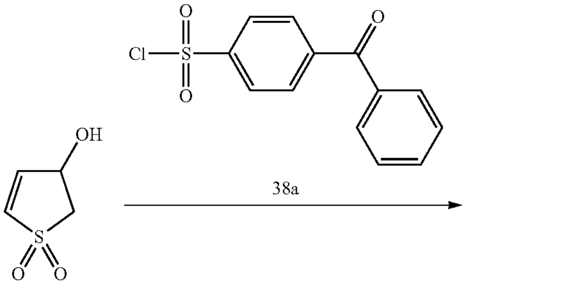

A

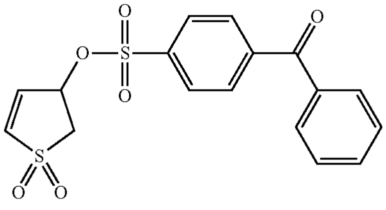

38

To a solution of compound (A) (477.8 mg, 3.56 mmol) in DCM (10 mL) was added 4-benzoylbenzenesulfonyl chloride (38a) (1.0 g, 3.56 mmol), DIEA (0.93 mL, 5.34 mmol) and DMAP (43.5 mg, 0.356 mmol) at 0° C. The reaction mixture was stirred at 0° C. for 30 min. The mixture was diluted with water (20 mL) and extracted with DCM (20 mL×2). The combined organic layer was washed with brine, dried over $Na_2SO_4$, filtered, and concentrated. The residue was purified by silica gel column chromatography (PE: EtOAc=10/1 to 5/1, v/v) to afford 1,1-dioxido-2,3-dihydrothiophen-3-yl 4-benzoylbenzenesulfonate (38) (300 mg, 22% yield) as a white solid. LCMS: m/z=378.95 $[M+H]^+$;

$^1$H NMR (400 MHz, Chloroform-d) δ 8.06 (d, J=8.4 Hz, 2H), 7.98 (d, J=8.4 Hz, 2H), 7.85-7.76 (m, 2H), 7.70-7.64 (m, 1H), 7.54 (t, J=7.6 Hz, 2H), 6.89 (dd, J=6.8, 1.4 Hz, 1H), 6.70 (dd, J=6.8, 2.8 Hz, 1H), 5.81 (dt, J=6.5, 2.4 Hz, 1H), 3.66 (dd, J=14.3, 7.6 Hz, 1H), 3.36 (dd, J=14.3, 3.7 Hz, 1H). TLC: Rf=0.4 (silica gel, PE:EtOAc=2:1, v/v).

Example 39

Synthesis of 1,1-dioxido-2,3-dihydrothiophen-3-yl 4-(hydroxy(phenyl)methyl)benzenesulfonate (39)

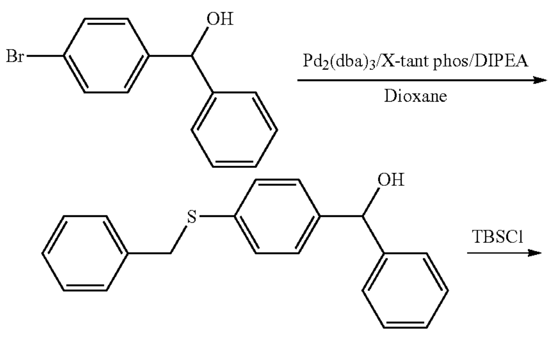

39a

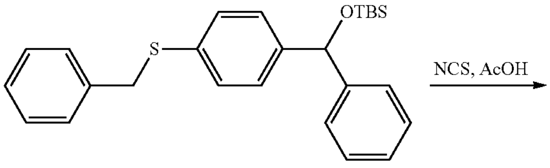

39b

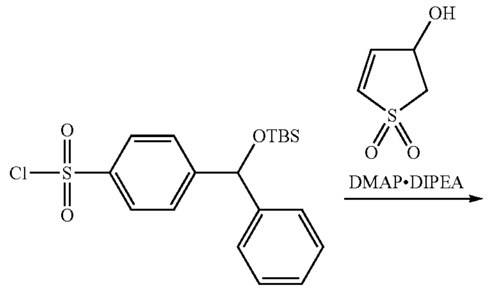

39c

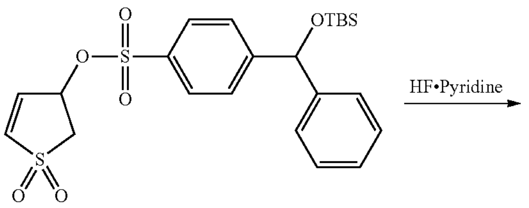

39d

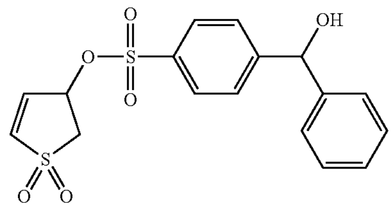

39

Step 1. Synthesis of 4-(benzylthio)phenyl)(phenyl)methanol (39a)

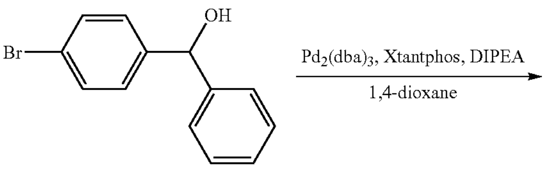

39a

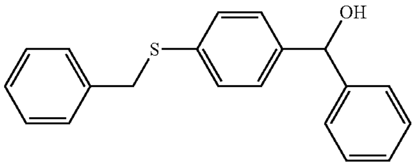

39b

To a solution of (4-bromophenyl)(phenyl)methanol (2.0 g, 7.60 mmol) in 1,4-dioxane (20 mL) was added phenylmethanethiol (1.89 g, 15.20 mmol), $Pd_2(dba)_3$ (695 mg, 760 mol), Xtantphos (876 mg, 1.52 mmol) and DIPEA (1.96 g, 15.2 mmol). The reaction mixture was stirred at 110° C. for 16 h. The mixture was filtered and concentrated. The residue was purified by silica gel column chromatography (PE: EtOAc=20:1 to 5:1) to afford 4-(benzylthio)phenyl)(phenyl) methanol (39a) (2.3 g, 98% yield) as a yellow oil. TLC: Rf=0.5 (PE:EtOAc=5:1, v/v). $^1$H NMR (400 MHz, DMSO-$d_6$) δ 7.37-7.14 (m, 14H), 5.86 (d, J=4.0 Hz, 1H), 5.65 (d, J=4.0 Hz, 1H), 4.19 (s, 2H).

Step 2. Synthesis of ((4-(benzylthio)phenyl)(phenyl)methoxy)(tert-butyl)dimethylsilane (39b)

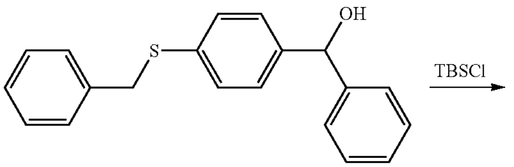

39b

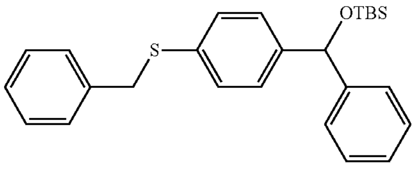

39c

To a solution of 4-(benzylthio)phenyl)(phenyl)methanol (39a) (2.5 g, 8.16 mmol) in DCM (50 mL) was added imidazole (1.67 g, 24.48 mmol) and TBSCl (1.84 g, 12.24 mmol) at 0° C. The reaction mixture was stirred at 23° C. for 16 h. The mixture was diluted with water (100 mL) and extracted with DCM (50 mL×2). The combined organic layer was washed with brine, dried over $Na_2SO_4$, filtered, and concentrated. The residue was purified by silica gel column chromatography (PE:EtOAc=20/1 to 5/1, v/v) to afford ((4-(benzylthio)phenyl)(phenyl)methoxy)(tert-butyl)

dimethylsilane (39b) (3.0 g, 87% yield) as a colorless oil. TLC: Rf=0.7 (silica gel, PE:EtOAc=5:1, v/v).

Step 3. Synthesis of 4-(((tert-butyldimethylsilyl) oxy)(phenyl)methyl)benzenesulfonyl chloride (39c)

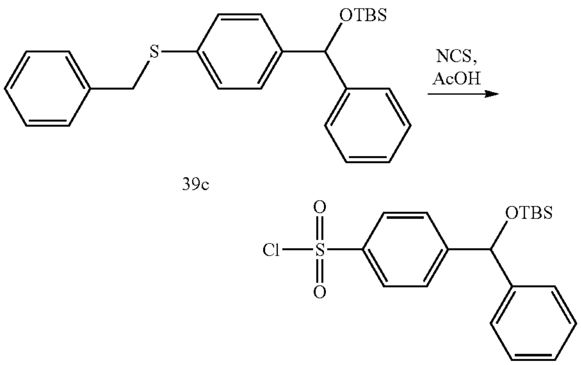

39c

39d

To a solution of ((4-(benzylthio)phenyl)(phenyl)methoxy)(tert-butyl)dimethylsilane (39b) (3.0 g, 7.13 mmol) in AcOH (10 mL), $H_2O$ (2 mL) and acetonitrile (20 mL) was added NCS (1.9 g, 14.26 mmol) at 0° C. The reaction mixture was stirred at 23° C. for 3 h. The mixture was diluted with water (50 mL) and extracted with DCM (50 mL×2). The combined organic layer was washed with brine, dried over $Na_2SO_4$, filtered, and concentrated. The residue was purified by silica gel column chromatography (PE:EtOAc=20/1, v/v) to afford 4-(((tert-butyldimethylsilyl)oxy)(phenyl)methyl)benzenesulfonyl chloride (39c) (2.5 g, 88% yield) as a colorless oil. TLC: Rf=0.6 (PE:EtOAc=5:1, v/v).

Step 4. Synthesis of 1,1-dioxido-2,3-dihydrothiophen-3-yl 4-(((tert-butyldimethylsilyl)oxy)(phenyl) methyl)benzenesulfonate (39d)

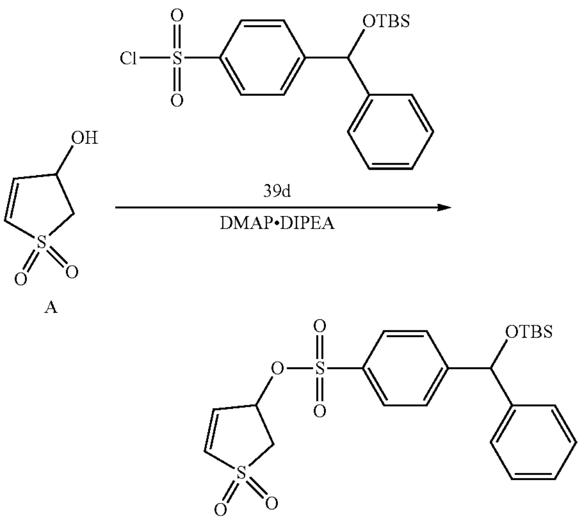

A

39e

To a solution of compound (A) (1.9 g, 4.79 mmol) in DCM (10 mL) was added DMAP (5.85 mg, 47.86 μmol), DIPEA (1.25 mL, 7.18 mmol), and 4-(((tert-butyldimethylsilyl)oxy)(phenyl)methyl)benzenesulfonyl chloride (39c) (1.9 g, 4.79 mmol) at 0° C. The reaction mixture was stirred at 23° C. for 1 h. The mixture was diluted with water (30 mL) and extracted with DCM (20 mL×2). The combined organic layer was washed with brine, dried over $Na_2SO_4$, filtered and concentrated. The residue was purified by silica gel column chromatography (PE:EtOAc=20/1 to 10/1, v/v) to afford 1,1-dioxido-2,3-dihydrothiophen-3-yl 4-(((tert-butyldimethylsilyl)oxy)(phenyl)methyl)benzenesulfonate (39d) (1.5 g, 63% yield) as a white solid. TLC: Rf=0.4 (silica gel, PE:EtOAc=2:1, v/v). $^1$H NMR (400 MHz, DMSO-$d_6$) δ 7.98-7.85 (m, 2H), 7.72 (d, J=8.2 Hz, 2H), 7.48 (d, J=1.1 Hz, 1H), 7.46-7.39 (m, 2H), 7.33 (t, J=7.6 Hz, 2H), 7.27-7.21 (m, 1H), 6.84 (dt, J=7.0, 3.6 Hz, 1H), 6.05 (s, 1H), 5.86 (dddd, J=7.3, 3.5, 2.2, 1.1 Hz, 1H), 5.75 (s, 1H), 3.64 (ddd, J=14.7, 7.5, 3.3 Hz, 1H), 3.28 (dt, J=14.7, 2.6 Hz, 1H), 0.88 (s, 9H), −0.02 (d, J=16.8 Hz, 6H).

Step 5. Synthesis of 1,1-dioxido-2,3-dihydrothiophen-3-yl 4-(hydroxy(phenyl)methyl)benzenesulfonate (39)

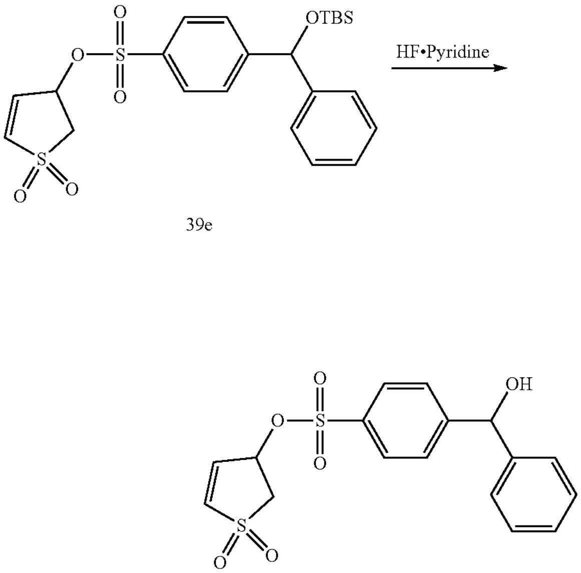

39e

39

To a solution of compound 5 (500 mg, 1.01 mmol) in THF (10 mL) was added pyridine hydrofluoride (300 mg, 3.03 mmol) at 0° C. slowly. The reaction mixture was stirred at 23° C. for 2 h. The mixture was diluted with water (30 mL) and extracted with DCM (20 m Lx 2). The combined organic layer was washed with brine, dried over $Na_2SO_4$, filtered, and concentrated. The residue was purified by silica gel column chromatography (PE:EtOAc=20/1 to 5/1, v/v) to afford 1,1-dioxido-2,3-dihydrothiophen-3-yl 4-(hydroxy(phenyl)methyl)benzenesulfonate (39) (155.2 mg, 40% yield) as a white solid. TLC: Rf=0.5 (DCM:MeOH=15:1, v/v). LCMS: m/z=397.95 $[M+18]^+$; $^1$H NMR (400 MHz, DMSO-$d_6$) δ 7.93 (d, J=8.0 Hz, 2H), 7.71 (d, J=8.1 Hz, 2H), 7.55-7.17 (m, 6H), 6.85 (s, 1H), 6.21 (d, J=4.0 Hz, 1H), 5.85 (d, J=4.3 Hz, 2H), 3.67 (dd, J=14.9, 7.4 Hz, 1H), 3.30 (s, 1H). LCMS: m/z 397.95[M+18], 1.033 min.

Example 40

Synthesis of 1,1-dioxido-2,3-dihydrothiophen-3-yl 2-methyl-4-phenoxybenzenesulfonate (40)

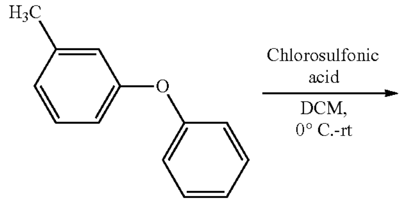

40a

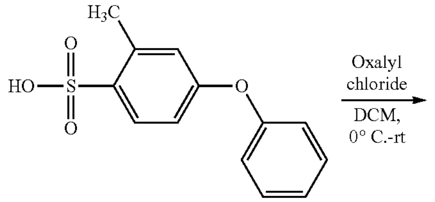

40b

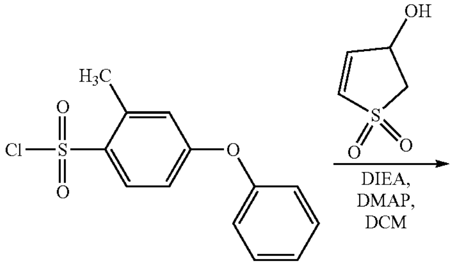

40c

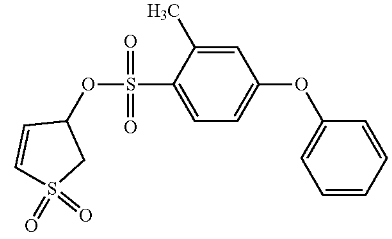

40

Step 1. Synthesis of 2-methyl-4-phenoxybenzenesulfonic acid (40b)

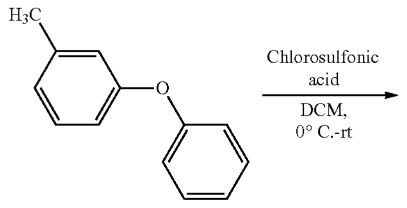

40a

-continued

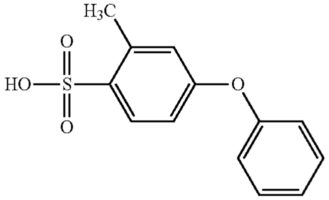

40b

To a solution of 1-methyl-3-phenoxybenzene (40a) (3.0 g, 16.28 mmol) in DCM (50 mL) was added $HSO_3Cl$ (1.90 g, 16.28 mmol). The reaction was stirred at 23° C. for 3 h. The mixture was concentrated to afford 2-methyl-4-phenoxybenzenesulfonic acid (40b) (3.0 g) as a yellow oil.

Step 2. Synthesis of 2-methyl-4-phenoxybenzenesulfonyl chloride (40c)

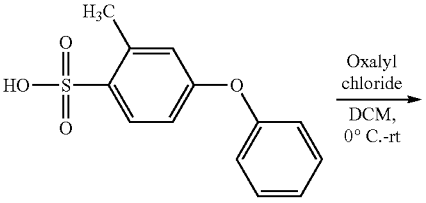

40b

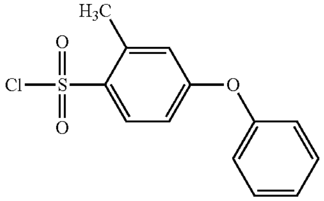

40c

To a solution of 2-methyl-4-phenoxybenzenesulfonic acid (40b) (2.0 g, 7.57 mmol) in DCM (20 mL) was added oxalyl chloride (1.92 g, 15.13 mmol) and cat DMF at 0° C. and the mixture was stirred at 23° C. for 2 h. The mixture was diluted with water (50 mL) and extracted with DCM (50 mL×2). The combined organic layers were washed with brine, dried over $Na_2SO_4$, filtered, and concentrated. The residue was purified by silica gel column chromatography (PE:EtOAc=20/1, v/v) to afford 2-methyl-4-phenoxybenzenesulfonyl chloride (40c) (800 mg, 37% yield) as a white solid. $^1H$ NMR (400 MHz, chloroform-d) δ 7.92 (d, J=8.8 Hz, 1H), 7.49-7.41 (m, 2H), 7.29-7.26 (m, 1H), 7.12-7.05 (m, 2H), 6.93 (d, J=2.4 Hz, 1H), 6.89-6.83 (m, 2H), 6.68 (dd, J=6.8, 2.8 Hz, 1H), 5.68 (dddd, J=7.6, 4.0, 2.8, 1.6 Hz, 1H), 3.56 (dd, J=14.4, 7.6 Hz, 1H), 3.28 (dd, J=14.4, 3.6 Hz, 1H), 2.59 (s, 3H).

Step 3. Synthesis of 1,1-dioxido-2,3-dihydrothiophen-3-yl 2-methyl-4-phenoxybenzenesulfonate (40)

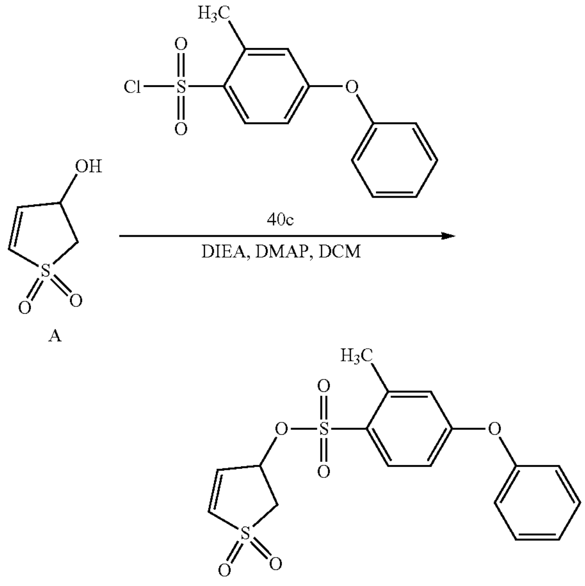

A
40c
40

To a solution of compound (A) (Example A) (200 mg, 1.49 mmol) in DCM (5 mL) was added DIPEA (103 mg, 0.36 mmol), DMAP (289 mg, 2.24 mmol) and 2-methyl-4-phenoxybenzenesulfonyl chloride (40c) (464 mg, 1.64 mmol) at 0° C. The mixture was stirred at 23° C. for 1 h. The mixture was diluted with water (20 mL) and extracted with DCM (30 mL×2). The combined organic layers were washed with brine, dried over $Na_2SO_4$, filtered, and concentrated. The residue was purified by silica gel column chromatography (PE:EtOAc=20/1 to 5/1, v/v) to afford 1,1-dioxido-2,3-dihydrothiophen-3-yl 2-methyl-4-phenoxybenzenesulfonate (40) (179.2 mg, 32% yield) as a white solid. LCMS: m/z=398.0 $[M+18]^+$; $^1H$ NMR (400 MHz, chloroform-d) δ 7.92 (d, J=8.8 Hz, 1H), 7.49-7.41 (m, 2H), 7.29-7.26 (m, 1H), 7.12-7.05 (m, 2H), 6.93 (d, J=2.4 Hz, 1H), 6.89-6.83 (m, 2H), 6.68 (dd, J=6.8, 2.8 Hz, 1H), 5.68 (dddd, J=7.6, 4.0, 2.8, 1.6 Hz, 1H), 3.56 (dd, J=14.4, 7.6 Hz, 1H), 3.28 (dd, J=14.4, 3.6 Hz, 1H), 2.59 (s, 3H).

Example 41

Synthesis of 1,1-dioxido-2,3-dihydrothiophen-3-yl 2-methoxy-4-phenoxybenzenesulfonate (41)

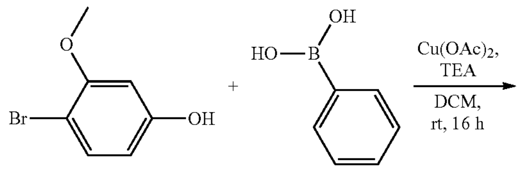

41a
41b

-continued

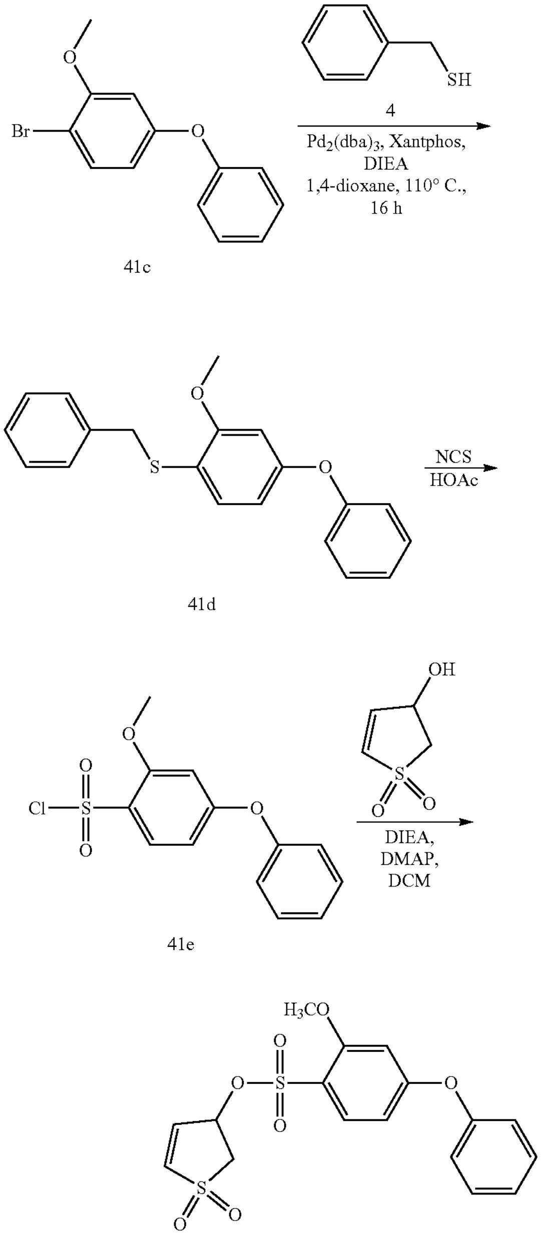

41c
41d
41e
41

Step 1. Synthesis of 1-bromo-2-methoxy-4-phenoxybenzene (41c)

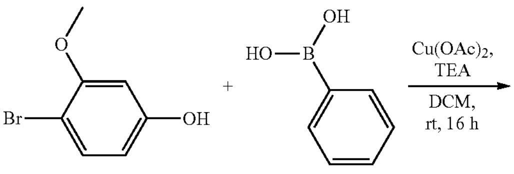

41a
41b

-continued

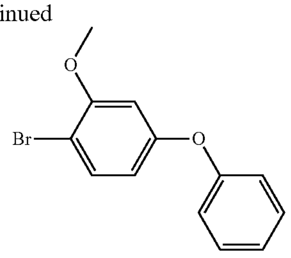

41c

To a solution of 4-bromo-3-methoxyphenol (41a) (4.0 g, 19.70 mmol) in DCM (100 mL) was added phenylboronic acid (41b) (4.80 g, 39.40 mmol), $Cu(OAc)_2$ (7.16 g, 39.40 mmol) and TEA (5.98 g, 59.10 mmol). The mixture was stirred at 23° C. for 16 h and diluted with water (200 mL), extracted with DCM (200 mL). The combined organic layer was washed with brine, dried over $Na_2SO_4$, filtered and concentrated. The residue obtained was purified by silica gel column chromatography (PE:EtOAc=50/1 to 20/1, v/v) to afford 1-bromo-2-methoxy-4-phenoxybenzene (41c) (3.5 g, 64%) as a yellow oil. $^1H$ NMR (400 MHz, chloroform-d) δ 7.44 (d, J=8.6 Hz, 1H), 7.38-7.32 (m, 2H), 7.13 (tt, J=7.1, 1.2 Hz, 1H), 7.05-6.99 (m, 2H), 6.63 (d, J=2.6 Hz, 1H), 6.46 (dd, J=8.6, 2.6 Hz, 1H), 3.84 (s, 3H).

Step 2. Synthesis of benzyl(2-methoxy-4-phenoxyphenyl)sulfane (42d)

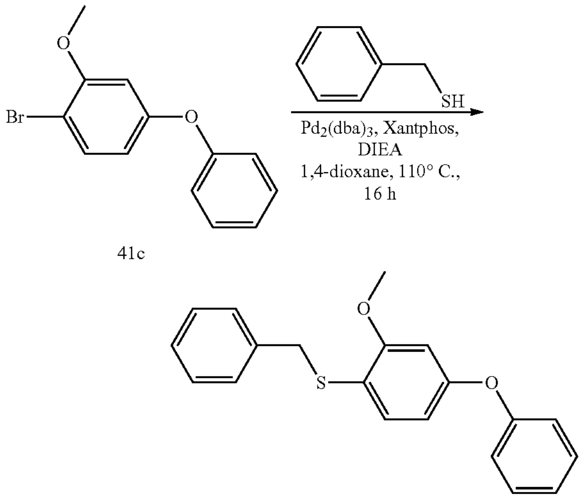

41c

41d

To a solution 1-bromo-2-methoxy-4-phenoxybenzene (41c) (2.5 g, 8.96 mmol) in 1,4-dioxane (25 mL) was added phenylmethanethiol (2.22 g, 17.91 mmol), $Pd_2(dba)_3$ (820 mg, 0.90 mmol), Xantphos (1.04 g, 1.79 mmol), and DIEA (2.32 g, 17.91 mmol), the mixture was stirred at 100° C. for 16 h. The mixture was diluted with water (100 mL) and extracted with EtOAc (100 mL×2). The combined organic layers were washed with brine, dried over $Na_2SO_4$, filtered and concentrated. The residue was purified by silica gel column chromatography (PE:EtOAc=20/1 to 5/1, v/v) to afford benzyl(2-methoxy-4-phenoxyphenyl)sulfane (42b) (2.0 g, 69% yield) as an oil. $^1H$ NMR (400 MHz, chloroform-d) δ 7.41-7.35 (m, 2H), 7.27 (tdd, J=8.4, 5.2, 2.4 Hz, 5H), 7.21 (d, J=8.4 Hz, 1H), 7.19-7.13 (m, 1H), 7.08-7.01 (m, 2H), 6.63 (d, J=2.4 Hz, 1H), 6.48 (dd, J=8.4, 2.4 Hz, 1H), 4.07 (s, 2H), 3.86 (s, 3H).

Step 3. Synthesis of 2-methoxy-4-phenoxybenzenesulfonyl chloride (41e)

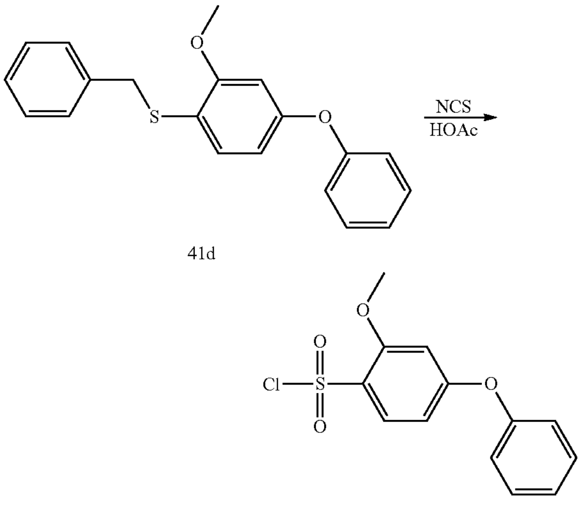

41d

41e

To a solution of benzyl(2-methoxy-4-phenoxyphenyl)sulfane (41d) (1.5 g, 4.65 mmol) in HOAc (40 mL) and $H_2O$ (20 mL) was added NCS (1.86 g, 13.96 mmol) at 0° C., and the mixture was stirred at 0° C. for 1 h. The mixture was diluted with water (100 mL) and extracted with EtOAc (100 mL×2). The combined organic layers were washed with brine, dried over $Na_2SO_4$, filtered, and concentrated. The residue was purified by silica gel column chromatography (PE:EtOAc=50/1, v/v) to afford 2-methoxy-4-phenoxybenzenesulfonyl chloride (42e) (900 mg, 65% yield) as a white solid. $^1H$ NMR (400 MHz, chloroform-d) δ 7.86 (d, J=9.2 Hz, 1H), 7.48-7.42 (m, 2H), 7.38-7.35 (m, 2H), 7.30-7.27 (m, 1H), 7.13-7.08 (m, 2H), 6.67 (d, J=2.4 Hz, 1H), 6.52 (dd, J=9.2, 2.4 Hz, 1H), 3.98 (s, 3H).

Step 4. Synthesis of 1,1-dioxido-2,3-dihydrothiophen-3-yl 2-methoxy-4-phenoxybenzenesulfonate (41)

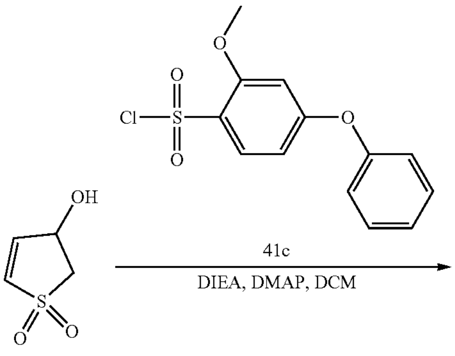

A

-continued

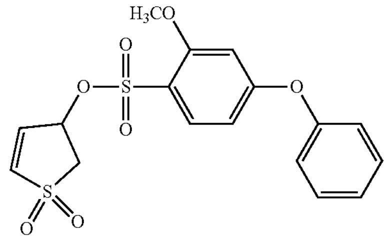

41

To a solution of compound (A) (300 mg, 2.24 mmol) in DCM (5 mL) was added DIPEA (434 mg, 3.35 mmol), DMAP (27 mg, 0.22 mmol) and 2-methoxy-4-phenoxybenzenesulfonyl chloride (41e) (869 mg, 2.91 mmol) at 0° C. The mixture was stirred at 20° C. for 1 h. The mixture was diluted with water (30 mL) and extracted with DCM (30 mL×2). The combined organic layers were washed with brine, dried over Na2SO4, filtered and concentrated. The residue was purified by silica gel column chromatography (PE:EtOAc=20/1 to 5/1, v/v) to afford 1,1-dioxido-2,3-dihydrothiophen-3-yl 2-methoxy-4-phenoxybenzenesulfonate (41) (165.8 mg, 19% yield) as a white solid. LCMS: m/z=413.95 [M+18]+. $^1$H NMR (400 MHz, chloroform-d) δ 7.83 (d, J=8.8 Hz, 1H), 7.48-7.40 (m, 2H), 7.28 (d, J=7.2 Hz, 1H), 7.10 (dd, J=8.0, 1.6 Hz, 2H), 6.84 (dd, J=6.8, 1.6 Hz, 1H), 6.74 (dd, J=6.8, 2.8 Hz, 1H), 6.66 (d, J=2.4 Hz, 1H), 6.54 (dd, J=8.8, 2.4 Hz, 1H), 5.87-5.81 (m, 1H), 3.92 (s, 3H), 3.62 (dd, J=14.4, 7.6 Hz, 1H), 3.40 (dd, J=14.4, 4.0 Hz, 1H).

Example 42

Synthesis of 1,1-dioxido-2,3-dihydrothiophen-3-yl 4-benzyl-3-methylbenzenesulfonate (42)

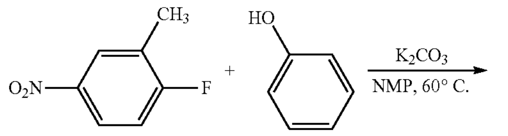

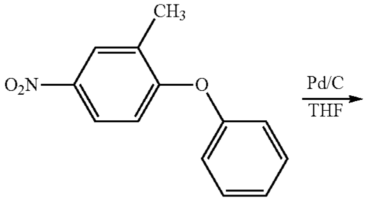

42a

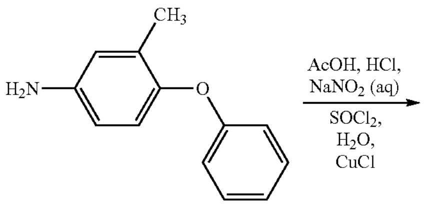

42b

-continued

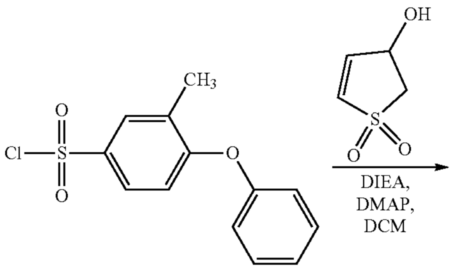

42c

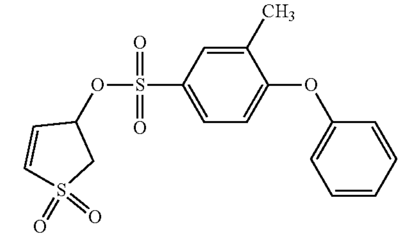

42

Step 1. Synthesis of 2-methyl-4-nitro-1-phenoxybenzene (42a)

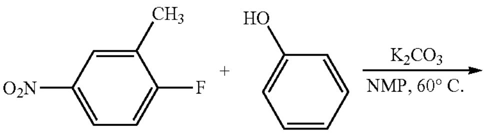

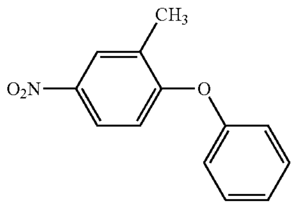

42a

To a solution of 1-fluoro-2-methyl-4-nitrobenzene (5.0 g, 32.2 mmol) in NMP (30 mL) was added phenol (4.5 g, 48.3 mmol) and $K_2CO_3$ (8.9 g, 64.4 mmol). The mixture was stirred at 60° C. for 16 h. The mixture was added water (200 mL) and extracted with EtOAc (100 mL). The organic layers were washed with water, brine and dried over $Na_2SO_4$, concentrated and purified by silica gel column chromatography (PE:EtOAc=20/1 to 5/1, v/v) to afford 2-methyl-4-nitro-1-phenoxybenzene (42a) (6.5 g, 89% yield) as a white solid.

Step 2. Synthesis of 3-methyl-4-phenoxyaniline (42b)

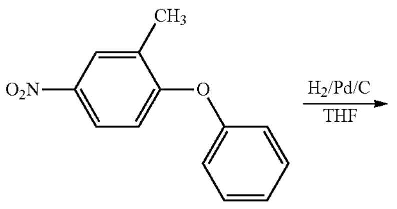

42a

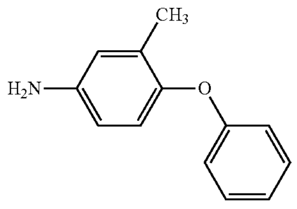

42b

To a solution of 2-methyl-4-nitro-1-phenoxybenzene (42a) (6.5 g, 28.4 mmol) in THF (50 mL) was added Pd/C (600 mg). The mixture was stirred under 1 atm $H_2$ at room temperature for 16 h. The mixture was filtered and concentrated to afford 3-methyl-4-phenoxyaniline (42b) (5.2 g, 100% yield) as a colorless oil.

Step 3. Synthesis of 3-methyl-4-phenoxybenzenesulfonyl chloride (42c)

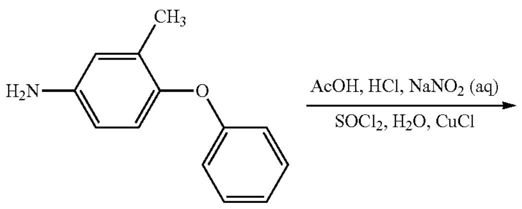

42b

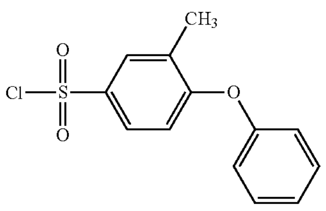

42c

To a three-necked bottle was added 3-methyl-4-phenoxyaniline (42b) (2.0 g, 10.0 mmol), AcOH (12 mL), concentrated HCl (3.5 mL, 42.0 mmol) and aqueous solution of $NaNO_2$ (800 mg, 11.6 mmol) at 0° C. The mixture was stirred at 23° C. for 30 min. In the meantime, to a solution of copper(I) chloride (416 mg, 4.2 mmol) in water (40 mL) was added thionyl chloride (6.2 g, 52.5 mmol) at 0° C. After stirring at 23° C. for 30 min, the diazonium mixture was added at 0° C. and stirred 23° C. for 20 min. The reaction mixture was diluted with water (100 mL) and extracted with EtOAc (50 mL). The organic extracts were washed by brine, dried over $Na_2SO_4$ and concentrated in vacuo to give a crude which was purified by silica gel column chromatography (PE/EtOAc=200/1, v/v) to afford 3-methyl-4-phenoxybenzenesulfonyl chloride (42c) (400 mg, 14% yield) as a yellow oil. $^1H$ NMR (400 MHz, chloroform-d) δ 7.94-7.90 (m, 1H), 7.76 (dd, J=8.8, 2.6 Hz, 1H), 7.47-7.40 (m, 2H), 7.26-7.22 (m, 1H), 7.09-7.03 (m, 2H), 6.82 (d, J=8.7 Hz, 1H), 2.44 (s, 3H).

Step 4. Synthesis of 1,1-dioxido-2,3-dihydrothiophen-3-yl 4-benzyl-3-methylbenzenesulfonate (42)

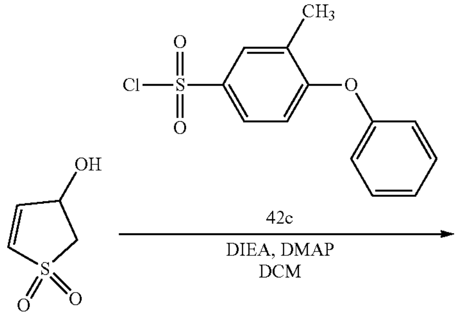

A

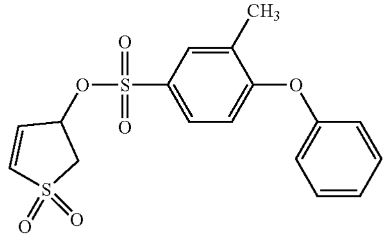

42

To a solution of 3-methyl-4-phenoxybenzenesulfonyl chloride (42c) (400 mg, 1.41 mmol) and compound (A) (172 mg, 1.28 mmol) in DCM (8 mL) was added DIEA (331 mg, 2.56 mmol) and DMAP (16 mg, 0.13 mmol) at 0° C. The mixture was stirred at 23° C. for 2 h. The mixture was concentrated and diluted with DCM (30 mL), washed with brine, dried over $Na_2SO_4$, concentrated, and purified by silica gel column chromatography (PE/EtOAc=20/1 to 5/1, v/v) to afford 1,1-dioxido-2,3-dihydrothiophen-3-yl 4-benzyl-3-methylbenzenesulfonate (42) (130.5 mg, 24% yield) as a white solid. $^1H$ NMR (400 MHz, chloroform-d) δ 7.80 (d, J=2.3 Hz, 1H), 7.64 (dd, J=8.7, 2.4 Hz, 1H), 7.47-7.40 (m, 2H), 7.08-7.02 (m, 2H), 6.87-6.80 (m, 2H), 6.69 (m, 1H), 5.70 (m, 1H), 3.59 (dd, J=14.2, 7.6 Hz, 1H), 3.29 (dd, J=14.2, 4.0 Hz, 1H), 2.43 (s, 3H). LCMS: m/z: 398.00 [M+18]$^+$.

Example 43

Synthesis of 1,1-dioxido-2,3-dihydrothiophen-3-yl 3-methoxy-4-phenoxybenzenesulfonate (43)

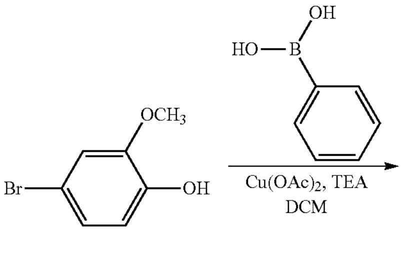

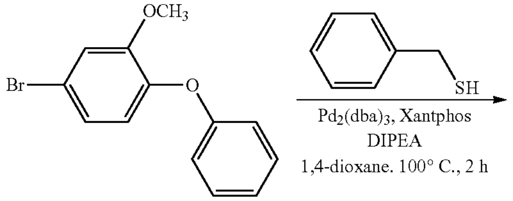

43a

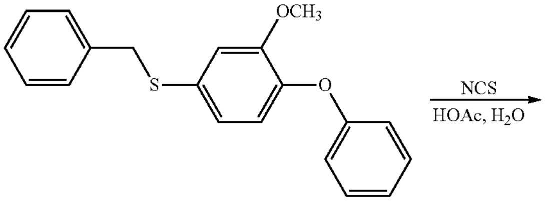

43b

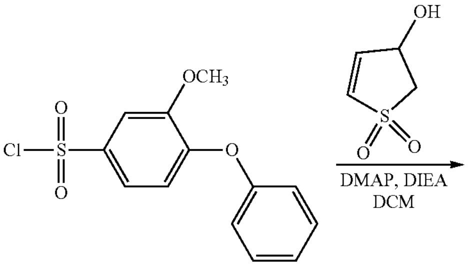

43c

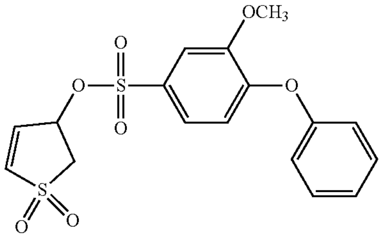

43

Step 1. Synthesis of 4-bromo-2-methoxy-1-phenoxybenzene (43a)

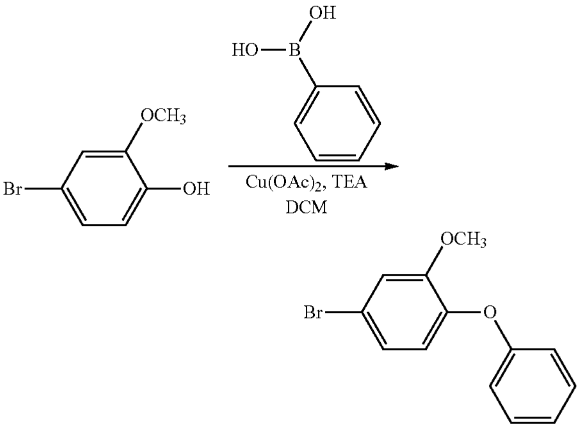

43a

To a solution of 4-bromo-2-methoxyphenol (6.0 g, 29.6 mmol) in DCM (70 mL) was added phenylboronic acid (7.2 mL, 59.1 mmol), TEA (12 mL, 88.7 mmol) and $Cu(OAc)_2$ (6.7 g, 35.5 mmol). The mixture was stirred at 23° C. 16 h. The mixture was filtered through Celite®, diluted with water (100 mL), and extracted with DCM (80 mL×2). The organic layer was washed with brine (80 mL), dried over $Na_2SO_4$, concentrated in vacuo, and purified by silica gel column chromatography (PE) to afford 4-bromo-2-methoxy-1-phenoxybenzene (43a) (1.5 g, 18.3% yield) as a colorless oil. $^1$H NMR (400 MHz, DMSO-$d_6$) δ 7.35 (d, J=2.3 Hz, 1H), 7.34-7.28 (m, 2H), 7.14 (dd, J=8.4, 2.3 Hz, 1H), 7.08-7.02 (m, 1H), 6.97 (d, J=8.5 Hz, 1H), 6.87-6.83 (m, 2H), 3.76 (s, 3H).

Step 2. Synthesis of benzyl(3-methoxy-4-phenoxyphenyl)sulfane (43b)

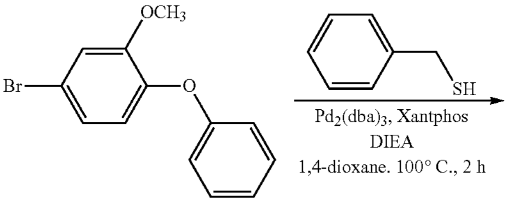

43a

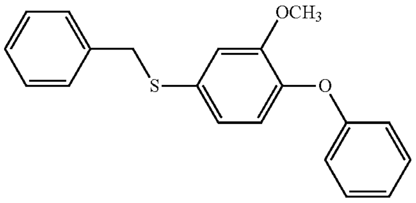

43b

To a solution of compound 1 (1.5 g, 5.37 mmol) in 1, 4-dioxane (10 mL) was added phenylmethanethiol (1.3 g, 10.75 mmol), $Pd_2(dba)_3$ (490 mg, 0.54 mmol), Xantphos (620 mg, 1.08 mmol), and DIEA (1.8 mL, 10.75 mmol). The mixture was stirred at 110° C. under $N_2$ atmosphere for 2 h. The mixture was diluted with water (50 mL) and extracted with EtOAc (50 mL). The organic layer was washed with water (50 mL) and brine (50 mL), dried over $Na_2SO_4$, concentrated in vacuo, and purified by silica gel column chromatography (PE:EtOAc=50:1,v:v) to afford benzyl(3-methoxy-4-phenoxyphenyl)sulfane (43b) (1.3 g, 75.14% yield) as a colorless oil. $^1H$ NMR (400 MHz, DMSO-$d_6$) δ 7.38-7.33 (m, 2H), 7.33-7.31 (m, 1H), 7.31-7.27 (m, 3H), 7.27-7.21 (m, 1H), 7.07-6.99 (m, 2H), 6.93 (d, J=1.8 Hz, 2H), 6.79 (t, J=1.1 Hz, 2H), 4.25 (s, 2H), 3.68 (s, 3H).

Step 3. Synthesis of 3-methoxy-4-phenoxybenzenesulfonyl chloride (43c)

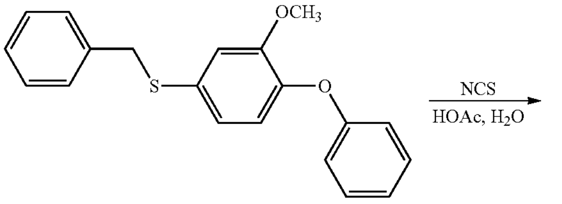

43b

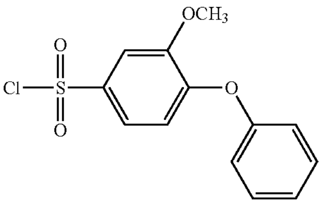

43c

To a solution of benzyl(3-methoxy-4-phenoxyphenyl)sulfane (43b) (1.3 g, 4.03 mmol) in water (5 mL) and HOAc 10 mL) was added NCS (1.6 g, 12.1 mmol) at 0° C. The mixture was stirred at 25° C. for 30 min. The mixture was diluted with water (100 mL) and extracted with EtOAc (50 mL). The organic layer was washed with water (50 mL) and brine (50 mL), dried over $Na_2SO_4$, concentrated in vacuo, and purified by silica gel column chromatography (PE: EtOAc=50:1, v:v) to afford 3-methoxy-4-phenoxybenzenesulfonyl chloride (43c) (1 g, 83.3% yield) as a yellow oil. $^1H$ NMR (400 MHz, DMSO-d) δ 7.36-7.29 (m, 3H), 7.21 (dd, J=8.1, 1.9 Hz, 1H), 7.03 (tt, J=7.3, 1.1 Hz, 1H), 6.96 (s, 1H), 6.87-6.81 (m, 2H), 3.74 (s, 3H).

Step 4. Synthesis of 1,1-dioxido-2,3-dihydrothiophen-3-yl 3-methoxy-4-phenoxybenzenesulfonate (43)

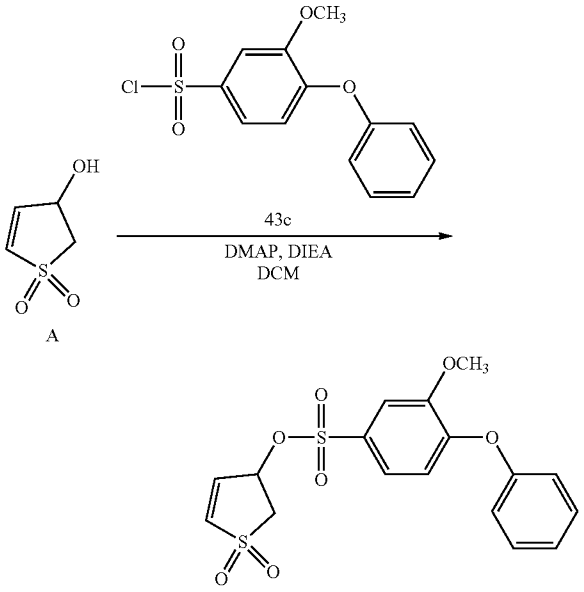

A

43

To a solution of compound (A) in DCM (10 mL) was added DMAP (40 mg, 0.335 mmol), DIEA (0.7 mL, 4.0 mmol) and 3-methoxy-4-phenoxybenzenesulfonyl chloride (43c) (1 g, 3.34 mmol). The mixture was stirred at 25° C. for 15 min. The reaction mixture was diluted with water (50 mL), extracted with EtOAc (30 mL). The organic layer was washed with brine (30 mL), dried over $Na_2SO_4$, concentrated in vacuo, and purified by silica gel column chromatography (PE:EtOAc=5:1,v:v) and Prep-HPLC (0.1% formic acid/ACN/$H_2O$) to afford 1,1-dioxido-2,3-dihydrothiophen-3-yl 3-methoxy-4-phenoxybenzenesulfonate (43) (130.2 mg, 9.85% yield) as a white solid. $^1H$ NMR (400 MHz, chloroform-d) δ 7.46-7.43 (m, 2H), 7.43-7.39 (m, 2H), 7.26-7.20 (m, 1H), 7.09-7.04 (m, 2H), 6.93-6.89 (m, 1H), 6.86 (dd, J=6.7, 1.6 Hz, 1H), 6.69 (dd, J=6.8, 2.9 Hz, 1H), 5.76-5.68 (m, 1H), 3.99 (s, 3H), 3.61 (dd, J=14.2, 7.6 Hz, 1H), 3.31 (dd, J=14.2, 3.8 Hz, 1H). LCMS: m/z: 414.0 $[M+18]^+$. HPLC: 11.006 min, m/z, 98.88% at 214 nm.

Example 44

Synthesis of 1,1-dioxido-2,3-dihydrothiophen-3-yl 4-(phenylthio)benzenesulfonate (44)

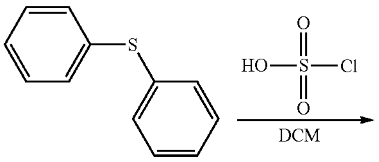

-continued

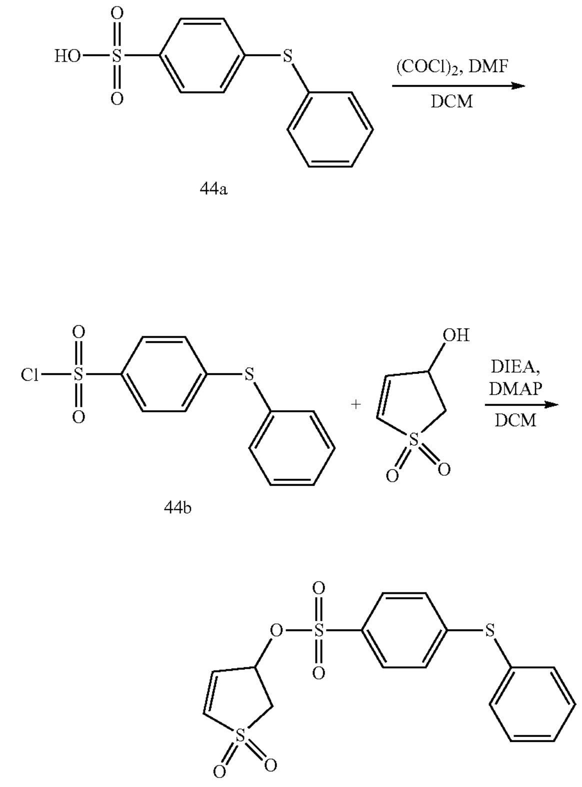

44a

44b

44

Step 1. Synthesis of 4-(phenylthio)benzenesulfonic acid (44a)

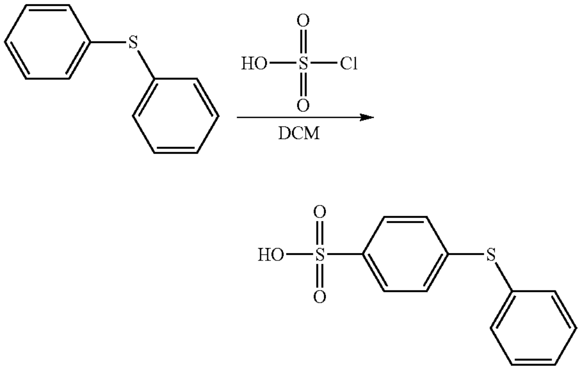

44a

To a solution of diphenylsulfane (5.0 g, 26.84 mmol) in DCM (50 mL) was added sulfurochloridic acid (3.13 g, 26.84 mmol) at 0° C. The mixture was stirred at 23° C. for 2 h. The mixture was concentrated in vacuo to afford 4-(phenylthio)benzenesulfonic acid (44a) (7.1 g, 99.32% yield) as an off-white solid. $^1$H NMR (400 MHz, DMSO-d6) δ 7.60-7.56 (m, 2H), 7.42-7.35 (m, 2H), 7.35-7.29 (m, 3H), 7.29-7.24 (m, 2H).

Step 2. Synthesis of 4-(phenylthio)benzenesulfonyl chloride (44b)

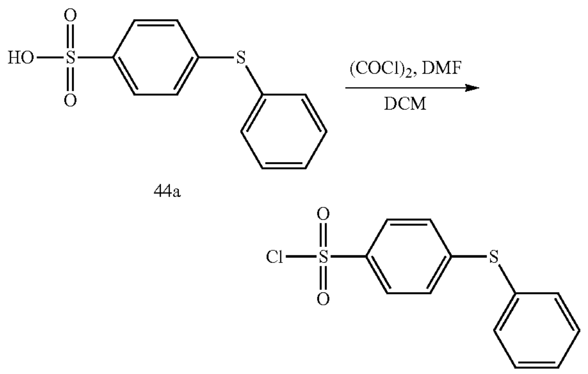

44a

44b

To a solution of 4-(phenylthio)benzenesulfonic acid (44a) (3.0 g, 11.26 mmol) in DCM (30 mL) was added oxalyl chloride (1.72 g, 13.52 mmol), cat DMF (8.3 mg, 0.11 mmol) at 0° C. The mixture was stirred at 23° C. for 2 h. The mixture was concentrated in vacuum to afford the 4-(phenylthio)benzenesulfonyl chloride (44b) (3.2 g, 99.76% yield) as a white solid. $^1$H NMR (400 MHz, DMSO-d6) δ 7.60-7.55 (m, 2H), 7.41-7.35 (m, 2H), 7.35-7.29 (m, 3H), 7.29-7.24 (m, 2H).

Step 3. Synthesis of 1,1-dioxido-2,3-dihydrothiophen-3-yl 4-(phenylthio)benzenesulfonate (44)

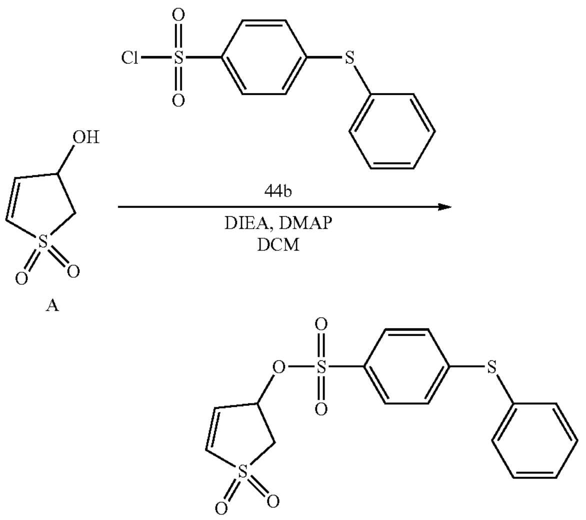

A

44

To a solution of compound (A) (300.0 mg, 2.24 mmol) in DCM (6 mL) was added DMAP (27.32 mg, 0.224 mmol), DIEA (346.85 mg, 2.68 mmol) and 4-(phenylthio)benzenesulfonyl chloride (44b) (700.53 mg, 2.46 mmol) at 0° C. The mixture was stirred at 23° C. for 1 h. The mixture was diluted with water (20 mL), extracted with DCM (20 mL). The organic layer was washed by water (20 mL) and brine (20 mL), dried over $Na_2SO_4$, concentrated in vacuo, and purified by silica gel column chromatography (PE: EtOAc=20/1 to 5/1, v/v) to afford 1,1-dioxido-2,3-dihydrothiophen-3-yl 4-(phenylthio)benzenesulfonate (44) (220.0 mg, 25.72% yield) as a white solid. $^1$H NMR (400 MHz, $CDCl_3$) δ 7.76-7.69 (m, 2H), 7.60-7.53 (m, 2H), 7.51-7.44 (m, 3H), 7.25-7.20 (m, 2H), 6.84 (dd, J=6.7, 1.6 Hz, 1H), 6.66 (dd, J=6.8, 2.8 Hz, 1H), 5.71-5.64 (m, 1H), 3.57 (dd, J=14.2, 7.7 Hz, 1H), 3.26 (dd, J=14.2, 3.9 Hz, 1H). LCMS: m/z: 2.334 min, [M+18]=400.0. HPLC: 98.4% at 254 nm, 99.0% at 214 nm.

Example 45

Synthesis of 1,1-dioxido-2,3-dihydrothiophen-3-yl 4-(phenylsulfonyl)benzenesulfonate (45)

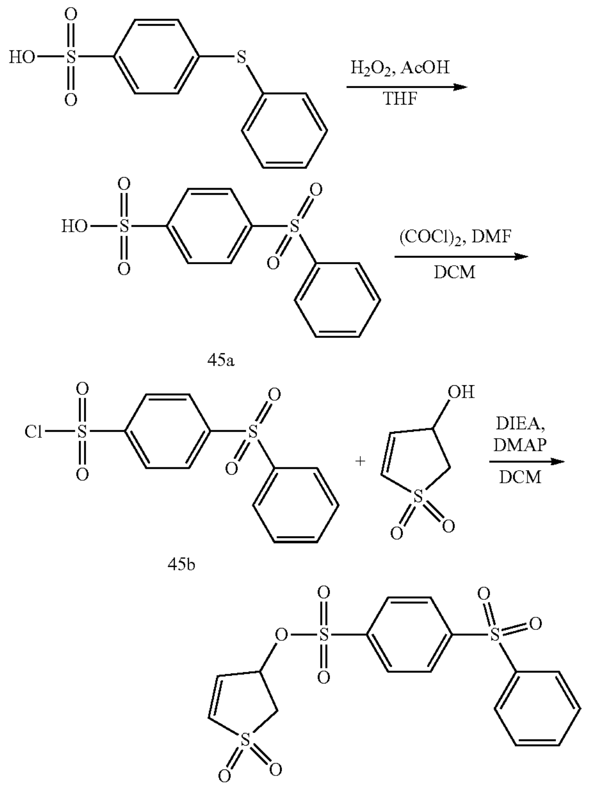

45a

45b

45

Step 1. Synthesis of 4-(cyclohexylsulfonyl)benzenesulfonic acid (45a)

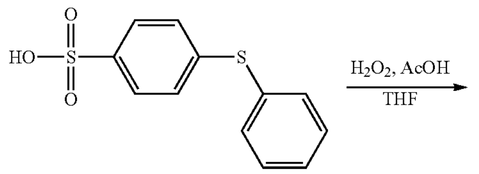

-continued

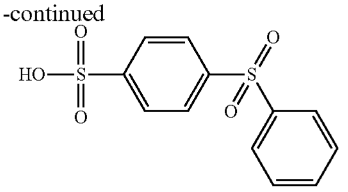

45a

To a solution of 4-(phenylthio)benzenesulfonic acid (3.0 g, 11.26 mmol) in THF (30 mL) was added $H_2O_2$ (30 w/w %, 7.66 g, 67.59 mmol) and AcOH (67.6 mg, 1.13 mmol) at 23° C. The mixture was stirred at 60° C. 16 h. The mixture was quenched with saturated $Na_2SO_3$ (100 mL) and extracted with EtOAc (50 mL×3). The organic layers were dried over $Na_2SO_4$ and concentrated in vacuo to afford 4-(cyclohexylsulfonyl)benzenesulfonic acid (45a) (3.3 g, 98.20% yield) as a white solid. LCMS: m/z: 0.884 min, [M−1]=296.9.

Step 2. Synthesis of 4-(cyclohexylsulfonyl)benzenesulfonyl chloride (45b)

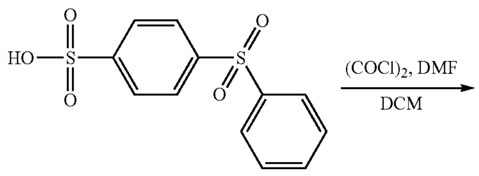

45a

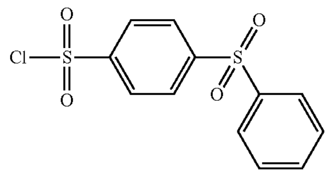

45b

To a solution of 4-(cyclohexylsulfonyl)benzenesulfonic acid (45a) (3.3 g, 11.26 mmol) in DCM (30 mL) was added oxalyl chloride (1.72 g, 13.52 mmol) and a catalytic amount of DMF (8.3 mg, 0.11 mmol) at 0° C. The mixture was stirred at 23° C. for 2 h. The mixture was concentrated in vacuo and purified by silica gel column chromatography (PE:EtOAc=30:1 to 5:1) to afford 4-(cyclohexylsulfonyl) benzenesulfonyl chloride (45b) (1.2 g, 34.25% yield) as a white solid.

Step 3. Synthesis of 1,1-dioxido-2,3-dihydrothiophen-3-yl 4-(phenylsulfonyl)benzenesulfonate (45)

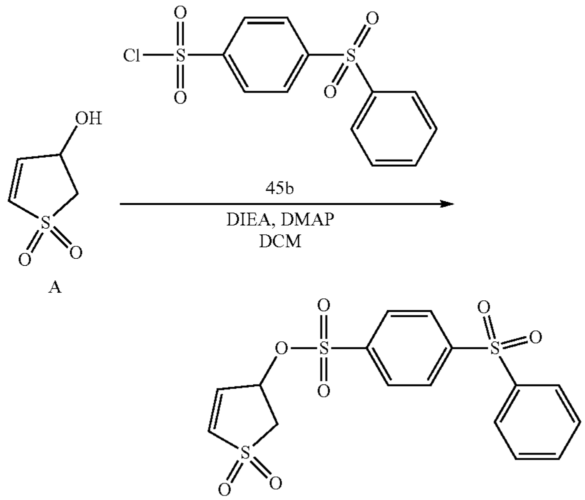

A

45

To a solution of compound (A) (650.0 mg, 4.85 mmol) in DCM (12 mL) was added DMAP (59.20 mg, 0.49 mmol), DIEA (751.50 mg, 5.81 mmol) and 4-(cyclohexylsulfonyl) benzenesulfonyl chloride (45b) (1.69 g, 5.33 mmol) at 0° C. The mixture was stirred at 23° C. for 1 h. The mixture was diluted with water (50 mL) and extracted with DCM (50 mL). The organic layer was washed by water (50 mL) and brine (50 mL), dried over $Na_2SO_4$, concentrated in vacuo, and purified by silica gel column chromatography (PE: EtOAc=20:1 to 2:1) to afford 1,1-dioxido-2,3-dihydrothiophen-3-yl 4-(phenylsulfonyl)benzenesulfonate (45) (400.0 mg, 19.12% yield) as a white solid. $^1$H NMR (400 MHz, $CDCl_3$) δ 8.19-8.13 (m, 2H), 8.09-8.02 (m, 2H), 8.01-7.95 (m, 2H), 7.69-7.62 (m, 1H), 7.61-7.54 (m, 2H), 6.88 (dd, J=6.7, 1.5 Hz, 1H), 6.66 (dd, J=6.8, 2.9 Hz, 1H), 5.77 (m, 1H), 3.64 (dd, J=14.3, 7.6 Hz, 1H), 3.33 (dd, J=14.3, 3.7 Hz, 1H). LCMS: m/z: 1.833 min, [M+18]=432.0. HPLC: 97.2% at 254 nm, 95.7% at 214 nm.

Example 46

Cytotoxicity in Cancer Cell Lines

The cytotoxicity of test compounds was determined for several cell lines including melanoma cell line RPMI-7951, melanoma cell line Sk-Mel-28, melanoma cell line A375, melanoma cell line U87, glioblastoma cell line U87, immortalized human T lymphocyte Jurkat cells, and human pancreatic carcinoma cell line PL-45.

All cells were obtained from ATCC. RPMI, DMEM, EMEM and pen/strep were obtained from Invitrogen. Normocin® was obtained from InvivoGen. FBS was obtained from Gibco. Cell viability reagent Cell-titer glow was obtained from Promega. All test compounds were synthesized as described herein.

The growth media for RPMI and Sk-mel-28 cells was EMEM supplemented with antibiotic/anti-mycotic pen/strep and Normocin® (InvivoGen) and 10% FBS.

The growth media for A375 and PL45 cells was DMEM supplemented with antibiotic/anti-mycotic pen/strep and Normocin® (InvivoGen) and 10% FBS.

The growth media for Jurkat cells and PBMCs was RPMI supplemented with antibiotic/anti-mycotic pen/strep and Normocin® (InvivoGen) and 10% FBS (fetal bovine serum).

Ten (10) mM solutions of each of the test compounds were prepared in dimethyl sulfoxide (DMSO) and serially diluted in DMSO to provide solutions having concentrations of the test compound of 3 mM, 1 mM, 0.3 mM, 0.1 mM, 0.03 mM, or 0.01 mM. Forty (40) μL of each of the solutions were further diluted to 400 μL in the cell specific complete media to provide 10× stock solutions having a 1 mM, 300 μM, 100 μM, 30 μM, 10 μM, 3 μM, 1 μM, or 0.3 μM of the test compound. Ten (10) μL of DMSO was diluted to 400 μL in the complete media and used as the 0 μM control.

For the cytotoxicity studies, all cells were grown in their respective complete media. Confluent cells were harvested and plated into two 96-well tissue culture treated plates at 5,000-8,000 cells/wells in 180 μL media. Twenty (20) μL of each of the 10× stock solutions were added to the wells and mixed.

After incubating for 24 h, media was aspirated out and replaced with 180 μL/well of the fresh media and 20 μL/well of the 10× stock solutions in duplicate wells in duplicate plates (Plates 1 and 2; and 3 and 4) and in quadruplicate wells (Plate 5) were added, mixed and cultured for 48 hours. The final concentrations of each test compound were 100 μM, 30 μM, 10 μM, 3 μM, 1 μM, 0.3 μM, 0.1 μM and 0 μM.

After 48 hours and/or 72 hours following addition of the test compounds, one plate each was removed from the incubator, the media aspirated out, 100 μL of CellTiter-Glo® reagent added to each well, and the resulting luminescent signals measured using a VICTOR-2® plate reader.

The data from the plate reader were exported to GraphPad (Prism) and data processed using non-linear regression and EC50 value determined.

The EC50 of the test compounds was compared to that of ulixertinib, a small molecule ERK1/2 inhibitor with a demonstrated clinical efficacy in patients with solid tumor harboring MAPK pathway alterations in BRAFG and NRAS.

The cytotoxicity EC50 values (mean of three tests) for each of the test compounds with respect to the various cell lines is presented in Table 1 (48 hours) and Table 2 (72 hours).

TABLE 1

| Cytotoxicity EC50 at 48 hours. | | | | | | | |
|---|---|---|---|---|---|---|---|
| | 48 h | | | | | | |
| | Cell lines | | | | | | Primary cells |
| Compound | RPMI | A375 | Sk mel | U87 | Jurkat | PL-45 | PBMC |
| (1) | 1 | 4 | 4 | 1 | 3 | 2.1 | 0.4 |
| (2) | 85 | >100 | >100 | >100 | 53 | [1]— | — |
| (3) | 19 | 14 | >100 | 100 | 6 | — | — |
| (4) | 44 | 19 | 78 | >100 | 7 | — | — |

TABLE 1-continued

| Cytotoxicity EC50 at 48 hours. | | | | | | | |
|---|---|---|---|---|---|---|---|
| | 48 h | | | | | | |
| | Cell lines | | | | | | Primary cells |
| Compound | RPMI | A375 | Sk mel | U87 | Jurkat | PL-45 | PBMC |
| (5) | 72 | 80 | >100 | >100 | 6 | — | — |
| (6) | 40 | 24 | 69 | >100 | >100 | — | — |
| (7) | 19 | 29 | 95 | >100, 10.9 | 10 | — | — |
| (8) | 20 | 11 | >100 | >100 | 0.5 | — | — |
| (9) | 11 | 19 | 71 | 32 | 22 | — | — |
| (10) | 39 | 31 | 38 | >100 | >100 | — | — |
| (11) | 25 | 6.2, >100 | 66 | 3 | 10 | — | — |
| (12) | 100 | >100 | >100 | >100 | >100 | — | — |
| (13) | >100 | >100 | >100 | 1 | 86 | — | — |
| (14) | 12 | 86 | >100 | >100 | 10 | — | — |
| (15) | 36 | 42 | 73 | 100 | 26 | — | — |
| (16) | >100 | >100 | >100 | >100 | 9 | — | — |
| (17) | 1 | 2.6 | 3.2 | 2 | 9 | — | 0.5 |
| (18) | 0.6 | 2 | 2 | 1 | 0.4 | 2.1 | 0.2 |
| (19) | >100 | >100 | 82, >100 | >100 | >100 | — | — |
| (20) | >100 | >100 | >100 | >100 | >100 | — | — |
| (21) | — | 1.3 | — | — | — | 2.1 | — |
| (22) | — | 2.5 | — | — | — | 3.0 | — |
| (23) | — | 23 | — | — | — | 8.3 | — |
| (24) | — | >100 | — | — | — | 49 | — |
| (25) | — | 6 | — | — | — | 0.9 | — |
| (26) | — | 7 | — | — | — | 1.0 | — |
| (27) | — | 7 | — | — | — | 0.9 | — |
| (28) | — | 14 | — | — | — | 0.9 | — |
| (29) | — | 10 | — | — | — | 1.0 | — |
| (30) | — | >100 | — | — | — | 8.8 | — |
| (31) | — | >100 | — | — | — | NT | — |
| (32) | — | >100 | — | — | — | NT | — |
| (33) | — | 1 | — | — | — | 2.3 | — |
| (34) | — | 1.5 | — | — | — | 0.9 | — |
| (35) | — | 1.0 | — | — | — | 1.2 | — |
| (36) | — | 4.3 | — | — | — | 2.1 | — |
| (37) | — | 2.8 | — | — | — | 1.6 | — |
| (38) | — | 0.2 | — | — | — | 0.5 | — |
| (39) | — | 1.3 | — | — | — | 1.5 | — |
| (40) | — | 0.3 | — | — | — | 0.2 | — |
| (41) | — | 0.6 | — | — | — | 0.5 | — |
| (42) | — | 0.5 | — | — | — | 1.2 | — |
| (43) | — | 3.12 | — | — | — | 0.61 | — |
| 1981 | — | 3.21 | — | — | — | 0.8 | — |
| (45) | — | 25 | — | — | — | 2.4 | — |
| Ulixertinib | — | 0.6 | — | — | — | 14 | 31 |

[1]Not measured.

TABLE 2

| Cytotoxicity EC50 at 72 hours. 72 h | | | | | | |
|---|---|---|---|---|---|---|
| | Cell lines | | | | | Primary cells |
| Compound | RPMI | A375 | Sk mel | U87 | Jurkat | PBMC |
| (1) | 4 | 0.8 | 0.3 | 4 | 5 | 0.4 |
| (2) | — | — | — | — | — | — |
| (3) | — | — | — | — | — | — |
| (4) | 26 | 5 | 42 | 53 | 4 | — |
| (5) | 86 | 75 | >100 | >100 | 2 | — |
| (6) | 24 | 19 | 48 | 46 | >100 | — |
| (7) | — | — | — | — | — | — |
| (8) | 16 | 46 | 77 | 37 | 0.5 | — |
| (9) | 10 | 47 | 12 | 28 | 9 | — |
| (10) | 28 | 46 | 25 | 31 | 8 | — |
| (11) | 12 | 97 | 62 | — | — | — |
| (12) | — | — | — | — | — | — |
| (13) | — | — | — | — | — | — |
| (14) | 9.4 | 70 | 100 | — | — | — |

TABLE 2-continued

| Cytotoxicity EC50 at 72 hours. 72 h | | | | | | |
|---|---|---|---|---|---|---|
| | Cell lines | | | | | Primary cells |
| Compound | RPMI | A375 | Sk mel | U87 | Jurkat | PBMC |
| (15) | — | — | — | — | — | — |
| (16) | >100 | 100 | >100 | >100 | 8 | — |
| (17) | 0.4 | 10 | 0.8 | 0.9 | 2 | 0.5 |
| (18) | 0.2 | 13 | 3 | 0.9 | 0.2 | 21 |
| (19) | — | — | — | — | — | — |
| (20) | — | — | — | — | — | — |

Finally, it should be noted that there are alternative ways of implementing the embodiments disclosed herein. Accordingly, the present embodiments are to be considered as illustrative and not restrictive, and the claims are not to be limited to the details given herein but may be modified within the scope and equivalents thereof.

What is claimed is:

1. A compound having the structure of Formula (2):

(2)

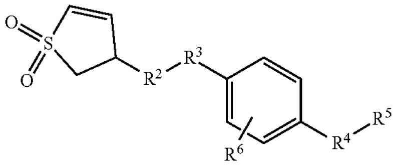

or a pharmaceutically acceptable salt thereof, wherein, $R^2$ is selected from —O—, —NH—, and —N(—$CH_3$)—;

$R^3$ is selected from $C_{1-3}$ alkane-diyl and $C_{1-3}$ heteroalkane-diyl;

$R^4$ is absent or is selected from $C_{1-2}$ alkane-diyl, $C_{1-2}$ heteroalkane-diyl, substituted $C_{1-2}$ alkane-diyl, and substituted $C_{1-2}$ heteroalkane-diyl;

$R^5$ is selected from $C_{5-10}$ cycloalkyl, $C_{5-20}$ aryl, $C_{5-10}$ heterocycloalkyl, $C_{5-20}$ heteroaryl, substituted $C_{5-10}$ cycloalkyl, substituted $C_{5-20}$ aryl, substituted $C_{5-10}$ heterocycloalkyl, and substituted $C_{5-20}$ heteroaryl; and $R^6$ is absent or is selected from $C_{1-3}$ alkyl and $C_{1-3}$ alkoxy, wherein the compound is not selected from:

1,1-dioxido-2,3-dihydrothiophen-3-yl naphthalene-2-sulfonate (1);

1,1-dioxido-2,3-dihydrothiophen-3-yl [1,1'-biphenyl]-4-sulfonate (17);

1,1-dioxido-2,3-dihydrothiophen-3-yl 4-phenoxybenzenesulfonate (18);

(S)-1,1-dioxido-2,3-dihydrothiophen-3-yl 4-phenoxybenzenesulfonate (21); and (R)-1,1-dioxido-2,3-dihydrothiophen-3-yl 4-phenoxybenzenesulfonate (22).

2. The compound of claim 1, wherein $R^3$ is selected from —$CH_2$—, —$CH_2CH_2$—, —$SO_2$—, —$SO_2$—$CH_2$—, —$CH_2$—$SO_2$—, —CO—, —CO—$CH_2$—, —$CH_2$—CO—, —$CH_2$—NH—, and —CO—NH—.

3. The compound of claim 1, wherein $R^3$ is —$SO_2$—.

4. The compound of claim 1, wherein $R^2$ is —O— and $R^3$ is —$SO_2$—.

5. The compound of claim 1, wherein $R^4$ is selected from —O—, —$CH_2$—, —O—$CH_2$—, —$CH_2$—O—, —C(O)—, —C(—OH)—, —S—, and —$S(O)_2$—.

6. The compound of claim 1, wherein $R^5$ is selected from phenyl and cyclohexyl.

7. The compound of claim 1, wherein $R^6$ is absent or is selected from methyl and methoxy.

8. The compound of claim 1, wherein, $R^4$ is absent or is selected from —O—, —$CH_2$—, —O—$CH_2$—, —$CH_2$—O—, —C(O)—, —C(—OH)—, —S—, and —$S(O)_2$—; and $R^5$ is selected from phenyl and cyclohexyl.

9. The compound of claim 1, wherein, $R^2$ is —O—;

$R^3$ is —$S(O)_2$—;

$R^4$ is absent or is selected from —O—, —$CH_2$—, —O—$CH_2$—, —$CH_2$—O—, —C(O)—, —C(—OH)—, —S—, and —$S(O)_2$—;

$R^5$ is selected from phenyl and cyclohexyl; and $R^6$ is absent or is selected from methyl and methoxy.

10. A compound selected from:

3-([1,1'-biphenyl]-4-ylmethoxy)-2,3-dihydrothiophene 1,1-dioxide (5);

3-((4-phenoxybenzyl)oxy)-2,3-dihydrothiophene 1,1-dioxide (6);

1-([1,1'-biphenyl]-4-yl)-2-((1,1-dioxido-2,3-dihydrothiophen-3-yl)oxy) ethan-1-one (9);

1,1-dioxido-2,3-dihydrothiophen-3-yl [1,1'-biphenyl]-4-ylcarbamate (11);

1-([1,1'-biphenyl]-4-yl)-3-(1,1-dioxido-2,3-dihydrothiophen-3-yl) urea (13);

1,1-dioxido-2,3-dihydrothiophen-3-yl 4-phenoxybenzoate (23);

1,1-dioxido-2,3-dihydrothiophen-3-yl [1,1'-biphenyl]-4-carboxylate (24);

1,1-dioxido-2,3-dihydrothiophen-3-yl 4-(benzyloxy)benzenesulfonate (27);

1,1-dioxido-2,3-dihydrothiophen-3-yl 4-benzylbenzenesulfonate (28);

1,1-dioxido-2,3-dihydrothiophen-3-yl 4-(phenoxymethyl)benzenesulfonate (29);

1,1-dioxido-2,3-dihydrothiophen-3-yl 4-cyclohexylbenzenesulfonate (34);

1,1-dioxido-2,3-dihydrothiophen-3-yl 4-(cyclohexyloxy) benzenesulfonate (36);

1,1-dioxido-2,3-dihydrothiophen-3-yl 4-benzoylbenzenesulfonate (38);

1,1-dioxido-2,3-dihydrothiophen-3-yl 4-(hydroxy (phenyl)methyl)benzenesulfonate (39);

1,1-dioxido-2,3-dihydrothiophen-3-yl 2-methyl-4-phenoxybenzenesulfonate (40);

1,1-dioxido-2,3-dihydrothiophen-3-yl 2-methoxy-4-phenoxybenzenesulfonate (41);

1,1-dioxido-2,3-dihydrothiophen-3-yl 4-benzyl-3-methylbenzenesulfonate (42);

1,1-dioxido-2,3-dihydrothiophen-3-yl 3-methoxy-4-phenoxybenzenesulfonate (43);

1,1-dioxido-2,3-dihydrothiophen-3-yl 4-(phenylthio)benzenesulfonate (44);

1,1-dioxido-2,3-dihydrothiophen-3-yl 4-(phenylsulfonyl) benzenesulfonate (45); and a pharmaceutically acceptable salt of any of the foregoing.

11. The compound of claim 10, wherein the compound is selected from:

1,1-dioxido-2,3-dihydrothiophen-3-yl 4-benzoylbenzenesulfonate (38);

1,1-dioxido-2,3-dihydrothiophen-3-yl 2-methyl-4-phenoxybenzenesulfonate (40);

1,1-dioxido-2,3-dihydrothiophen-3-yl 2-methoxy-4-phenoxybenzenesulfonate (41);

1,1-dioxido-2,3-dihydrothiophen-3-yl 3-methoxy-4-phenoxybenzenesulfonate (43); and a pharmaceutically acceptable salt of any of the foregoing.

12. The compound of claim 10, wherein the compound is selected from:

3-([1,1'-biphenyl]-4-ylmethoxy)-2,3-dihydrothiophene 1,1-dioxide (5);

1-([1,1'-biphenyl]-4-yl)-2-((1,1-dioxido-2,3-dihydrothiophen-3-yl)oxy) ethan-1-one (9);

1,1-dioxido-2,3-dihydrothiophen-3-yl [1,1'-biphenyl]-4-ylcarbamate (11);

1-([1,1'-biphenyl]-4-yl)-3-(1,1-dioxido-2,3-dihydrothiophen-3-yl) urea (13);

1,1-dioxido-2,3-dihydrothiophen-3-yl [1,1'-biphenyl]-4-carboxylate (24); and 1,1-dioxido-2,3-dihydrothiophen-3-yl 4-cyclohexylbenzenesulfonate (34);

or a pharmaceutically acceptable salt of any of the foregoing.

13. The compound of claim 10, wherein the compound is selected from:

3-((4-phenoxybenzyl)oxy)-2,3-dihydrothiophene 1,1-dioxide (6);

1,1-dioxido-2,3-dihydrothiophen-3-yl [1,1'-biphenyl]-4-ylcarbamate (11);

1,1-dioxido-2,3-dihydrothiophen-3-yl 4-phenoxybenzoate (23);

1,1-dioxido-2,3-dihydrothiophen-3-yl 4-(benzyloxy)benzenesulfonate (27);

1,1-dioxido-2,3-dihydrothiophen-3-yl 4-benzylbenzenesulfonate (28);

1,1-dioxido-2,3-dihydrothiophen-3-yl 4-(phenoxymethyl)benzenesulfonate (29);

1,1-dioxido-2,3-dihydrothiophen-3-yl 4-(cyclohexyloxy) benzenesulfonate (36);

1,1-dioxido-2,3-dihydrothiophen-3-yl 4-benzoylbenzenesulfonate (38);

1,1-dioxido-2,3-dihydrothiophen-3-yl 4-(hydroxy (phenyl)methyl)benzenesulfonate (39);

1,1-dioxido-2,3-dihydrothiophen-3-yl 2-methyl-4-phenoxybenzenesulfonate (40);

1,1-dioxido-2,3-dihydrothiophen-3-yl 2-methoxy-4-phenoxybenzenesulfonate (41);

1,1-dioxido-2,3-dihydrothiophen-3-yl 4-benzyl-3-methylbenzenesulfonate (42);

1,1-dioxido-2,3-dihydrothiophen-3-yl 3-methoxy-4-phenoxybenzenesulfonate (43);

1,1-dioxido-2,3-dihydrothiophen-3-yl 4-(phenylthio)benzenesulfonate (44);

1,1-dioxido-2,3-dihydrothiophen-3-yl 4-(phenylsulfonyl) benzenesulfonate (45); and a pharmaceutically acceptable salt of any of the foregoing.

14. A pharmaceutical composition comprising the compound of claim 1 or a pharmaceutically acceptable salt thereof, and a pharmaceutically acceptable vehicle.

15. A pharmaceutical composition comprising the compound of claim 10 or a pharmaceutically acceptable salt thereof, and a pharmaceutically acceptable vehicle.

16. The compound 1,1-dioxido-2,3-dihydrothiophen-3-yl 2-methyl-4-phenoxybenzenesulfonate (40) or a pharmaceutically acceptable salt thereof:

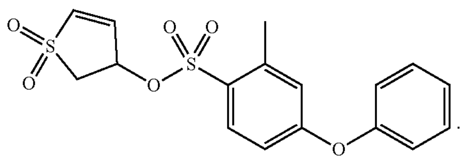 [SMILES: Cc1cc(Oc2ccccc2)ccc1S(=O)(=O)OC1C=CS(=O)(=O)C1]

17. A pharmaceutical composition comprising the compound of claim 16 or a pharmaceutically acceptable salt thereof, and a pharmaceutically acceptable vehicle.

* * * * *